United States Patent
Levy et al.

(10) Patent No.: US 10,759,792 B2
(45) Date of Patent: Sep. 1, 2020

(54) CAMKII INHIBITORS AND USES THEREOF

(71) Applicant: The Johns Hopkins University, Baltimore, MD (US)

(72) Inventors: Daniel Emil Levy, San Mateo, CA (US); Howard Schulman, Palo Alto, CA (US); Bheema Rao Paraselli, San Diego, CA (US); Nangunoori Sampath Kumar, Telangana (IN); Brahmaiah Dabbugoddu, Telangana (IN); Chundru Balasubramanyam, Andhra Pradesh (IN)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/506,501

(22) PCT Filed: Sep. 4, 2015

(86) PCT No.: PCT/US2015/048640
§ 371 (c)(1),
(2) Date: Feb. 24, 2017

(87) PCT Pub. No.: WO2016/037106
PCT Pub. Date: Mar. 10, 2016

(65) Prior Publication Data
US 2017/0247374 A1 Aug. 31, 2017

Related U.S. Application Data

(60) Provisional application No. 62/046,450, filed on Sep. 5, 2014.

(51) Int. Cl.
*C07D 471/04* (2006.01)

(52) U.S. Cl.
CPC .................. *C07D 471/04* (2013.01)

(58) Field of Classification Search
CPC .................................. C07D 471/04
USPC ....................................... 546/85
See application file for complete search history.

(56) References Cited

U.S. PATENT DOCUMENTS

| | | | | |
|---|---|---|---|---|
| 2,690,441 | A * | 9/1954 | Burtner | C07D 471/04 544/126 |
| 6,518,245 | B1 | 2/2003 | Anderson et al. | |
| 7,632,815 | B2 | 12/2009 | Anderson | |
| 8,440,656 | B2 | 5/2013 | Anderson et al. | |
| 8,685,969 | B2 | 4/2014 | Liu et al. | |
| 9,896,446 | B2 * | 2/2018 | Breslin | C07D 493/08 |
| 9,914,730 | B2 * | 3/2018 | Breslin | C07D 493/08 |
| 2006/0057639 | A1 | 3/2006 | Pitt et al. | |
| 2007/0004684 | A1 * | 1/2007 | Sennhenn | C07D 471/04 514/150 |
| 2008/0255121 | A1 | 10/2008 | Tagashira et al. | |
| 2009/0005356 | A1 | 1/2009 | Blaney et al. | |
| 2011/0281862 | A1 | 11/2011 | Gambacorti Passerini et al. | |
| 2016/0024078 | A1 | 1/2016 | Levy et al. | |

FOREIGN PATENT DOCUMENTS

| | | | | |
|---|---|---|---|---|
| CN | 101218241 | A | 7/2008 | |
| DE | 1913124 | * | 10/1969 | ............ A61K 31/44 |
| EP | 0705831 | A2 | 4/1996 | |
| EP | 2161271 | A1 | 3/2010 | |
| GB | 1268773 | A | 3/1972 | |
| JP | 2008-540664 | A | 11/2008 | |
| JP | 2008-542433 | A | 11/2008 | |
| JP | 2008-545660 | A | 12/2008 | |
| JP | 2009-523812 | A | 6/2009 | |
| JP | 2010-529035 | A | 8/2010 | |
| JP | 2012-501984 | A | 1/2012 | |
| WO | WO-2004/058764 | A1 | 7/2004 | |
| WO | WO-2006/040451 | A2 | 4/2006 | |
| WO | WO-2006/124863 | A2 | 11/2006 | |
| WO | WO-2006/131552 | A1 | 12/2006 | |
| WO | WO-2009/102498 | A1 | 8/2009 | |
| WO | WO-2010/011768 | A1 | 1/2010 | |
| WO | WO-2010/017048 | A1 | 2/2010 | |
| WO | WO-2010025872 | A2 * | 3/2010 | ............ C07D 471/04 |
| WO | WO-2010/051501 | A1 | 5/2010 | |
| WO | WO-2010/073719 | A1 | 7/2010 | |
| WO | WO-2011/159857 | A1 | 12/2011 | |
| WO | WO-2013/042035 | A1 | 3/2013 | |
| WO | WO-2014/052699 | A1 | 4/2014 | |
| WO | WO-2014052699 | A1 * | 4/2014 | ............ C07D 493/08 |
| WO | WO-2014/138212 | | 9/2014 | |
| WO | WO-2014/138212 | A1 | 9/2014 | |

OTHER PUBLICATIONS

Caplus English abstract AN ;1977:60178, Sagitullin et al (Year: 1977).*
Schneider et al , Chemoselective functionalization of a-carbolines at the C-2, C-3, C-4, and C-6 positions using Suzuki-Miyaura reactions (Year: 2009).*
Anderson, M.E. et al., CaMKII in myocardial hypertrophy and heart failure, Journal of Molecular and Cellular Cardiology, 51(4):468-473 (2011).
Anderson, M.E. et al., KN-93, an Inhibitor of Multifunctional Ca++/Calmodulin-Dependent Protein Kinase, Decreses Early Afterdepolarizations in Rabbit Heart, The Journal of Pharmacology and Experimental Therapeutics, 287(3):996-1006 (1998).
Ang, E.S.M. et al., Calcium/Calmodulin-Dependent Kinase Activity is Required for Efficient Induction of Osteoclast Differentiation and Bone Resorption by Receptor Activator of Nuclear Factor Kappa B Ligand (RANKL), Journal of Cellular Physiology, 212(3):787-795 (2007).

(Continued)

*Primary Examiner* — Rita J Desai
(74) *Attorney, Agent, or Firm* — Fish & Richardson P.C.

(57) ABSTRACT

The present invention provides compounds useful as inhibitors of $Ca^{2+}$/calmodulin-dependent protein kinase (CaMKII), compositions thereof, and methods of using the same.

5 Claims, 1 Drawing Sheet

(56) References Cited

OTHER PUBLICATIONS

Ashpole, N. M. et al., Calcium/Calmodulin-dependent Protein Kinase II (CaMKII) Inhibition Induces Neurotoxicity via Dysregulation of Glutamate/Calcium Signaling and Hyperexcitability, 287(11):8495-8506 (2012).
Backs, J. et al., The delta isoform of CaM kinase II is required for pathological cardiac hypertrophy and remodeling after pressure overload, PNAS, 106(7):2342-2347 (2009).
Banumathi, E. et al., VEGF-Induced Retinal Angiogenic Signaling Is Critically Dependent on Ca2+ Signaling by Ca2+/Calmodulin-Dependent Protein Kinase II, IOVS, 52(6):3103-3111 (2011).
Berge, S. M. et al, Pharmaceutical Salts, Journal of Pharmaceutical Sciences, 66(1): 1-19 (1977).
Butler, J. et al, Recognizing Worsening Chronic Heart Failure as an Entity and an End Point in Clinical Trials, JAMA, 312(8):789-790 (2014).
Cannady, R. et al, Potentiation of amygdala AMPA receptor activity selectively promotes escalated alcohol self-administration in a CaMKII-dependent manner, Addict. Biol., 22(3): 652-664 (2017).
Chao, L.H. et al., A Mechanism for Tunable Autoinhibition in the Structure of a Human Ca2+/Calmodulin-Dependent Kinase II Holoenzyme, Cell, 146(5):732-745 (2011).
Chao. L. H. et al, Intersubunit capture of regulatory segments is a component of cooperative CaMKII activation, Nature Structural & Molecular Biology, 17(3): 264-272 (2010).
Chelu, M.G. et al., Calmodulin kinase II-mediated sarcoplasmic reticulum Ca2+ leak promotes atrial fibrillation in mice, The Journal of Clinical Investigation, 119(7):1940-1951 (2009).
Chen, Y. et al., Ca2+/Calmodulin-Dependent Protein Kinase II alpha is Required for the Initiation and Maintenance of Opioid-Induced Hyperalgesia, The Journal of Neuroscience, 30(1):38-46 (2010).
Corradi, F. et al, Ranolazine in the prevention of anthracycline cardiotoxicity, Pharmacol. Res., 79: 88-102 (2014).
Crown, E.D. et al., Calcium/calmodulin dependent kinase II contributes to persistent central neuropathic pain following spinal cord injury, PAIN, 153(3):710-721 (2012).
Daft, P. G. et al, The growth and aggressive behavior of human osteosarcoma is regulated by a CaMKII-controlled autocrine VEGF signaling mechanism, PLoS One, 10(4): 1-20 (2015).
Di Pasquale, E. et al, CaMKII inhibition rectifies arrhythmic phenotype in a patient-specific model of catecholaminergic polymorphic ventricular tachycardia, Cell Death Dis., 4: 1-11 (2013).
Dobrev, D. et al., Novel molecular targets for atrial fibrillation therapy, Nature Reviews, 11(4):275-291 (2012).
Erickson, J.R. and Anderson, M.E., CaMKII and Its Role in Cardiac Arrhythmia, Journal of Cardiovascular Electrophysiology, 19(12):1332-1336 (2008).
Fan, G.H. et al., Inhibition of Calcium/Calmodulin-Dependent Protein Kinase II in Rat Hippocampus Attenuates Morphine Tolerance and Dependence, Molecular Pharmacology, 56(1):39-45 (1999).
Fujikawa, K. et al., Calcium/calmodulin-dependent protein kinase II (CaMKII) regulates tumour necrosis factor-related apoptosis inducing ligand (TRAIL);mediated apoptosis of fibroblast-like synovial cells (FLS) by phosphorylation of Akt, Clinical and Experimental Rheumatology, 27(6):952-957 (2009).
Hama, T. et al, Palladium-Catalyzed α-Arylation of Zinc Enolates of Esters: Reaction Conditions and Substrate Scope, The Journal of Organic Chemistry, 78: 8250-8266 (2013).
House, S.J. and Singer, H.A., CaMKII-delta Isoform Regulation of Neointima Formation After Vascular Injury, Arterioscler Thromb Vasc Biol, 38(3):441-447 (2008).
Illario, M. et al., Calcium-calmodulin-dependent kinase II (CaMKII) mediates insulin-stimulated proliferation and glucose uptake, Cellular Signaling, 21(5):786-792 (2009).
International Search Report for PCT/US2014/020700, 3 pages, dated May 23, 2014.
Joiner, M.A. et al., CaMKII determines mitochondrial stress responses in heart, Nature, 491(7423):269-273 (2012).
Li, K. et al, βCaMKII in Lateral Habenula Mediates Core Symptoms of Depression, Science, 341: 1016-1020 (2013).
Li, W. et al., The Multifunctional Ca2+/Calmodulin-dependent Kinase II delta (CaMKIIdelta) Controls Neointima Formation after Carotid Ligation and Vascular Smooth Muscle Cell Proliferation through Cell Cycle Regulation by p21, The Journal of Biological Chemistry, 286(10):7990-7999 (2011).
Liang, D. et al., Increased Expression of Ca2+/Calmodulin-dependent protein Kinase II alpha during chronic morphine exposure, Neuroscience, 123(3):769-775 (2004).
Ling, H. et al, Ca2+/Calmodulin-dependent protein kinase II δ mediates myocardial ischemia/reperfusion injury through nuclear factor-κB, Circ. Res, 112(6): 935-944 (2013).
Ling, H. et al, Requirement for Ca2+/calmodulin-dependent kinase II in the transition from pressure overload-induced cardiac hypertrophy to heart failure in mice, J. Clin. Invest., 119(5): 1230-40 (2009).
Liu, N. et al., Calmodulin kinase II inhibition prevents arrhythmias in RyR2R4496C+/– mice with catecholaminergic polymorphic ventricular tachycardia, Journal of Molecular and Cellular Cardiology, 50(1):214-222 (2011).
Liu, X. et al., CaMKII promotes TLR-triggered proinflammatory cytokine and type I interferon production by directly binding and activating TAK1 and IRF3 in macrophages, Blood, 112(13):4961-4970 (2008).
Loweth, J. A. et al, Persistent Reversal of Enhanced Amphetamine Intake by Transient CaMKII Inhibition, The Journal of Neuroscience, 33(4): 1411-1416 (2013).
Luo, F. et al., Reversal of Chronic Inflammatory Pain by Acute Inhibition of Ca2+/Calmodulin-Dependent Protein Kinase II, The Journal of Pharmacology and Experimental Therapeutics, 325(1):267-275 (2008).
Mamaeva, O.A. et al., Calcium/Calmodium-Dependent Kinase II Regulates Notch-1 Signaling in Prostate Cancer Cells, Journal of Cellular Biochemistry, 106(1):25-32 (2009).
Mesubi, O.O. and Anserson, M.E., Atrial remodelling in atrial fibrillation: CaMKII as a nodal proarrhythmic signal, Cardiovasc. Res., 109(4): 542-57 (2016).
Mustroph, J. et al, CaMKII as a target for arrhythmia suppression, Pharmacol. Ther., 1-10 (2016).
Neef, S. et al., CaMKII-Dependent Diastolic SR Ca2+ Leak and Elevated Diastolic Ca2+ Levels in Right Atrial Myocardium of Patients with Atrial Fibrillation, Circulation Research, 106(6):1134-1144 (2010).
Ozcan, L. and Tabas, I., CaMKII in cardiometabolic disease, AGING, 6(4): 1-2 (2014).
Ozcan, L. et al, Activation of calcium/calmodulin-dependent protein kinase II in obesity mediates suppression of hepatic insulin signaling, Cell Metab., 18(6): 803-815 (2013).
Ozcan, L. et al., Calcium Signaling through CaMKII Regulates Hepatic Glucose Production in Fasting and Obesity, Cell Metabolism, 15(5):937-951 (2012).
Panteleev, J. et al, Ligand Control in Enantioselective Desymmetrization of Bicyclic Hydrazines: Rhodium(I)-Catalyzed Ring-Opening versus Hydroarylation, Adv. Synth. Catal., 350: 2892-2902 (2008).
Pereira, G. R. et al, 7-Chloroquinolinotriazoles: Synthesis by the azideealkyne cycloaddition click chemistry, antimalarial activity, cytotoxicity and SAR studies, European Journal of Medicinal Chemistry, 73: 295-309 (2014).
Rellos, P. et al., Structure of the CaMK11delta/Calmodulin Complex Reveals the Molecular Mechanism of CaMKII Kinase Activation, PLoS Biology, 8(7):e1000426 (2010).
Rokhlin, O.W. et al., Calcium/Calmodulin-Dependent Kinase II Plays an Important Role in Prostate Cancer Cell Survival, Cancer Biology & Therapy, 6(5):732-742 (2007).
Rokita, A.G. and Anderson, M.E., New Therapeutic Targets in Cardiology: Arrhythmias and Ca2+/Calmodulin-Dependent Kinase II (CaMKII), Circulation, 126(17):2125-2139 (2012).

(56) References Cited

OTHER PUBLICATIONS

Sag, C.M. et al., Calcium/Calmodulin-Dependent Protein Kinase II Contributes to Cardiac Arrhythmogenesis in Heart Failure, Circ Heart Fail, 2(6):664-675 (2009).
Sag, C.M. et al., CaMKII-dependent SR Ca leak contributes to doxorubicin-induced impaired Ca handling in isolated cardiac myocytes, Journal of Molecular and Cellular Cardiology, 51(5):749-759 (2011).
Sanders, P.N. et al., CaMKII As A Pro-Asthmatic Signal, Am J. Respir Crit Care Med, 183:A2795 (2011).
Sanders, P.N. et al., CaMKII Is Essential for the Proasthmatic Effects of Oxidation, Sci Transl Med, 5(195):195ra97, (2013).
Schulman, H. and Anderson, M.E., Ca2+/calmodulin-dependent protein kinase II in heart failure, Drug Discovery Today: Disease Mechanisms, 7(2):e117 (2010).
Sebag, S. C. et al, Mitochondrial CaMKII inhibition in airway epithelium protects against allergic asthma, JCL Insight, 2(3): e88297 (2017).
Shevchuk, N. V. et al, A Convenient Synthesis of (1H-Azol-1-yl)piperidines, Synthesis, 44: 2041-2048 (2012).
Sossalla, S. et al., Inhibition of Elevated Ca2+/Calmodulin-Dependent Protein Kinase II Improves Contractility in Human Failing Myocardium, 107(9):1150-1161 (2010).
Timmins, J.M. et al., Calcium/calmodulin-dependent protein kinase II links ER stress with Fas and mitochondrial apoptosis pathways, The Journal of Clinical Investigation, 119(10):2925-2941 (2009).
Vest, R.S. et al., Effective Post-insult Neuroprotection by a Novel Ca2+/Calmodulin-dependent Protein Kinase II (CaMKII) Inhibitor, The Journal of Biological Chemistry, 285(27):20675-20682 (2010).
Wang, P. et al, Baicalin alleviates ischemia-induced memory impairment by inhibiting the phosphorylation of CaMKII in hippocampus, Brain Research, 1645: 95-103 (2016).
Wang, Y.Y. et al, The emerging role of CaMKII in cancer, Oncotarget, 6(14): 11725-34 (2015).
Written Opinion for PCT/US2014/020700, 11 pages, dated May 23, 2014.
Xiao, C. et al., Inhibition of CaMKII-mediated c-FLIP expression sensitizes malignant melanoma cells to Trail-induced apoptosis, Experimental Cell Research, 304(1):244-255 (2005).
Yuan, K. et al., alpha-CaMKII controls the growth of human osteosarcoma by regulating cell cycle progression, Laboratory Investigation, 87(9):938-950 (2007).
Zeitz, K.P. et al., The contribution of autophosphorylated alpha-calcium-calmodulin kinase II to injury-induced persistent pain, Neuroscience, 128(4):889-898 (2004).
Zhang, R. et al., Calmodulin kinase II inhibition protects against structural heart disease, Nature Medicine, 11(4):409-417 (2005).
Zhang, T. et al., The Cardiac-specific Nuclear deltaB Isoform of Ca2+/Calmodium-dependent Protein Kinase II Induces Hypertrophy and Dilated Cardiomyopathy Associated with Increased Protein Phosphatase 2A Activity, The Journal of Biological Chemistry, 277(2):1261-1267 (2002).
Zhang, W. et al., Inhibition of Calcium-Calmodulin-Dependent Kinase II Suppresses Cardiac Fibroblast Proliferation and Extracellular Matrix Secretion, J Cardiovasc Pharmacol, 55(1):96-105 (2010).
International Search Report for PCT/US2015/048640, 9 pages (dated Feb. 10, 2016).
Selig, R. et al., A frozen analogue approach to aminopyridinylimidazoles leading to novel and promising p38 MAP kinase inhibitors, J. Med. Chem., 55(19):8429-39 (2012).
Song, Y. et al., Beta-carbolines as specific inhibitors of cyclin-dependent kinases, Bioorg. Med. Chem. Lett., 12(7):1129-32 (2002).
Stephenson, L. et al., Synthesis of some substituted alpha-carbolines, Journal of the Chemical Society, Section C: Organic Chemistry, pp. 1355-1359 (1970).
Tahri, A. et al., Synthesis of alpha-carbolines and beta-carbolines via Intramolecular Diels-Alder Reactions of 2(1H)-Pyrazinones, Tetrahedron, 54(43):13211-13226 (1998).
Written Opinion for PCT/US2015/048640, 14 pages (dated Feb. 10, 2016).

* cited by examiner

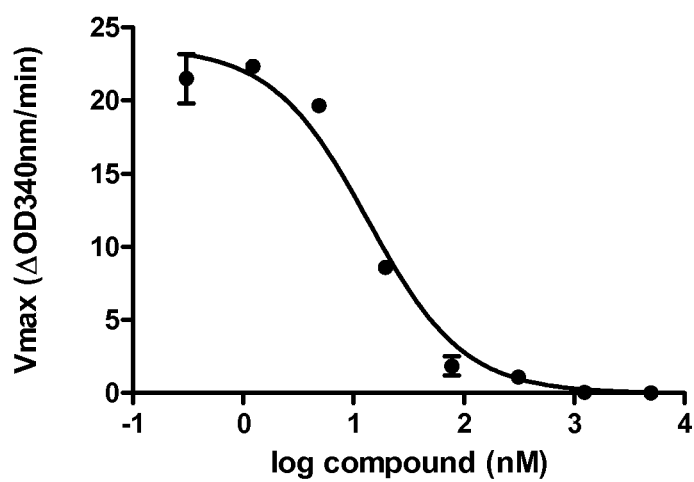
CaMKII δ enzyme inhibition curve for compound I-7.

CAMKII INHIBITORS AND USES THEREOF

BACKGROUND

Cardiovascular disease remains the number one cause of death in developed countries. Furthermore, incidence of cardiovascular disease has increased dramatically in developing countries. Although cardiovascular disease usually affects older adults, the antecedents of cardiovascular disease, notably atherosclerosis, begin in early life, making primary prevention efforts necessary from childhood. It is estimated that 1 in 3 people will die from complications attributable to cardiovascular disease. "Global Atlas on Cardiovascular Disease Prevention and Control", World Health Organization; January 2012. In order to stem the tide and address the shifting epidemiology of this disease, measures to prevent or reverse cardiovascular disease must be taken.

Obesity and diabetes mellitus are often linked to cardiovascular disease, due to increased atherosclerosis and direct effects on the heart, as are a history of chronic kidney disease and hypercholesterolemia. In fact, cardiovascular disease is the most life threatening of the diabetic complications and diabetics are two- to four-fold more likely to die of cardiovascular-related causes than nondiabetics.

Diet and exercise, even when used in conjunction with the current pharmacotherapy, often do not provide sufficient control of cardiovascular symptoms. The continuing and highly prevalent problem of cardiovascular disease highlights the overwhelming need for new drugs to treat this condition and its underlying causes. Among these conditions is heart failure, for which there continues to be a need for better therapy as hospitalized patients have poor outcomes as their conditions progresses following discharge (Butler, J, Braunwald, E. and Gheorghiade, M. "Recognizing Worsening Chronic Heart Failure as an Entity and an End Point in Clinical Trials" (2014) *JAMA* 312:789-790)

SUMMARY

Previous studies resulted in identification of the novel compounds set forth in Table I (WO2014138212 A1).

TABLE 1

Previously identified CaMKII inhibitors

| Compound ID | Compound Structure |
|---|---|
| I-1 | 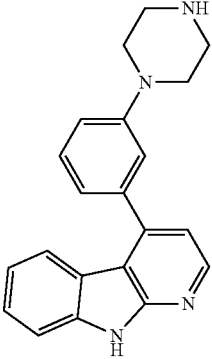 [SMILES: c1cc(-c2ccnc3[nH]c4ccccc4c23)cc(N2CCNCC2)c1] |
| I-2 | 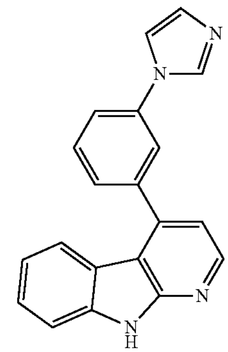 [SMILES: c1cc(-c2ccnc3[nH]c4ccccc4c23)cc(-n2ccnc2)c1] |
| I-3 | 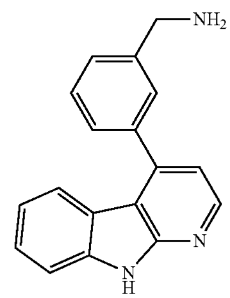 [SMILES: NCc1cccc(-c2ccnc3[nH]c4ccccc4c23)c1] |
| I-4 | 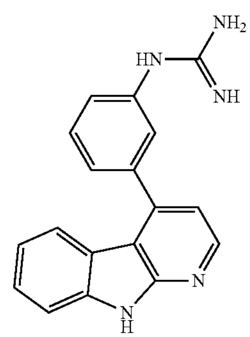 [SMILES: N=C(N)Nc1cccc(-c2ccnc3[nH]c4ccccc4c23)c1] |
| I-5 | 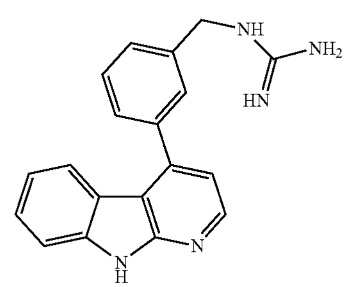 [SMILES: N=C(N)NCc1cccc(-c2ccnc3[nH]c4ccccc4c23)c1] |
| I-6 | 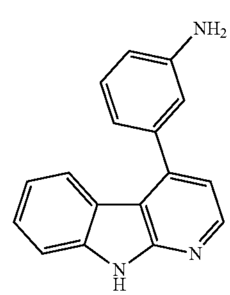 [SMILES: Nc1cccc(-c2ccnc3[nH]c4ccccc4c23)c1] |

TABLE 1-continued

Previously identified CaMKII inhibitors

| Compound ID | Compound Structure |
|---|---|
| I-7 | 3-(9H-pyrido[2,3-b]indol-4-yl)-N-(2-aminoethyl)aniline |
| I-8 | 3-(9H-pyrido[2,3-b]indol-4-yl)-N-(3-aminopropyl)aniline |
| I-9 | 2-(3-(9H-pyrido[2,3-b]indol-4-yl)phenoxy)ethanamine |
| I-10 | 3-(3-(9H-pyrido[2,3-b]indol-4-yl)phenoxy)propanamine |
| I-11 | N-(2-aminoethyl)-3-(7-methyl-9H-pyrido[2,3-b]indol-4-yl)aniline |
| I-12 | N-(2-aminoethyl)-3-(7-methoxy-9H-pyrido[2,3-b]indol-4-yl)aniline |
| I-13 | N-(2-aminoethyl)-3-(6-methyl-9H-pyrido[2,3-b]indol-4-yl)aniline |
| I-14 | N-(2-aminoethyl)-3-(6-chloro-9H-pyrido[2,3-b]indol-4-yl)aniline |
| I-15 | N-(2-aminoethyl)-2-(9H-pyrido[2,3-b]indol-4-yl)aniline |

TABLE 1-continued

Previously identified CaMKII inhibitors

| Compound ID | Compound Structure |
|---|---|
| I-16 | 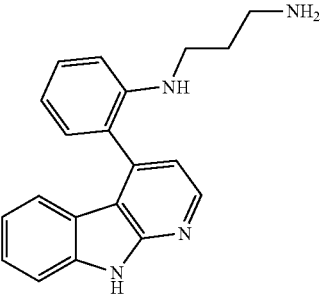 [SMILES: NCCCNc1ccccc1-c1ccnc2[nH]c3ccccc3c12] |

It has now been found that compounds of this invention, and pharmaceutically acceptable compositions thereof, are effective as inhibitors of $Ca^{2+}$/calmodulin-dependent protein kinase II (CaMKII). Such compounds have the general formula I:

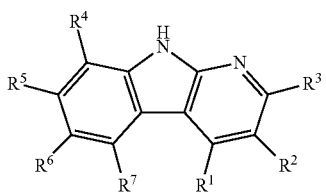

or a pharmaceutically acceptable salt thereof, wherein:
$R^1$ is an acyclic group or a 5-membered or 6-membered heteroaryl group selected from the list of structures consisting of

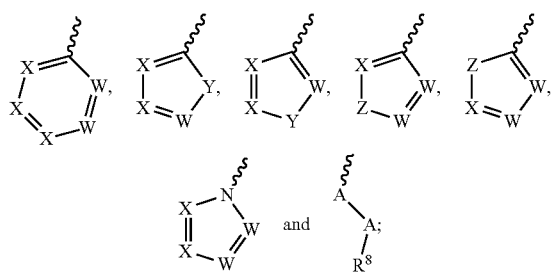

each of $R^2$, $R^3$, $R^4$, $R^5$, $R^6$ and $R^7$ is independently selected from the group consisting of hydrogen, halogen, —CN, —CF$_3$, —OR, —NR$_2$, —NO$_2$, —COOR, —CONR$_2$, and —R;
each A is independently selected from the group consisting of a covalent bond, an optionally substituted methylene, an optionally substituted cis ethylene, an optionally substituted trans ethylene, an acetylene, C(O), S(O) and S(O)$_2$; wherein, if one A is an optionally substituted methylene, an optionally substituted cis ethylene, an optionally substituted trans ethylene, an acetylene, C(O), S(O) or S(O)$_2$, the other must be a covalent bond or an optionally substituted methylene;
$R^8$ is selected from the group consisting of hydrogen, NH$_2$, guanidino, 4-7 membered optionally substituted saturated heterocyclic ring having 1-2 heteroatoms independently selected from nitrogen, oxygen and sulfur, and 5-6 membered heteroaromatic ring having 1-2 heteroatoms independently selected from sulfur, nitrogen and oxygen;
each W is independently N or CR$^9$;
each X independently N or CR$^{10}$;
Y is O, S or NR$^{11}$;
Z is O, S or NR$^{12}$;
$R^9$ is selected from the group consisting of hydrogen, L-R$^{13}$, NH$_2$, guanidino, 4-7 membered optionally substituted saturated heterocyclic ring having 1-2 heteroatoms independently selected from nitrogen, oxygen or sulfur, and 5-6 membered heteroaromatic ring having 1-2 heteroatoms independently selected from sulfur, nitrogen and oxygen; wherein, when one $R^9$ group is present, $R^9$ cannot be hydrogen and when two $R^9$ groups are present, one must be hydrogen and the other must not be hydrogen;
each $R^{10}$ is independently selected from the group consisting of hydrogen, halogen, —CN, —CF$_3$, —OR, —NR$_2$, —NO$_2$, —COOR, —CONR$_2$, and —R;
$R^{11}$ is hydrogen, NH$_2$, 4-7 membered optionally substituted saturated heterocyclic ring having 1-2 heteroatoms independently selected from nitrogen, oxygen and sulfur, and 5-6 membered heteroaromatic ring having 1-2 heteroatoms independently selected from sulfur, nitrogen and oxygen;
$R^{12}$ is hydrogen or optionally substituted $C_{1-6}$ aliphatic;
L is a covalent bond or a straight or branched $C_{1-6}$ aliphatic group, wherein one or more methylene groups are independently and optionally replaced by —NR$^{14}$— or —O—;
$R^{13}$ is selected from the group consisting of NH$_2$, guanidino, 4-7 membered optionally substituted saturated heterocyclic ring having 1-2 heteroatoms independently selected from nitrogen, oxygen or sulfur, and 5-6 membered heteroaromatic ring having 1-2 heteroatoms independently selected from sulfur, nitrogen and oxygen;
each $R^{14}$ is independently hydrogen or $C_{1-3}$ aliphatic; and
each R is independently hydrogen or optionally substituted $C_{1-6}$ aliphatic.

Compounds of the present invention, and pharmaceutically acceptable compositions thereof, are useful for treating a variety of diseases, disorders or conditions. For example, provided compounds are useful in treatment of diseases, disorders or conditions associated with the regulation and inhibition of CaMKII. Such diseases, disorders, or conditions include those described herein.

Compounds provided by this invention are also useful for the study of CaMKII enzymes in biological and pathological phenomena; the study of intracellular signal transduction pathways occurring in cardiac, vascular and other bodily tissues; and the comparative evaluation of new CaMKII inhibitors or other regulators of inflammation in vitro or in vivo.

BRIEF DESCRIPTION OF THE DRAWING

FIG. 1 presents results of an in vitro CaMKII enzyme inhibition assay for compound I-7.

DETAILED DESCRIPTION OF CERTAIN EMBODIMENTS

1. General Description of Compounds of the Invention:
In certain embodiments, the present invention provides inhibitors of CaMKII. In some embodiments, such compounds include those of formula I:

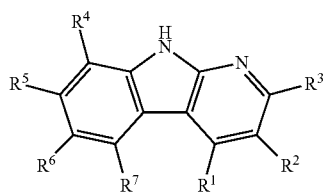

I or a pharmaceutically acceptable salt thereof, wherein:
$R^1$ is an acyclic group or a 5-membered or 6-membered heteroaryl group selected from the list of structures consisting of

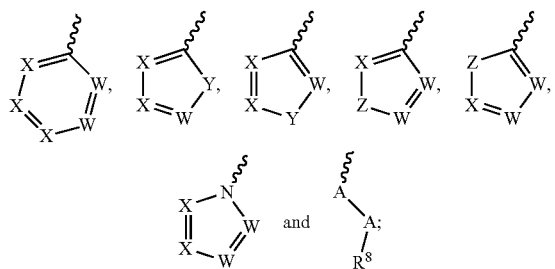

each of $R^2$, $R^3$, $R^4$, $R^5$, $R^6$ and $R^7$ is independently selected from the group consisting of hydrogen, halogen, —CN, —$CF_3$, —OR, —$NR_2$, —$NO_2$, —COOR, —$CONR_2$, and —R;
each A is independently selected from the group consisting of a covalent bond, an optionally substituted methylene, an optionally substituted cis ethylene, an optionally substituted trans ethylene, an acetylene, C(O), S(O) and $S(O)_2$; wherein, if one A is an optionally substituted methylene, an optionally substituted cis ethylene, an optionally substituted trans ethylene, an acetylene, C(O), S(O) or $S(O)_2$, the other must be a covalent bond or an optionally substituted methylene;
$R^8$ is selected from the group consisting of hydrogen, $NH_2$, guanidino, 4-7 membered optionally substituted saturated heterocyclic ring having 1-2 heteroatoms independently selected from nitrogen, oxygen and sulfur, and 5-6 membered heteroaromatic ring having 1-2 heteroatoms independently selected from sulfur, nitrogen and oxygen;
each W is independently N or $CR^9$;
each X independently N or $CR^{10}$;
Y is O, S or $NR^{11}$;
Z is O, S or $NR^{12}$;
$R^9$ is selected from the group consisting of hydrogen, L-$R^{13}$, $NH_2$, guanidino, 4-7 membered optionally substituted saturated heterocyclic ring having 1-2 heteroatoms independently selected from nitrogen, oxygen or sulfur, and 5-6 membered heteroaromatic ring having 1-2 heteroatoms independently selected from sulfur, nitrogen and oxygen; wherein, when one $R^9$ group is present, $R^9$ cannot be hydrogen and when two $R^9$ groups are present, one must be hydrogen and the other must not be hydrogen;
each $R^{10}$ is independently selected from the group consisting of hydrogen, halogen, —CN, —$CF_3$, —OR, —$NR_2$, —$NO_2$, —COOR, —$CONR_2$, and —R;
$R^{11}$ is hydrogen, $NH_2$, 4-7 membered optionally substituted saturated heterocyclic ring having 1-2 heteroatoms independently selected from nitrogen, oxygen and sulfur, and 5-6 membered heteroaromatic ring having 1-2 heteroatoms independently selected from sulfur, nitrogen and oxygen;
$R^{12}$ is hydrogen or optionally substituted $C_{1-6}$ aliphatic;
L is a covalent bond or a straight or branched $C_{1-6}$ aliphatic group, wherein one or more methylene groups are independently and optionally replaced by —$NR^{14}$— or —O—;
$R^{13}$ is selected from the group consisting of $NH_2$, guanidino, 4-7 membered optionally substituted saturated heterocyclic ring having 1-2 heteroatoms independently selected from nitrogen, oxygen or sulfur, and 5-6 membered heteroaromatic ring having 1-2 heteroatoms independently selected from sulfur, nitrogen and oxygen;
each $R^{14}$ is independently hydrogen or $C_{1-3}$ aliphatic; and
each R is independently hydrogen or optionally substituted $C_{1-6}$ aliphatic.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

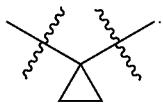 [SMILES: *C1(*)CC1]

As used herein, the term "cyclobutylenyl" refers to a bivalent cyclobutyl group of the following structure:

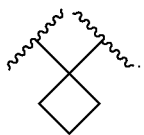 [SMILES: *C1(*)CCC1]

As used herein, the term "oxetanyl" refers to a bivalent oxetanyl group of the following structure:

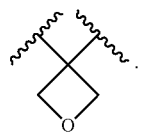

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic.

The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ)$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-N(R^\circ)_2$; or $-(C_{1-4}$ straight or branched)alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2-$(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered, saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

3. Description of Exemplary Embodiments:

In certain embodiments, the present invention provides inhibitors of CaMKII. In some embodiments, such compounds include those of formula I:

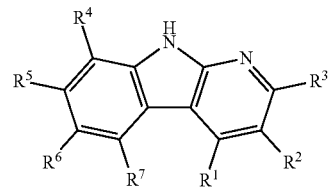

or a pharmaceutically acceptable salt thereof, wherein:
$R^1$ is an acyclic group or a 5-membered or 6-membered heteroaryl group selected from the list of structures consisting of

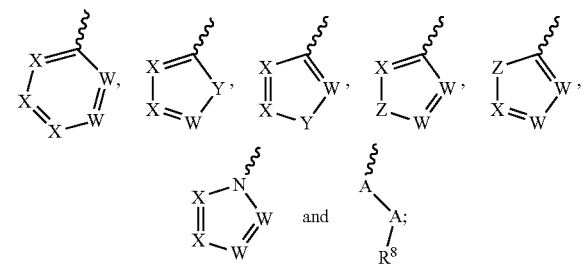

each of $R^2$, $R^3$, $R^4$, $R^5$, $R^6$ and $R^7$ is independently selected from the group consisting of hydrogen, halogen, —CN, —CF$_3$, —OR, —NR$_2$, —NO$_2$, —COOR, —CONR$_2$, and —R;

each A is independently selected from the group consisting of a covalent bond, an optionally substituted methylene, an optionally substituted cis ethylene, an optionally substituted trans ethylene, an acetylene, C(O), S(O) and S(O)$_2$; wherein, if one A is an optionally substituted methylene, an optionally substituted cis ethylene, an optionally substituted trans ethylene, an acetylene, C(O), S(O) or S(O)$_2$, the other must be a covalent bond or an optionally substituted methylene;

$R^8$ is selected from the group consisting of hydrogen, NH$_2$, guanidino, 4-7 membered optionally substituted saturated heterocyclic ring having 1-2 heteroatoms independently selected from nitrogen, oxygen or sulfur, and 5-6 membered heteroaromatic ring having 1-2 heteroatoms independently selected from sulfur, nitrogen and oxygen;

each W is independently N or CR$^9$;
each X independently N or CR$^{10}$;
Y is O, S or NR$^{11}$;
Z is O, S or NR$^{12}$;
$R^9$ is selected from the group consisting of hydrogen, L-R$^{13}$, NH$_2$, guanidino, 4-7 membered optionally substituted saturated heterocyclic ring having 1-2 heteroatoms independently selected from nitrogen, oxygen and sulfur, and 5-6 membered heteroaromatic ring having 1-2 heteroatoms independently selected from sulfur, nitrogen and oxygen; wherein, when one $R^9$ group is present, $R^9$ cannot be hydrogen and when two $R^9$ groups are present, one must be hydrogen and the other must not be hydrogen;

each $R^{10}$ is independently selected from the group consisting of hydrogen, halogen, —CN, —CF$_3$, —OR, —NR$_2$, —NO$_2$, —COOR, —CONR$_2$, and —R;

$R^{11}$ is hydrogen, NH$_2$, 4-7 membered optionally substituted saturated heterocyclic ring having 1-2 heteroatoms independently selected from nitrogen, oxygen and sulfur, and 5-6 membered heteroaromatic ring having 1-2 heteroatoms independently selected from sulfur, nitrogen and oxygen;

$R^{12}$ is hydrogen or optionally substituted $C_{1-6}$ aliphatic;

L is a covalent bond or a straight or branched $C_{1-6}$ aliphatic group, wherein one or more methylene groups are independently and optionally replaced by —$NR^{14}$— or —O—;

$R^{13}$ is selected from the group consisting of $NH_2$, guanidino, 4-7 membered optionally substituted saturated heterocyclic ring having 1-2 heteroatoms independently selected from nitrogen, oxygen or sulfur, and 5-6 membered heteroaromatic ring having 1-2 heteroatoms independently selected from sulfur, nitrogen and oxygen;

each $R^{14}$ is independently hydrogen or $C_{1-3}$ aliphatic; and each R is independently hydrogen or optionally substituted $C_{1-6}$ aliphatic.

As defined generally above, $R^1$ is an acyclic group or a 5-membered or 6-membered heteroaryl group selected from the list of structures consisting of

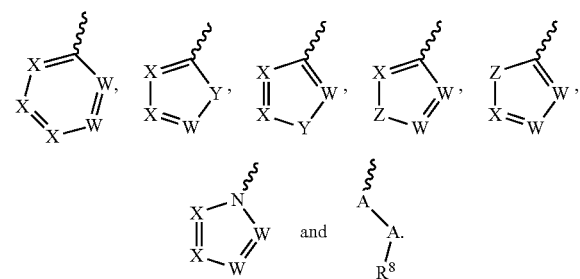

In some embodiments $R^1$ is

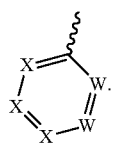

In some embodiments $R^1$ is

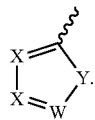

In some embodiments $R^1$ is

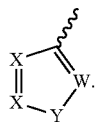

In some embodiments $R^1$ is

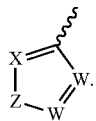

In some embodiments $R^1$ is

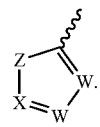

In some embodiments $R^1$ is

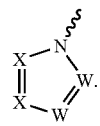

In some embodiments $R^1$ is

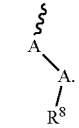

In some embodiments, $R^1$ is selected from the list of structures consisting of

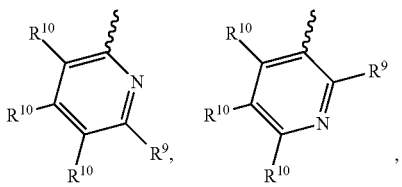

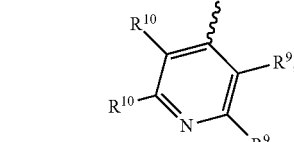

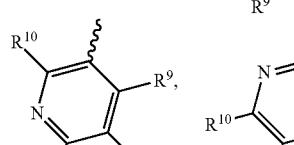

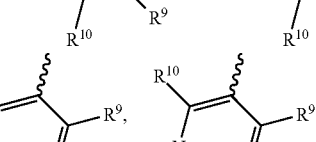

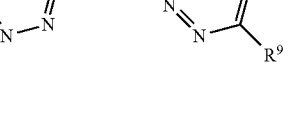

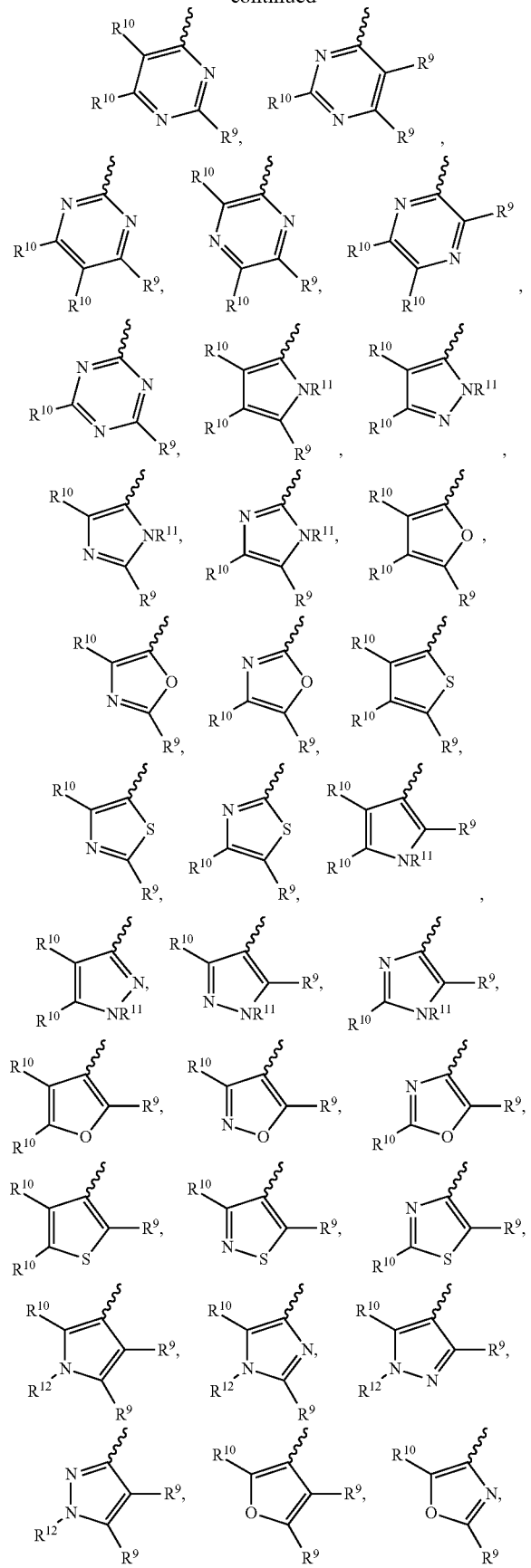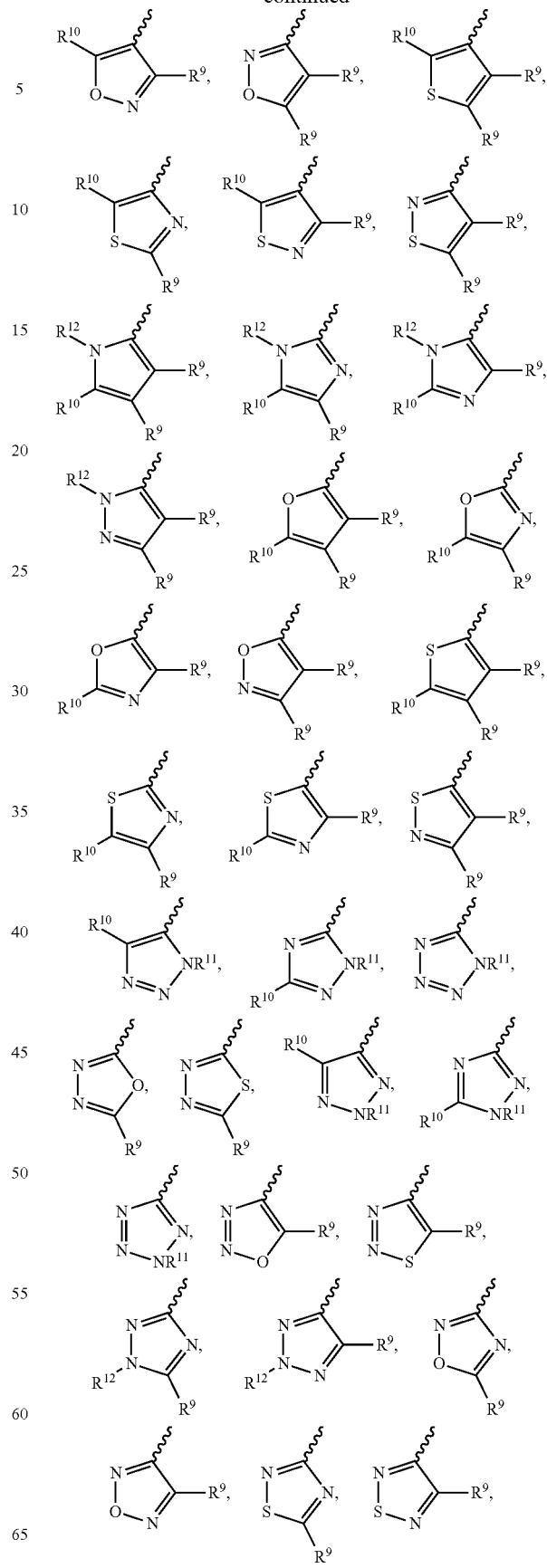

-continued

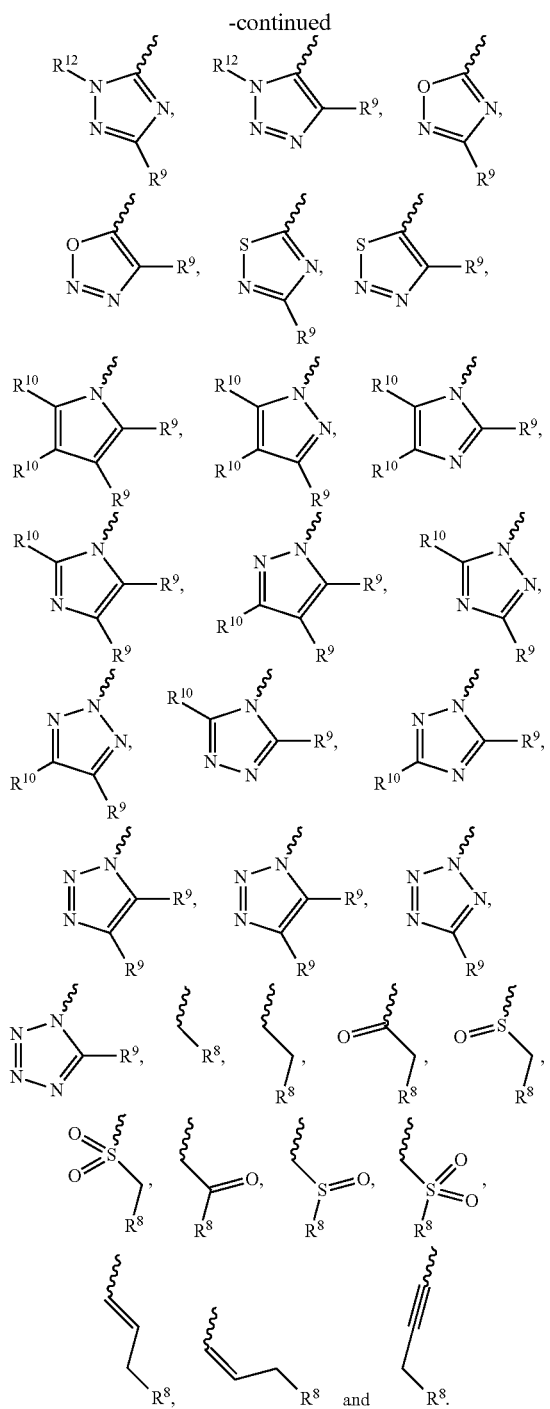

As defined generally above, each of $R^2$, $R^3$, $R^4$, $R^5$, $R^6$ and $R^7$ is independently selected from the group consisting of hydrogen, halogen, —CN, —CF$_3$, —OR, —NR$_2$, —NO$_2$, —COOR, —CONR$_2$, and —R. In some embodiments both of $R^5$ and $R^6$ are hydrogen. In some embodiments $R^5$ is hydrogen and $R^6$ is selected from the group consisting of halogen, —CN, —CF$_3$, —OR, —NR$_2$, —NO$_2$, —COOR, —CONR$_2$, and —R. In some embodiments $R^6$ is hydrogen and $R^5$ is selected from the group consisting of halogen, —CN, —CF$_3$, —OR, —NR$_2$, —NO$_2$, —COOR, —CONR$_2$, and —R. In some embodiments both $R^5$ and $R^6$ are independently selected from the group consisting of halogen, —CN, —CF$_3$, —OR, —NR$_2$, —NO$_2$, —COOR, —CONR$_2$, and —R. In some embodiments $R^5$ is halogen. In some embodiments $R^5$ is —CN. In some embodiments $R^5$ is —OR. In some embodiments $R^5$ is —OH. In some embodiments $R^5$ is —NR$_2$. In some embodiments $R^5$ is —NO$_2$. In some embodiments $R^5$ is —COOR. In some embodiments $R^5$ is —CONR$_2$. In some embodiments $R^5$ is methoxy. In some embodiments $R^5$ is —R, wherein R is $C_{1-3}$ aliphatic optionally substituted by one or more fluorines. In some embodiments $R^5$ is methyl. In some embodiments $R^5$ is trifluoromethyl. In some embodiments $R^6$ is halogen. In some embodiments $R^6$ is —CN. In some embodiments $R^6$ is —OR. In some embodiments $R^6$ is —OH. In some embodiments $R^6$ is —NR$_2$. In some embodiments $R^6$ is —NO$_2$. In some embodiments $R^6$ is —COOR. In some embodiments $R^6$ is —CONR$_2$. In some embodiments $R^6$ is methoxy. In some embodiments $R^6$ is —R, wherein R is $C_{1-3}$ aliphatic optionally substituted by one or more fluorines. In some embodiments $R^6$ is methyl. In some embodiments $R^6$ is trifluoromethyl As defined generally above, each A is independently selected from the group consisting of a covalent bond, an optionally substituted methylene, an optionally substituted cis ethylene, an optionally substituted trans ethylene, an acetylene, C(O), S(O) and S(O)$_2$; wherein, if one A is an optionally substituted methylene, an optionally substituted cis ethylene, an optionally substituted trans ethylene, an acetylene, C(O), S(O) or S(O)$_2$, the other must be a covalent bond or an optionally substituted methylene.

As defined generally above, $R^8$ is selected from the group consisting of hydrogen, NH$_2$, guanidino, 4-7 membered optionally substituted saturated heterocyclic ring having 1-2 heteroatoms independently selected from nitrogen, oxygen and sulfur, and 5-6 membered heteroaromatic ring having 1-2 heteroatoms independently selected from sulfur, nitrogen and oxygen. In some embodiments $R^8$ is hydrogen. In some embodiments $R^8$ is NH$_2$. In some embodiments $R^8$ is guanidine. In some embodiments $R^8$ is a 4-7 membered optionally substituted saturated heterocyclic group having 1-2 heteroatoms independently selected from nitrogen, oxygen and sulfur. In some embodiments $R^8$ is piperazino. In some embodiments, $R^8$ is piperidino. In some embodiments $R^8$ is a 5-6 membered heteroaromatic ring having 1-2 heteroatoms independently selected from sulfur, nitrogen and oxygen. In some embodiments, $R^8$ is imidazolo.

As defined generally above, each W is independently N or $CR^9$.

As defined generally above, each X is independently N or $CR^{10}$.

As defined generally above, Y is O, S or NR$^{11}$. In some embodiments, Y is O. In some embodiments, Y is S. In some embodiments, Y is NR$^{11}$.

As defined generally above, Z is O, S or NR$^{12}$. In some embodiments, Z is O. In some embodiments, Z is S. In some embodiments, Z is NR$^{12}$.

As defined generally above, $R^9$ is selected from the group consisting of hydrogen, L-R$^{13}$, NH$_2$, guanidino, 4-7 membered optionally substituted saturated heterocyclic ring having 1-2 heteroatoms independently selected from nitrogen, oxygen and sulfur, and 5-6 membered heteroaromatic ring having 1-2 heteroatoms independently selected from sulfur, nitrogen and oxygen; wherein, when one $R^9$ group is present, $R^9$ cannot be hydrogen and when two $R^9$ groups are present, one must be hydrogen and the other must not be hydrogen. In some embodiments $R^9$ is hydrogen. In some embodiments $R^9$ is L-R$^{13}$. In some embodiments $R^9$ is NH$_2$. In some embodiments $R^9$ is guanidine. In some embodiments $R^9$ is a 4-7 membered optionally substituted saturated heterocyclic group having 1-2 heteroatoms independently selected from nitrogen, oxygen and sulfur. In some embodiments $R^9$ is piperazino. In some embodiments, $R^9$ is piperidino. In some embodiments $R^9$ is a 5-6 membered heteroaromatic ring having 1-2 heteroatoms independently selected from sulfur, nitrogen and oxygen. In some embodiments, $R^9$ is imidazolo.

As defined generally above, each $R^{10}$ is independently selected from the group consisting of hydrogen, halogen, —CN, —CF$_3$, —OR, —NR$_2$, —NO$_2$, —COOR, —CONR$_2$, and —R.

As defined generally above, $R^H$ is selected from the group consisting of hydrogen, NH$_2$, guanidino, 4-7 membered optionally substituted saturated heterocyclic ring having 1-2 heteroatoms independently selected from nitrogen, oxygen and sulfur, and 5-6 membered heteroaromatic ring having 1-2 heteroatoms independently selected from sulfur, nitrogen and oxygen. In some embodiments $R^{11}$ is hydrogen. In some embodiments $R^{11}$ is NH$_2$. In some embodiments $R^{11}$ is guanidine. In some embodiments $R^{11}$ is a 4-7 membered optionally substituted saturated heterocyclic group having 1-2 heteroatoms independently selected from nitrogen, oxygen and sulfur. In some embodiments $R^{11}$ is piperazino. In some embodiments, $R^{11}$ is piperidino. In some embodiments $R^{11}$ is a 5-6 membered heteroaromatic ring having 1-2 heteroatoms independently selected from sulfur, nitrogen and oxygen. In some embodiments, $R^{11}$ is imidazolo.

As defined generally above, $R^{12}$ is hydrogen or optionally substituted C$_{1-6}$ aliphatic. In some embodiments, $R^{12}$ is hydrogen. In some embodiments, $R^{12}$ is an optionally substituted C$_{1-6}$ aliphatic.

As defined generally above, L is a covalent bond or a straight or branched C$_{1-6}$ aliphatic group, wherein one or more methylene groups are independently and optionally replaced by —NR$^{14}$— or —O—. In some embodiments, L is a covalent bond. In some embodiments, L is a straight or branched C$_{1-6}$ aliphatic group, wherein one or more methylene groups are independently and optionally replaced by —NR$^{14}$— or —O—. As defined generally above, $R^{13}$ is selected from the group consisting of NH$_2$, guanidino, 4-7 membered optionally substituted saturated heterocyclic ring having 1-2 heteroatoms independently selected from nitrogen, oxygen or sulfur, and 5-6 membered heteroaromatic ring having 1-2 heteroatoms independently selected from sulfur, nitrogen and oxygen. In some embodiments, $R^{13}$ is NH$_2$. In some embodiments, $R^{13}$ is guanidine. In some embodiments, $R^{13}$ is a 4-7 membered optionally substituted saturated heterocyclic ring having 1-2 heteroatoms independently selected from nitrogen, oxygen or sulfur. In some embodiments, said 4-7 membered optionally substituted saturated heterocyclic ring is azetadinyl, pyrrolidinyl, piperidinyl, piperazinyl, morpholinyl, hexamethyleneiminyl or homopiperazinyl. In some embodiments, $R^{13}$ is a 5-6 membered heteroaromatic ring having 1-2 heteroatoms independently selected from sulfur, nitrogen and oxygen. In some embodiments, said 5-6 membered heteroaromatic ring is pyrrolyl, thienyl, furanyl, imidazolyl, pyrazolyl, 1,2,3-triazolyl, 1,2,4-triazolyl, oxazolyl, isoxazolyl, thiazolyl, isothiazolyl, pyridinyl, and pyrazylyl.

As defined generally above, each $R^{14}$ is independently hydrogen or C$_{1-3}$ aliphatic. In some embodiments, each $R^{14}$ is hydrogen. In some embodiments, each $R^{14}$ is C$_{1-3}$ aliphatic. In some embodiments, each $R^{14}$ is independently hydrogen or C$_{1-3}$ aliphatic. In some embodiments, when more than one each $R^{14}$ is present, at least one $R^{14}$ is hydrogen. In some embodiments, when more than one each $R^{14}$ is present, at least one $R^{14}$ is C$_{1-3}$ aliphatic.

As defined generally above, each R is independently hydrogen or optionally substituted C$_{1-6}$ aliphatic.

In certain embodiments, the present invention provides a compound of formula I wherein $R^2$, $R^3$, $R^4$, and $R^7$ are each hydrogen, thereby forming a compound of formula I-a:

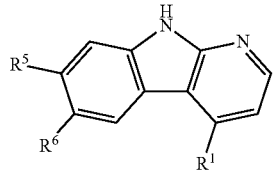

I-a or a pharmaceutically acceptable salt thereof, wherein each of $R^1$, $R^5$, and $R^6$ is defined above and described in embodiments herein, both singly and in combination.

In certain embodiments, the present invention provides a compound of formula I-a wherein $R^1$ is

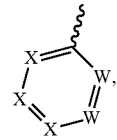

thereby forming a compound of formula II:

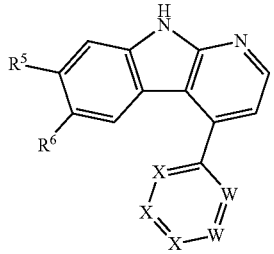

II or a pharmaceutically acceptable salt thereof, wherein each of $R^5$, $R^6$, W, and X is defined above and described in embodiments herein, both singly and in combination.

In certain embodiments, the present invention provides a compound of formula I-a wherein $R^1$ is

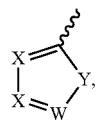

thereby forming a compound of formula III:

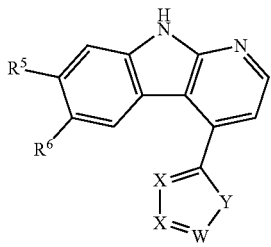

III or a pharmaceutically acceptable salt thereof, wherein each of $R^5$, $R^6$, W, X, and Y is defined above and described in embodiments herein, both singly and in combination.

In certain embodiments, the present invention provides a compound of formula I-a wherein $R^1$ is

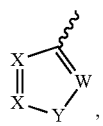

thereby forming a compound of formula IV:

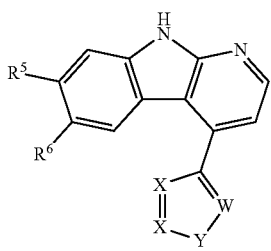

IV or a pharmaceutically acceptable salt thereof, wherein each of $R^5$, $R^6$, W, X, and Y is defined above and described in embodiments herein, both singly and in combination.

In certain embodiments, the present invention provides a compound of formula I-a wherein $R^1$ is

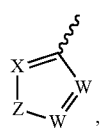

thereby forming a compound of formula V:

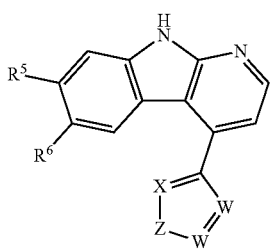

V or a pharmaceutically acceptable salt thereof, wherein each of $R^5$, $R^6$, W, X, and Z is defined above and described in embodiments herein, both singly and in combination.

In certain embodiments, the present invention provides a compound of formula I-a wherein $R^1$ is

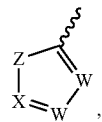

thereby forming a compound of formula VI:

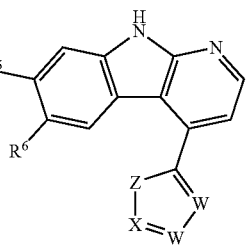

VI or a pharmaceutically acceptable salt thereof, wherein each of $R^5$, $R^6$, W, X, and Z is defined above and described in embodiments herein, both singly and in combination.

In certain embodiments, the present invention provides a compound of formula I-a wherein $R^1$ is

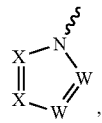

thereby forming a compound of formula VII:

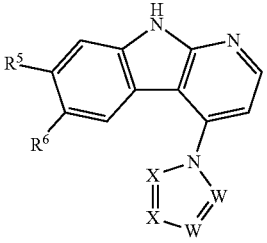

VII or a pharmaceutically acceptable salt thereof, wherein each of $R^5$, $R^6$, W, and X is defined above and described in embodiments herein, both singly and in combination.

In certain embodiments, the present invention provides a compound of formula I-a wherein $R^1$ is

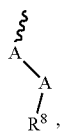

thereby forming a compound of formula VIII:

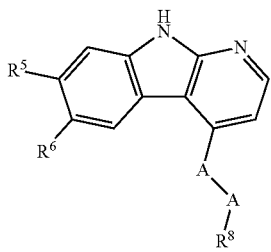

VIII or a pharmaceutically acceptable salt thereof, wherein each of $R^5$, $R^6$, $R^8$, and A is defined above and described in embodiments herein, both singly and in combination.

In certain embodiments, the present invention provides a method for the preparation of a compound of Formula I-a comprising the steps of
1) reacting a compound of the formula:

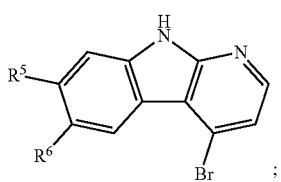

wherein $R^5$ and $R^6$ are defined as above;
with a compound selected from the list of structures consisting of:

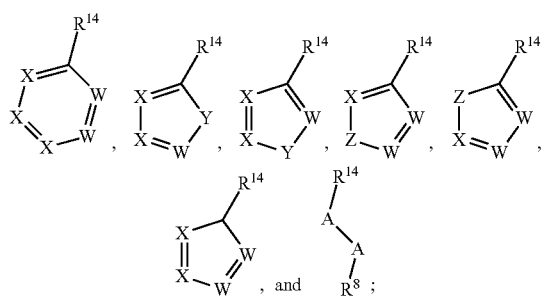

wherein
$R^{14}$ is selected from the list consisting of hydrogen, boronic acid, boronic ester, cuprate, MgBr, MgCl, MgI, Li, Na, ZnBr, ZnCl and ZnI; wherein any of $R^8$, $R^9$ and $R^{11}$ may be modified with a protecting group; and
2) removing a protecting group.

One of ordinary skill in the art will recognize that it may often be useful to replace utilize an I-substituted compound rather than a Br-substituted compound (e.g., replacing a structure of formula

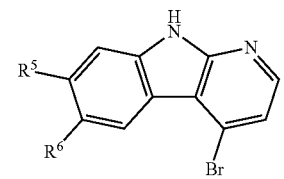

with a structure of formula

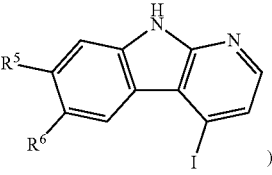

in executing the syntheses of compounds of this invention.

One of ordinary skill in the art will recognize that, in many embodiments, certain alternate synthetic strategies may be available for preparation of compounds of the present invention. Exemplary such alternative strategies include, but are not limited to, stepwise introduction of separate ring systems utilizing Suzuki, Ullman or Buchwald chemistry, direct synthesis of ring systems utilizing click chemistry, conversion of the starting bromide to a nucleophile (organolithium, Grignard, organozinc, cuprate, etc.) and displacing a leaving group from a ring system or acyclic group., or introduction of a substituted ethylene group via a Mizoroki-Heck reaction Exemplary compounds of formula I are set forth in Table 2, below:

TABLE 2

| Exemplary Compounds of Formula I | |
|---|---|
| Compound ID | Compound Structure |
| 9a | 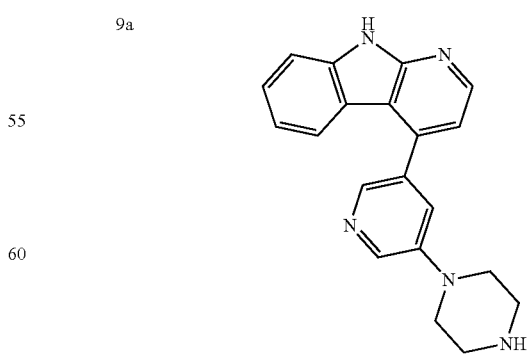 |

TABLE 2-continued
Exemplary Compounds of Formula I
| Compound ID | Compound Structure |
|---|---|
| 9b | 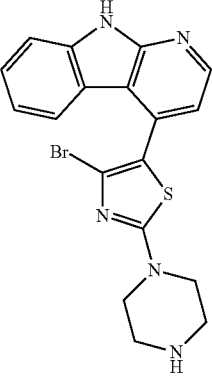 [SMILES: Brc1nc(N2CCNCC2)sc1-c1ccnc2[nH]c3ccccc3c12] |
| 9c | 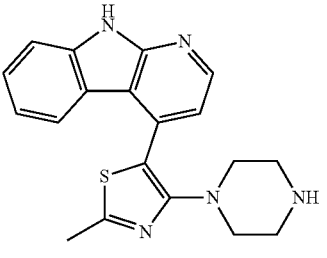 [SMILES: Cc1nc(N2CCNCC2)c(-c2ccnc3[nH]c4ccccc4c23)s1] |
| 9d | 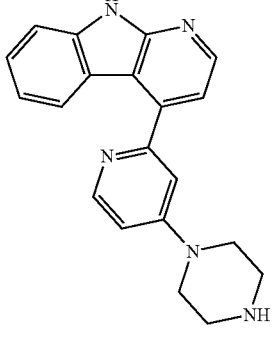 |
| 9e | 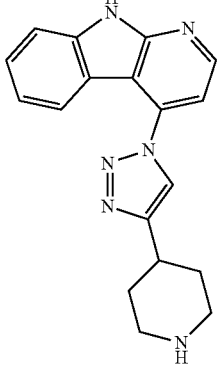 |
| 9f | 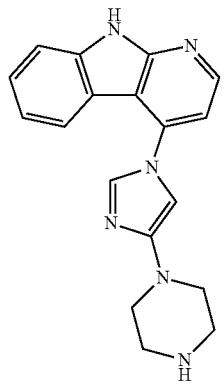 [SMILES: c1ccc2c(c1)[nH]c1nccc(-n3cnc(N4CCNCC4)c3)c12] |
| 9g | 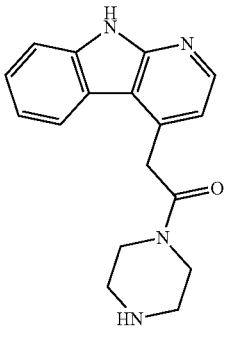 [SMILES: O=C(Cc1ccnc2[nH]c3ccccc3c12)N1CCNCC1] |
| 9h | 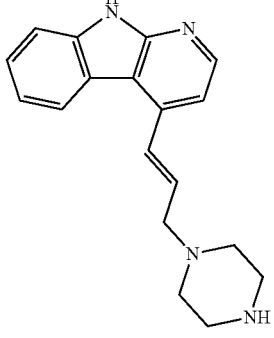 |
| 9j | 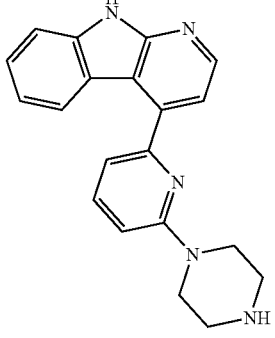 |

TABLE 2-continued
Exemplary Compounds of Formula I
| Compound ID | Compound Structure |
| --- | --- |
| 9k | 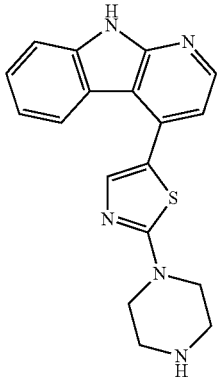 [SMILES: c1ccc2c(c1)[nH]c1nccc(-c3cnc(N4CCNCC4)s3)c12] |
| 9l | 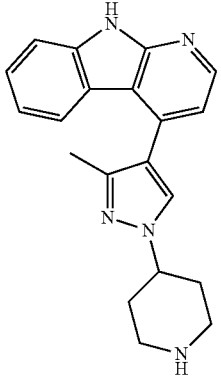 [SMILES: Cc1nn(C2CCNCC2)cc1-c1ccnc2[nH]c3ccccc3c12] |
| 9m | 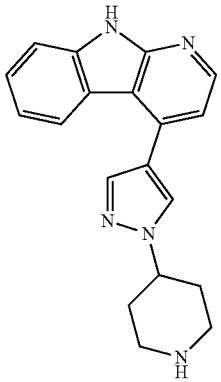 [SMILES: c1ccc2c(c1)[nH]c1nccc(-c3cnn(C4CCNCC4)c3)c12] |
| 9n | 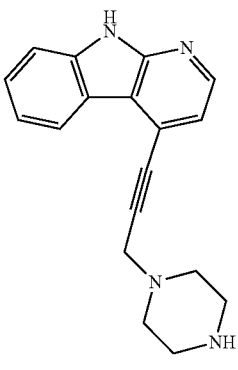 [SMILES: C(#Cc1ccnc2[nH]c3ccccc3c12)CN1CCNCC1] |
| 9o | 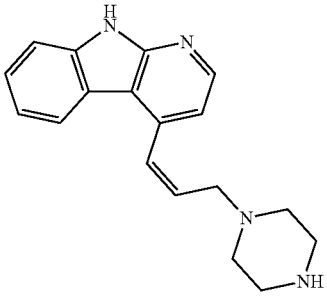 [SMILES: C(=C/c1ccnc2[nH]c3ccccc3c12)/CN1CCNCC1] |
| 9p | 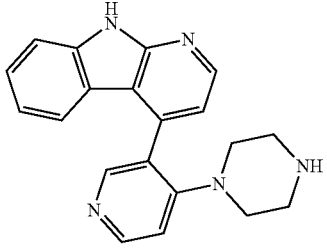 [SMILES: c1ccc2c(c1)[nH]c1nccc(-c3cnccc3N3CCNCC3)c12] |
| 9q | 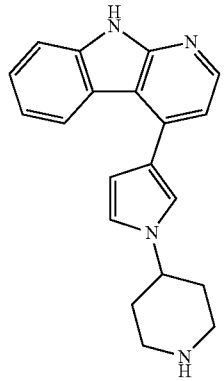 [SMILES: c1ccc2c(c1)[nH]c1nccc(-c3ccn(C4CCNCC4)c3)c12] |
| 9r | 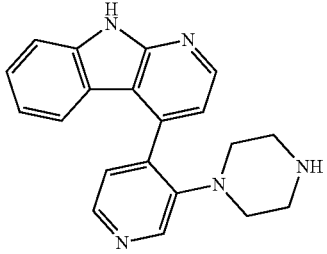 [SMILES: c1ccc2c(c1)[nH]c1nccc(-c3ccncc3N3CCNCC3)c12] |

TABLE 2-continued

Exemplary Compounds of Formula I

| Compound ID | Compound Structure |
|---|---|
| 9s | 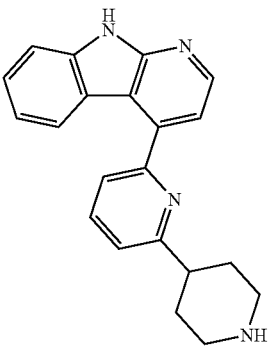 |
| 9t | 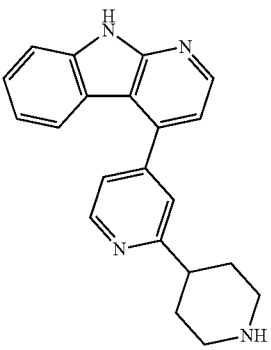 [SMILES: c1ccc2c(c1)[nH]c1nccc(-c3ccnc(C4CCNCC4)c3)c12] |
| 9u | 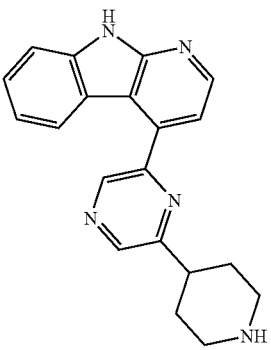 [SMILES: c1ccc2c(c1)[nH]c1nccc(-c3cncc(C4CCNCC4)n3)c12] |
| 9v | 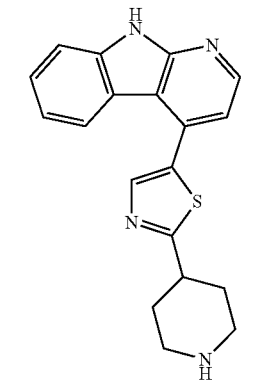 [SMILES: c1ccc2c(c1)[nH]c1nccc(-c3cnc(C4CCNCC4)s3)c12] |
| 9w | 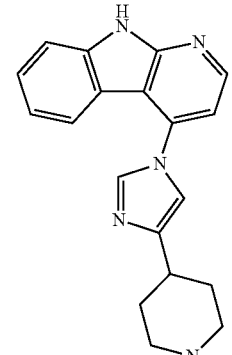 |
| 9x | 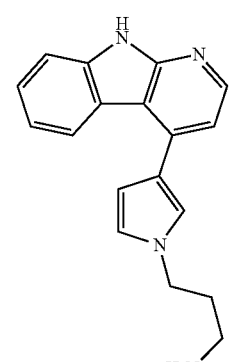 |
| 9y | 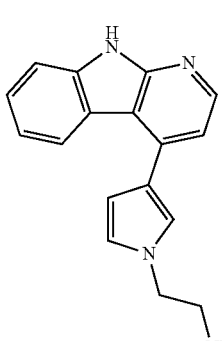 |

In certain embodiments, the present invention provides any compound selected from those depicted in Table 2, above, or a pharmaceutically acceptable salt thereof.

Compounds or salts thereof provided by the present invention may be utilized in any of a variety of forms. For example, in some embodiments, provided compounds (or salts thereof) are utilized in a solid form; in some such embodiments, provided compounds (or salts thereof) are utilized in an amorphous solid form. In some embodiments, provided compounds are utilized in a crystalline solid form. In some embodiments, provided compounds (or salts thereof) are utilized in a solid form (e.g., a crystalline solid form) that is a solvate or hydrate.

4. Uses, Formulation and Administration and Pharmaceutically Acceptable Compositions According to some embodiments, the invention provides a composition comprising a compound of this invention or a pharmaceutically acceptable derivative thereof and a pharmaceutically acceptable carrier, adjuvant, or vehicle.

In certain embodiments, the invention provides compositions containing an amount of compound effective to measurably inhibit CaMKII, in a biological sample or in a patient. In certain embodiments, the amount of compound in compositions of this invention is such that is effective to measurably inhibit a CaMKII mediated biological process in a biological sample or in a patient. In certain embodiments, provided compositions contain a unit dose amount of a compound described herein, wherein administration of such unit dose amount as part of a therapeutic regimen correlates with a desired pharmacologic and/or therapeutic outcome.

In certain embodiments, a composition of this invention is formulated for administration to a patient in need of such composition. In some embodiments, a composition of this invention is formulated for oral administration to a patient.

As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

The term "patient," as used herein, means an animal, often a mammal, and in many embodiments a human.

The term "pharmaceutically acceptable carrier, adjuvant, or vehicle", as used herein, refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, or salt of an ester of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of CaMKII or is retains therapeutic activity in treating the same disease, disorder or condition.

Compositions of the present invention may be formulated for any appropriate route of administration. For example, in some embodiments, provided compositions may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, provided compositions are administered orally, intraperitoneally or intravenously. Sterile injectable forms of the compositions of this invention may be aqueous or oleaginous suspension. Such suspensions may be formulated according to techniques known in the art using suitable dispersing or wetting agents and suspending agents.

In some embodiments, pharmaceutically acceptable compositions of the invention may be formulated as injectable preparations. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In some embodiments, injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In some embodiments, for example in order to prolong effects of a compound or composition, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively or additionally, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In some embodiments, sterile injectable preparations may be or include a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. Such oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

In some embodiments, provided compounds can be in micro-encapsulated form with one or more excipients as noted above. Solid dosage forms such as tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively or additionally, pharmaceutically acceptable compositions of this invention may be administered in the form of suppositories for rectal administration. Such compositions can be prepared by combining a provided compound with a suitable non-irritating excipient that is solid at room temperature but liquid at rectal temperature and therefore will melt in the rectum to release the drug. Such materials include cocoa butter, beeswax and polyethylene glycols.

In some embodiments, pharmaceutically acceptable compositions of this invention may be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively or additionally, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively or additionally, for ophthalmic uses, the pharmaceutically acceptable compositions may be formulated in an ointment such as petrolatum.

In some embodiments, pharmaceutically acceptable compositions of this invention may be administered by nasal aerosol or inhalation. Such compositions may be prepared according to techniques well-known in the art of pharmaceutical formulation, for example as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration. Such formulations may be administered with or without food. In some embodiments, pharmaceutically acceptable compositions of this invention are administered without food. In some embodiments, pharmaceutically acceptable compositions of this invention are administered with food.

The amount of compounds of the present invention that may be combined with the carrier materials to produce a composition in a single dosage form will vary depending upon the host treated, the particular mode of administration. In some embodiments provided compositions are formulated so that a dosage of between 0.01-100 mg/kg body weight/day of the inhibitor can be administered to a patient receiving these compositions.

It should also be understood that a specific dosage and treatment regimen for any particular patient may depend upon a variety of factors, including the activity of the specific compound employed, the age, body weight, general health, sex, diet, time of administration, rate of excretion, drug combination, and the judgment of the treating physician and the severity of the particular disease being treated. In some embodiments, amount of a compound of the present invention included in a composition described herein is determined by activity and/or bioavailability of the particular compound, so that compositions of different compounds may include different absolute amounts of compound.

Uses of Compounds and Pharmaceutically Acceptable Compositions

Compounds and compositions described herein are useful in the treatment of any of a variety of diseases, disorders, and conditions. In some embodiments, provided compounds and compositions are useful in the treatment of diseases, disorders, or conditions associated with activity of CaMKII.

$Ca^{2+}$/calmodulin-dependent protein kinase (CaMKII) is a serine/threonine kinase. Several lines of evidence strongly support the concept of direct inhibition of CaMKII activity as an important therapeutic target for treating a range of diseases including cardiovascular diseases such as atrial fibrillation, ventricular arrhythmia, heart failure, cardiac hypertrophy, atherosclerosis, and in-stent restenosis in coronary artery disease; use in cardioprotection; inflammatory lung diseases such as asthma; neurological diseases and conditions such as pain, stroke, ischemia, hypoxia, opioid tolerance and dependence, and macular degeneration; metabolic disorders such as type II diabetes, insulin resistance, and obesity; cancer and other proliferative disorders, such as osteosarcoma, melanoma, and prostate cancer; bone diseases such as osteoporosis; and inflammatory diseases such as rheumatoid arthritis.

Pharmacological and genetic inhibition of CaMKII reduces ryanodine receptor-mediated calcium leaks and blocked induction of atrial fibrillation in a mouse model of atrial fibrillation. In atrial cells from atrial fibrillation patients CaMKII activity is increased leading to calcium leaks that promote atrial fibrillation, while inhibition of the kinase reduces the calcium leak. (Dobrev D, et al., "Novel molecular targets for atrial fibrillation therapy" (2012) *Nature Reviews Drug Discovery* 11:275-291; Chelu M G, et al., "Calmodulin kinase II-mediated sarcoplasmic reticulum Ca2+ leak promotes atrial fibrillation in mice" (2009) *J Clin Invest* 119:1940-1951; Neef S, et al., "CaMKII-dependent diastolic SR $Ca^{2+}$ leak and elevated diastolic $Ca^{2+}$ levels in right atrial myocardium of patients with atrial fibrillation" (2010) *Circ Res* 106:1134-1144).

Pharmacological inhibition of CaMKII is shown to reduce cardiac arrhythmogenesis in vitro and in vivo, including inhibition of torsades that lead to sudden death. (Anderson M E, et al., "KN-93, an inhibitor of multifunctional $Ca^{++}$/Calmodulin-dependent protein kinase, decreases early afterdepolarizations in rabbit heart" (1998) *J Pharmacol Exp Ther* 287:996-1006; Sag C M, et al., "Calcium/calmodulin-dependent protein kinase II contributes to cardiac arrhythmogenesis in heart failure" (2009) *Circ Heart Fail* 2:664-675; Erickson J R, Anderson M E, "CaMKII and Its role in cardiac arrhythmia" (2008) *Journal of Cardiovascular Electrophysiology* 19:1332-1336). CaMKII integrates several proarrhythmic pathways that augment CaMKII activity via Ca2+ and reactive oxygen species and which, in turn, acts on the ryanodine receptor, the voltage-dependent calcium channel (Cav1.2), and the Na channel (Nav1.5) to promote arrhythmia (Rokita A G and Anderson M E "New Therapeutic Targets in Cardiology Arrhythmias and Ca2+/Calmodulin-Dependent Kinase II (CaMKII)" (2012) *Circulation* 126:2125-2139).

Studies implicate CaMKII in heart failure and structural heart disease in both mouse models and human heart tissue. Pharmacological and genetic-based inhibition of CaMKII was shown to protect cellular mechanical function and preserves calcium homeostasis after myocardial infarction. CaMKII is increased in cells from failing human heart cells and its pharmacological inhibition improves contractility by an established CaMKII pathway. (Schulman H, Anderson M E, "Ca/Calmodulin-dependent Protein Kinase II in Heart Failure" (2010) *Drug Discovery Today: Disease Mechanisms* 7:e117-e122; Zhang R, et al., "Calmodulin kinase II inhibition protects against structural heart disease" (2005) *Nat Med* 11:409-417; Sossalla S, et al., "Inhibition of Elevated Ca2+/Calmodulin-Dependent Protein Kinase II Improves Contractility in Human Failing Myocardium" (2010) *Circulation Research* 107:1150-1161).

Genetic activation and pharmacological inhibition of CaMKII were used to show that CaMKII mediates cardiac hypertrophy while genetic deletion of δ-CaMKII protected the heart from pathological cardiac hypertrophy and remodeling after pressure overload. (Backs J, et al., "The delta isoform of CaM kinase II is required for pathological cardiac hypertrophy and remodeling after pressure overload" (2009) *Proc Natl Acad Sci USA* 106:2342-2347; Zhang T, et al., "The cardiac-specific nuclear delta(B) isoform of $Ca^{2+}$/calmodulin-dependent protein kinase II induces hypertrophy and dilated cardiomyopathy associated with increased protein phosphatase 2A activity" (2002) *J Biol Chem* 277:1261-1267; Anderson M E, et al., "CaMKII in myocardial hypertrophy and heart failure" (2011) *Journal of Molecular and Cellular Cardiology* 51:468-473).

CaMKII inhibition is found to be effective in several forms of cardioprotection, including from cardiotoxicity caused by cancer therapy (doxorubicin), following heart attack or ischemia-reperfusion, e.g. for the case of acute intervention for heart attack (primary angioplasty), and for patients with mutations leading to sudden death, such as catecholaminergic polymorphic ventricular tachycardia. (Sag C M, et al., "CaMKII-dependent SR Ca leak contributes to doxorubicin-induced impaired Ca handling in isolated cardiac myocytes" (2011) *Journal of Molecular and Cellular Cardiology* 51:749-759; Zhang R, et al., "Calmodulin kinase II inhibition protects against structural heart disease" (2005) *Nat Med* 11:409-417; Liu N, et al., "Calmodulin kinase II inhibition prevents arrhythmias in RyR2 (R4496C+/−) mice with catecholaminergic polymorphic ventricular tachycardia" (2011) *Journal of Molecular and Cellular Cardiology* 50:214-222; Joiner, M-L A, et al., "CaMKII determines mitochondrial stress responses in heart" (2012). *Nat Med, DOI:* 10.1038/nature11444, published online Oct. 10, 2012).

Atherosclerosis pathology includes both the constriction of the vasculature as well as plaque disruption. CaMKII inhibition blocks proliferation of vascular cells as well as mediating ER stressors that lead to apoptosis that underlie plaque disruption. (Timmins J M, et al., "Calcium/calmodulin-dependent protein kinase II links ER stress with Fas and mitochondrial apoptosis pathways" (2009) *The Journal of Clinical Investigation* 119:2925-2941; Li W, et al., "The multifunctional Ca2+/calmodulin-dependent kinase 116 (CaMKII6) controls neointima formation after carotid ligation and vascular smooth muscle cell proliferation through cell cycle regulation by p21" (2011) *J Biol Chem* 286:7990-7999).

Studies suggest that CaMKII is an important, but previously unrecognized pro-asthmatic signal, linking the pro-oxidant environment of the asthmatic airways with downstream inflammatory and remodeling events. CaMKII activity in the epithelium may be required for enhancing eosinophilic recruitment to the lung, through a ROS-CaMKII-eotaxin-1 dependent pathway. Inhibition of CaMKII activity may be a novel target in future asthma therapies. (Sanders P N, et al., "Camkii As A Pro-Asthmatic Signal" (2011) *Am J Respir Care Med* 183:A2795, May 6, 2011 poster presentation).

Smooth muscle proliferation contributes to vascular remodeling and obstructive vasculopathies such as atherosclerosis and restenosis following percutaneous coronary interventions and inhibition of the kinase blocks vascular smooth muscle proliferation and neointimal formation that lead to restenosis. (Li W, et al., "The multifunctional Ca2+/calmodulin-dependent kinase 11δ (CaMKIIδ) controls neointima formation after carotid ligation and vascular smooth muscle cell proliferation through cell cycle regulation by p21" (2011) *J Biol Chem* 286:7990-7999; House S J, Singer H A, "CaMKII-delta isoform regulation of neointima formation after vascular injury" (2008) *Arterioscler Thromb Vasc Biol* 28:441-447).

Pharmacological and genetic suppression of CaMKII has been used to demonstrate a reduction in central and peripheral pain due to injury or inflammation as well as in sensitization to pain. (Zeitz K P, et al., "The contribution of autophosphorylated alpha-calcium-calmodulin kinase II to injury-induced persistent pain" (2004) *Neuroscience* 128:889-898; Luo F, et al., "Reversal of chronic inflammatory pain by acute inhibition of Ca2+/calmodulin-dependent protein kinase II" (2008) *J Pharmacol Exp Ther* 325:267-275; Chen Y, et al., "$Ca^{2+}$/Calmodulin-dependent protein kinase IIα is required for the initiation and maintenance of opioid-induced hyperalgesia" (2010) *J Neurosci* 30:38-46; Crown E D, et al., "Calcium/calmodulin dependent kinase II contributes to persistent central neuropathic pain following spinal cord injury" (2012) *Pain* 153:710-721).

Inhibition of CaMKII is neuroprotective, reducing damage due to hypoxia in stroke models. Reduction of atrial fibrillation by Inhibition of CaMKII would also reduce stroke incidence. (Vest R S, et al., "Effective post-insult neuroprotection by a novel CaMKII inhibitor" (2010) *J Biol Chem* 285:20675-20682; Ashpole N M, et al., "Calcium/Calmodulin-dependent Protein Kinase II (CaMKII) Inhibition Induces Neurotoxicity via Dysregulation of Glutamate/Calcium Signaling and Hyperexcitability" (2012) *Journal of Biological Chemistry* 287:8495-8506; Dobrev D, et al., "Novel molecular targets for atrial fibrillation therapy" (2012) *Nature Reviews Drug Discovery* 11:275-291).

Stimulation of opiate receptors increases CaMKII and leads to tolerance and dependence that are reduced by inhibition of CaMKII. (Liang D, et al., "Increased expression of Ca2+/calmodulin-dependent protein kinase II alpha during chronic morphine exposure" (2004) *Neuroscience* 123:769-775; Fan G H, et al., "Inhibition of calcium/calmodulin-dependent protein kinase II in rat hippocampus attenuates morphine tolerance and dependence" (1999) *Mol Pharmacol* 56:39-45).

The beta isoform of CaMKII is selectively increased in the lateral habenula, a region associated with pathophysiology of depression, is up-regulated in a preclinical model of depression and down-regulated by treatment with anti-depressant drugs (Li K, et al., βCaMKII in lateral habenula mediates core symptoms of depression" (2013) *Science* 341:1016-1020). A selective elevation of the beta isoform increased core depressive symptoms, such as anhedonia and behavioral despair, while genetic suppression of the beta isoform reversed the depressive symptoms.

Inhibition of CaMKII reduces the VEGF pathway that mediates increased vascularization or angiogenesis of retinal endothelial cells. (Banumathi E, et al., "VEGF-induced retinal angiogenic signalling is critically dependent on Ca2+ signalling via Ca2+/calmodulin-dependent protein kinase II" (2011) *Investigative Ophthalmology & Visual Science* 52:3103-3111).

CaMKII may have several sites of action that support the notion of CaMKII inhibition in type II diabetes. CaMKII modulates insulin signaling that suggest a role in the pathogenesis of insulin resistance. In liver, CaMKII regulates glucose production and suppression of insulin signaling and thus its inhibition would be beneficial in diabetes and cardiometabolic disease. (Illario M, et al., "Calcium-calmodulin-dependent kinase II (CaMKII) mediates insulin-stimulated proliferation and glucose uptake" (2009) *Cellular Signalling* 21:786-792; Ozcan L, et al., "Calcium Signaling through CaMKII Regulates Hepatic Glucose Production in Fasting and Obesity" (2012) *Cell Metabolism* 15:739-751; Ozcan L, et al., Activation of Calcium/Calmodulin-dependent Protein Kinase II in obesity mediates suppression of hepatic insulin signaling" (2013) *Cell Metabolism* 18: 1-13).

Studies show that pharmacological inhibition of CaMKII reduces proliferation of osteosarcoma cell lines and indicates changes in signal transduction related to growth. The inhibitor administered to mice with a human osteosarcoma xenograft markedly decreases tumor size. (Yuan K, et al., "α-CaMKII controls the growth of human osteosarcoma by regulating cell cycle progression" (2007) *Lab Invest* 87:938-950).

Tumor necrosis factor-related apoptosis-inducing ligand (TRAIL) provides a pathway in melanoma therapy but melanoma is often resistant to TRAIL after metastasis. Inhibition of CaMKII signaling by use of a dominant negative form of the kinase was shown to restore the sensitivity of melanoma to cell death via TRAIL. (Xiao C, et al., "Inhibition of CaMKII-mediated c-FLIP expression sensitizes malignant melanoma cells to TRAIL-induced apoptosis" (2005) *Exp Cell Res* 304:244-255).

Studies have shown that proliferation and invasion of prostate cancer cell lines is reduced by pharmacological inhibition of CaMKII. Kinase inhibition was used to show that it is important for prostate cancer cell survival and promotes their progression to an androgen-independent state. (Mamaeva O A, et al., "Calcium/calmodulin-dependent kinase II regulates notch-1 signaling in prostate cancer cells" (2009) *J Cell Biochem* 106:25-32; Rokhlin O W, et al., "Calcium/calmodulin-dependent kinase II plays an important role in prostate cancer cell survival" (2007) *Cancer Biol Ther* 6:732-742).

Pharmacological inhibition of CaMKII reduces differentiation of osteoclasts and suppresses bone resorption characteristic of osteoporosis. (Ang E S M, et al., "Calcium/calmodulin-dependent kinase activity is required for efficient induction of osteoclast differentiation and bone resorption by receptor activator of nuclear factor kappa B ligand (RANKL)" (2007) *Journal of cellular physiology* 212:787-795).

Pharmacological and genetic suppression of CaMKII demonstrated its role in the production of proinflammatory cytokines and interferon in macrophages. A small molecule inhibitor of CaMKII was used to show that it required for tumour necrosis factor-related apoptosis inducing ligand (TRAIL)-mediated apoptosis of fibroblast-like synovial cells, suggesting that it is a target for rheumatoid arthritis therapy. (Liu X, et al., "CaMKII promotes TLR-triggered proinflammatory cytokine and type I interferon production by directly binding and activating TAK1 and IRF3 in macrophages" (2008) *Blood* 112:4961-4970; Fujikawa K, et al., "Calcium/calmodulin-dependent protein kinase II (CaMKII) regulates tumour necrosis factor-related apoptosis inducing ligand (TRAIL)-mediated apoptosis of fibroblast-like synovial cells (FLS) by phosphorylation of Akt" (2009) *Clinical and experimental rheumatology* 27:952-957).

The activity of a compound utilized in this invention as an inhibitor of CaMKII or treatment for a CaMKII-mediated disease, disorder or condition, may be assayed in vitro or in vivo. An in vivo assessment of the efficacy of the compounds of the invention may be made using an animal model of a CaMKII-mediated disease, disorder or condition, e.g., a rodent or primate model. Cell-based assays may be performed using, e.g., a cell line isolated from a tissue that expresses CaMKII. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the invention. Alternate or additional in vitro assays may be used to quantitate the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively or additionally, inhibitor binding may be determined by running a competition experiment where new inhibitors are incubated with purified proteins or nucleic acids bound to known radioligands. Detailed conditions of exemplary systems for assaying a compound utilized in this invention as an inhibitor of CaMKII are set forth in the Examples below. Such assays are exemplary and not intended to limit the scope of the invention. The skilled practitioner can appreciate that modifications can be made to conventional assays to develop equivalent or other assays that can be employed to comparably assess activity or otherwise characterize compounds and/or compositions as described herein.

As used herein, the terms "treatment," "treat," and "treating" refer to reversing, alleviating, delaying the onset of, reducing incidence or severity, or inhibiting the progress of a disease, disorder or condition, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Compounds and/or compositions described herein may be administered using any amount and any route of administration effective for treating a disease, disorder, or condition. In some embodiments, compounds and/or compostions are administered in an amount and/or by a route effective for treating a cardiovascular disease, disorder or condition, an inflammatory disease, disorder or condition, a neurological disease, disorder or condition, an ocular disease, disorder or condition, a metabolic disease, disorder or condition, a cancer or other proliferative disease, disorder or condition, a bone disease, disorder or condition, or an addictive disease, disorder, or condition.

In some embodiments, compounds and/or compositions described herein may be administered using any amount and any route of administration effective for treating or lessening the severity of a disease, disorder or condition associated with CaMKII.

In some embodiments, compounds and/or compositions may be administered using any amount and any route of administration effective for treating a cardiovascular disease, disorder, or condition. In some embodiments, the cardiovascular disease, disorder or condition is a disease of the heart. In some embodiments, the cardiovascular disease, disorder or condition is a disease of the vasculature. In some embodiments, the cardiovascular disease, disorder or condition is selected from atrial fibrillation, ventricular arrhythmia, heart failure, cardiac hypertrophy, atherosclerosis, or restenosis. In some embodiments the restenosis is in-stent restenosis in coronary artery disease.

In some embodiments, provided compounds and/or compositions may be administered using any amount and any route of administration effective for achieving cardioprotection from cardiotoxicity. In some embodiments, the cardiotoxicity avoided by administration of the compounds and compositions of the invention is due to drug therapy, heart attack, ischemia-reperfusion injury, or mutations leading to sudden death such as catecholaminergic polymorphic ventricular tachycardia.

In some embodiments, the compounds and compositions, according to the method of the present invention, may be administered using any amount and any route of administration effective for treating an inflammatory disease, disorder or condition. In some embodiments, the inflammatory disease, disorder or condition is asthma or rheumatoid arthritis.

In some embodiments, the compounds and compositions, according to the method of the present invention, may be administered using any amount and any route of administration effective for treating a neurological disease, disorder or condition. In some embodiments, the neurological disease, disorder or condition is pain or stroke.

In some embodiments, the compounds and compositions, according to the method of the present invention, may be administered using any amount and any route of administration effective for treating an addictive disease, disorder or condition. In some embodiments the addictive disease, disorder, or condition is opioid tolerance or dependence.

In some embodiments, the compounds and compositions, according to the method of the present invention, may be administered using any amount and any route of administration effective for treating an ocular disease, disorder or condition. In some embodiments, the ocular disease, disorder or condition is macular degeneration.

In some embodiments, the compounds and compositions, according to the method of the present invention, may be administered using any amount and any route of administration effective for treating a metabolic disease, disorder or condition. In some embodiments, the metabolic disease, disorder or condition is diabetes. In some embodiments, the diabetes is type II diabetes.

In some embodiments, the compounds and compositions, according to the method of the present invention, may be administered using any amount and any route of administration effective for treating a cancer or another proliferative disease, disorder or condition. In some embodiments, the cancer or other proliferative disease, disorder or condition is an osteosarcoma, a melanoma, or a prostate cancer.

In some embodiments, the compounds and compositions, according to the method of the present invention, may be administered using any amount and any route of administration effective for treating a bone disease, disorder or condition. In some embodiments, the bone disease, disorder or condition is osteoporosis.

In will be appreciated by those skilled in the art that the exact amount of a provided compound or composition may vary from subject to subject, depending on the species, age, and general condition of the subject, the severity of the infection, the particular agent, its mode of administration, and the like.

In some embodiments, compounds of the invention are formulated in dosage unit form, for example for ease of administration and uniformity of dosage. The expression "dosage unit form" or "unit dosage" as used herein refers to a physically discrete unit of agent appropriate for the patient to be treated. It will be understood, however, that total daily usage of the compounds and compositions of the present invention may be decided by the attending physician within the scope of sound medical judgment. The specific effective dose level for any particular patient or organism may depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

According to some embodiments, the invention relates to a method of inhibiting CaMKII in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Some embodiments of the present invention relate to a method of inhibiting CaMKII in a patient comprising the step of administering to said patient a compound of the present invention, or a composition comprising said compound.

In some embodiments, the invention relates to a method of inhibiting CaMKII activity in a patient comprising the step of administering to said patient a compound of the present invention, or a composition comprising said compound. In certain embodiments, the present invention provides a method for treating a disease, disorder or condition mediated by CaMKII, in a patient in need thereof, comprising the step of administering to said patient a compound according to the present invention or pharmaceutically acceptable composition thereof. Such diseases, disorders and conditions are described in detail herein.

In some embodiments compounds and/or compositions of the present invention may be used in a method of treating a cardiovascular disease, disorder, or condition, an inflammatory disease, disorder or condition, a neurological disease, disorder or condition, an ocular disease, disorder or condition, a metabolic disease, disorder or condition, a cancer or other proliferative disease, disorder or condition, or a bone disease, disorder or condition. In certain embodiments the compounds and compositions of the present invention may be used to treat a cardiovascular disease, disorder or condition, an inflammatory disease, disorder or condition, a neurological disease, disorder or condition, an ocular disease, disorder or condition, a metabolic disease, disorder or condition, a cancer or other proliferative disease, disorder or condition, or a bone disease, disorder or condition in a mammal. In certain embodiments the mammal is a human patient.

In some embodiments the present invention provides a method of treating a cardiovascular disease, disorder or condition, an inflammatory disease, disorder or condition, a neurological disease, disorder or condition, an ocular disease, disorder or condition, a metabolic disease, disorder or condition, a cancer or other proliferative disease, disorder or condition, or a bone disease, disorder or condition, comprising administering a compound or composition of the present invention to a patient in need thereof. In certain embodiments the method of treating a cardiovascular disease, disorder or condition, an inflammatory disease, disorder or condition, a neurological disease, disorder or condition, an ocular disease, disorder or condition, a metabolic disease, disorder or condition, a cancer or other proliferative disease, disorder or condition, or a bone disease, disorder or condition comprises administering compounds and compositions of the present invention to a mammal. In certain embodiments the mammal is a human.

In certain embodiments, the present invention provides a method of treating a cardiovascular disease, disorder or condition, comprising administering a compound or composition of the present invention to a patient with a cardiovascular disease, disorder or condition. In certain embodiments, the method of treating a cardiovascular disease, disorder or condition comprises administering compounds and compositions of the present invention to a mammal. In certain embodiments, the mammal is a human.

In certain embodiments, the present invention provides a method of treating a cancer or another proliferative disease, disorder or condition, comprising administering a compound or composition of the present invention to a patient with a cancer or another proliferative disease, disorder or condition. In certain embodiments, the method of treating a cancer or other proliferative disorder comprises administering compounds and compositions of the present invention to a mammal. In certain embodiments, the mammal is a human.

As used herein, the terms "treating a cancer" refers to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the compounds and compositions described herein and against which the methods described herein are useful include but are not limited to breast, prostate, brain, blood, bone marrow, bone, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by compounds or compositions of the invention is a skin cancer, lung cancer, breast cancer, prostate cancer, leukemia, kidney cancer, esophageal cancer, brain cancer, bone cancer or colon cancer. In some embodiments, the cancer treated by the compounds or compositions of the invention is an osteosarcoma, a melanoma or a prostate cancer.

In certain embodiments, the present invention provides a method of treating a neurological disease, disorder or condition, comprising administering a compound or composition of the present invention to a patient with a neurological disease, disorder or condition. In certain embodiments, the method of treating a neurological disease, disorder or condition comprises administering compounds and compositions of the present invention to a mammal. In certain embodiments, the mammal is a human. In certain embodiments, the neurological disease, disorder or condition is pain or stroke.

In certain embodiments, the present invention provides a method of treating an inflammatory disease, disorder or condition, comprising administering a compound or composition of the present invention to a patient with an inflammatory disease, disorder or condition. In certain embodiments, the method of treating an inflammatory disease, disorder or condition comprises administering compounds and compositions of the present invention to a mammal. In certain embodiments, the mammal is a human. In certain embodiments, the neurological disease, disorder or condition is asthma or rheumatoid arthritis.

In certain embodiments, the present invention provides a method of treating a metabolic disease, disorder or condition, comprising administering a compound or composition of the present invention to a patient with a metabolic disease, disorder or condition. In certain embodiments, the method of treating a metabolic disease, disorder or condition comprises administering compounds and compositions of the present invention to a mammal. In certain embodiments, the mammal is a human. In certain embodiments, the metabolic disease, disorder or condition is diabetes. In some embodiments, the diabetes is type II diabetes.

In certain embodiments, the present invention provides a method of treating opioid tolerance or dependence, comprising administering a compound or composition of the present invention to an opioid tolerant or dependent patient. with a metabolic disease, disorder or condition. In certain embodiments, the method of treating opioid tolerance or dependence comprises administering compounds and compositions of the present invention to a human. In some embodiments the opioid tolerance or dependence is morphine tolerance or dependence.

In certain embodiments, the present invention provides a method of treating an ocular disease, disorder or condition, comprising administering a compound or composition of the present invention to a patient with an ocular disease, disorder or condition. In certain embodiments, the method of treating an ocular disease, disorder or condition comprises administering compounds and compositions of the present invention to a mammal. In certain embodiments, the mammal is a human. In certain embodiments, the ocular disease, disorder or condition is macular degeneration.

Depending upon the particular disease, disorder or condition to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or composition thereof, is administered in combination with another inhibitor of CaMKII. In some embodiments, a provided compound, or composition thereof, is administered in combination with one or more other therapeutic agents. Such CaMKII inhibitors include, but are not limited to CaM Kinase II Calmodulin Antagonist peptide, KN-93, and lavendustin C.

In certain embodiments, a provided compound, or a composition thereof, is administered in combination with another anti-cancer, cytotoxin, or chemotherapeutic agent.

In certain embodiments, the anti-cancer or chemotherapeutic agents used in combination with compounds or compositions of the invention include, but are not limited to imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Oprapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, a combination of 2 or more therapeutic agents may be administered together with compounds of the invention. In certain embodiments, a combination of 3 or more therapeutic agents may be administered with compounds of the invention.

Other examples of agents the inhibitors of this invention may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), antiemetics (e.g. 5-HT$_3$ receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rcbif®), Copaxone®, and mitoxantrone; treatments for asthma such as albuterol and Singulair; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, compounds of the present invention, or a pharmaceutically acceptable composition thereof, are administered in combination with antisense agents, a monoclonal or polyclonal antibody or an siRNA therapeutic.

Those additional agents may be administered separately from an inventive compound-containing composition, as part of a multiple dosage regimen. Alternatively or in addition to those additional agents administered separately, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, I-a, II, III, IV, V, VI, VII or VIII, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

In certain embodiments, compounds of formula I-a are prepared from an intermediate structure of formula IX according to the procedure outlined in Scheme 1.

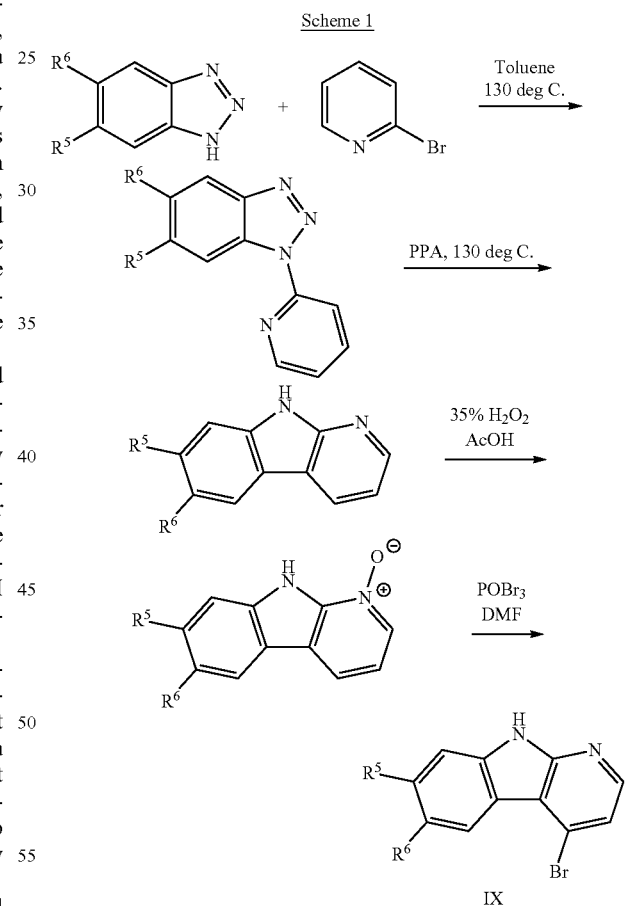

Subsequent elaboration of a compound of formula IX into exemplary structures of the present invention is accomplished using chemistry familiar to one skilled in the art. Such chemistry includes, but is not limited to, Suzuki coupling reacctions, Buchwald coupling reactions, Sonagashira coupling reactions, use of palladium catalysts, use of copper catalysts, use of "click" chemistry, use of zinc reagents, use of lithium reagents, use of Grignard reagents, use of protecting groups, use of methods for incorporating protecting groups and use of methods for removal of protecting groups. One of ordinary skill in the art will recognize that the specific methodologies required and the order in which said methodologies are employed depends on the specific substrates required for the preparation of any individual compound of the present invention.

In certain embodiments, compounds of formula I-a are prepared from an intermediate structure of formula IXa according to the procedure outlined in Scheme 2.

Scheme 2

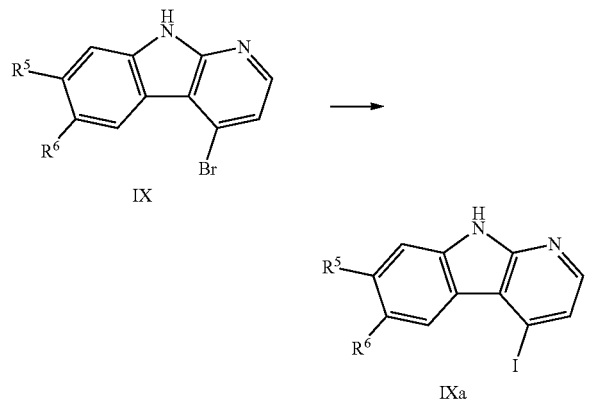

Acceptable methods for conversion of a compound of formula IX to a compound of formula IXa include, but are not limited to the following:

Heating in phenol with sodium iodide
Reacting with acetyl chloride and sodium iodide followed by hydrolysis of the acetate from the bridging nitrogen atom
Transient protection of the bridging NH with a silyl group followed by lithium-halogen exchange on treatment with tert-butyllithium and quenching with iodine The following examples illustrate methods utilized for the preparation of structures relevant to the present invention. Throughout these examples, certain equipment, HPLC columns and solvent systems are utilized in the execution of reactions and the purification of reaction products. Accordingly, microwave reactions are carried out utilizing an AntonPar, Monowave 300 microwave reactor. Preparative HPLC purifications are carried out utilizing a Shimadzu [Prominence LC-20AP], equipped with a Discovery C-18 column (50×21.2 mm, 5µ) utilizing the following method: Solvent A=Acetonitrile, Solvent B=Water; Gradient=95% solvent B to 10% solvent B over 20 min with a flow rate of 10 mL/min. Analytical LCMS data were acquired using a Shimadzu [LCMS-2020] equipped with a SHIMPAK, XR ODS-II column (50×2 mm) utilizing the following method: Flow Rate=0.2 mL/min, Solvent A=Acetonitrile, Solvent B=0.1% TFA in water; Gradient=Initial 95% of solvent B to 10% solvent B over 10 min followed by 10% solvent B for an additional 10 min.

It is understood that the chemistry presented in the following examples include individual reactions known to one skilled in the art. It is also understood that the specific combinations of reactions required to synthesize the intended structures either in part or in whole are not generally known to one skilled in the art. In support of the present invention, reactions and methodologies that support the synthesis of the novel compounds exemplified herein or the novel intermediate structures incorporated in the synthesis of the novel compounds exemplified herein are contained in the following references. It is understood that these references do not constitute the complete body of literature or methodologies employable in the preparation of the final compounds or intermediate structures described in the following examples. It is further understood that one skilled in the art will recognize that there are alternative chemistry methodologies that may be useful in execution of the synthetic schemes presented in said examples.

References supporting the synthesis of compounds described in Examples 1-9:

Jimenez, Juan-Miguel, PCT Int. Appl., 2010011768, 28 Jan. 2010

Panteleev, Jane et al, Advanced Synthesis & Catalysis, 350(18), 2893-2902; 2008

Pereira, Guilherme R. et al, European Journal of Medicinal Chemistry, 73, 295-309; 2014

Shevchuk, Nadiia V. et al, Synthesis, 44(13), 2041-2048; 2012

Duffy, Joseph L. et al PCT Int. Appl., 2010017048, 11 Feb. 2010

Hama, Takuo et al Journal of Organic Chemistry, 78(17), 8250-8266; 2013

Hung, David T. et al, PCT Int. Appl., 2010051501, 6 May 2010

Example 1

An exemplary procedure for the preparation of intermediate compound 6.

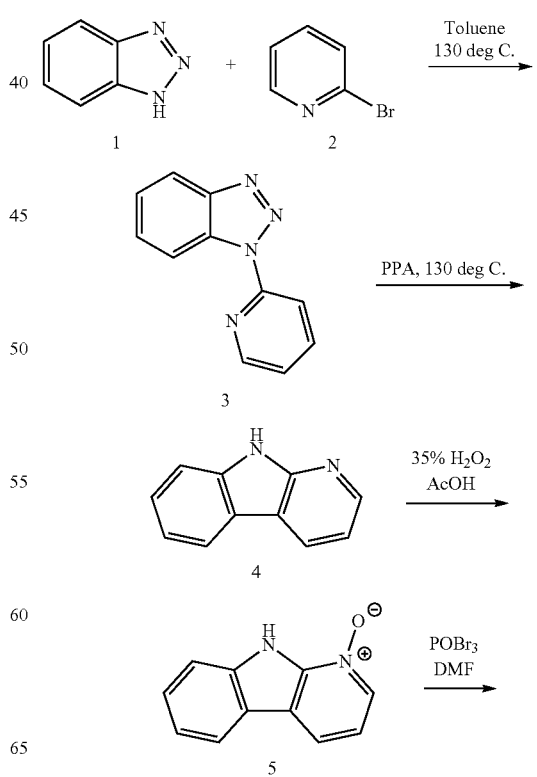

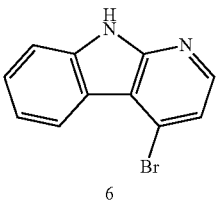

6

Synthesis of 1-(pyridin-2-yl)-1H-benzo[d][1,2,3]triazole (3)

A suspension of 1H-benzo-[1,2,3] triazole (1, 40 g, 335 mmol) and 2-bromopyridine (2, 105 g, 671 mmol) in toluene (160 mL) was heated at reflux for 18 h after which, the reaction mixture was poured into EtOAc (1 L). The resulting white solid precipitate was dissolved by addition of aqueous KOH (10%, 85 mL). The phases were separated, and the organic layer was washed with aqueous KOH (10%, 2×250 mL). The organic layer was dried over anhydrous $Na_2SO_4$, filtered and concentrated to dryness. The isolated solids were recrystallized from $CH_3OH$ giving a 62% yield of compound 3. $^1$H NMR (500 MHz, $CDCl_3$) δ ppm: 8.65 (d, 1H), 8.62 (d, 1H), 8.31 (d, 1H), 8.11 (d, 1H), 7.94 (m, 1H), 7.59 (t, 1H), 7.46 (t, 1H), 7.33 (m, 1H); Mass (m/z): 197.2 (M+H).

Synthesis of 9H-pyrido[2,3-b]indole (4)

To compound 3 (40 g, 203 mmol) was added polyphosphoric acid (160 g) pre-heated to 160° C. Once gas evolution was complete, $H_2O$ (900 mL) was added and the pH of the solution was adjusted >10 by addition of aqueous NaOH (10M). The mixture was then sonicated at 50° C. until the reaction mass was fully suspended. The suspension was poured into $H_2O$ (500 mL) and cooled to room temperature. After 20 min, the resulting solid was collected by filtration, washed with $H_2O$ (2×150 ML) and dried under vacuum giving a 35% yield of crude compound 4. $^1$H NMR (500 MHz, DMSO-$d_6$) δ ppm: 11.72 (br, 1H), 8.44 (d, 1H), 8.37 (d, 1H), 8.11 (d, 1H), 7.47 (dd, 1H), 7.38-7.44 (m, 1H), 7.16-7.20 (m, 1H), 7.15 (d, 1H); Mass (m/z): 169.2 (M+H)

Synthesis of 9H-pyrido[2,3-b]indole 1-oxide (5)

Aqueous $H_2O_2$ (35%, 2.8 g, 83 mmol) was added dropwise to a solution of crude compound 4 (2 g, 11.9 mmol) in $CH_3COOH$ (17 mL). The reaction mixture was refluxed for 4 h. Additional aqueous $H_2O_2$ (35%, 1 mL) was added dropwise and refluxing was continued for an additional 2 h. The solvent was then removed under vacuum and pH of the oily residue was adjusted to 8 on treatment with saturated aqueous $K_2CO_3$. The resulting solution was stirred overnight. The resulting solid was collected by filtration, washed with $H_2O$ and dried under giving a 67% yield of compound 5. $^1$H NMR (500 MHz, DMSO-$d_6$) δ ppm: 12.58 (br, 1H), 8.34 (d, 1H), 8.20 (dd, 2H), 7.56 (m, 2H), 7.30 (t, 1H), 7.23 (t, 1H). Mass (m/z): 185.2 (M+H).

Synthesis of 4-bromo-9H-pyrido[2,3-b]indole (6)

A suspension of compound 5 (1 g, 5.5 mmol) in anhydrous DMF (10 mL) was cooled to 0° C. and $POBr_3$ (3.66 g, 12.8 mmol) was added dropwise with stirring. The reaction was stirred for 24 h at room temperature and then poured into $H_2O$ (20 mL). After cooling to 0-5° C. the pH of the solution was adjusted to 8-10 with aqueous KOH (10%). After stirring for an additional 15 min, the resulting precipitate was collected by filtration, washed with $H_2O$ 15 mL and dried under vacuum. The crude material was purified on silica gel (20% EtOAc in Hexane) giving a 50% yield of compound 6. $^1$H NMR (500 MHz, DMSO-$d_6$) δ ppm: 12.19 (br, 1H), 8.46 (d, 1H), 8.27 (d, 1H), 7.57 (m, 2H), 7.46 (d, 1H), 7.32 (m, 1H). Mass (m/z): 247.2 (M+H).

Example 2

An exemplary procedure for the preparation of intermediate compound 6-I.

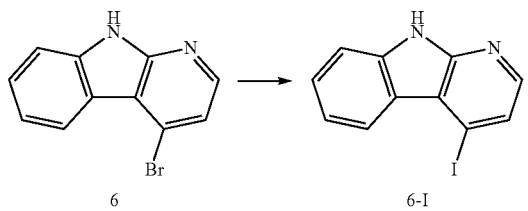 [SMILES: Brc1ccnc2[nH]c3ccccc3c12 ; Ic1ccnc2[nH]c3ccccc3c12]

Synthesis of 4-iodo-9H-pyrido[2,3-b]indole (6-I)

To a solution of 4-bromo-9H-pyrido[2,3-b]indole (compound 6, 1 g, 4.04 mmol) and NaI (0.95 g, 6.38 mmol) in anhydrous acetonitrile (20 mL) was slowly added acetyl chloride (0.95 g, 12.12 mmol). The mixture was allowed to stir at reflux and under nitrogen until the reaction was complete (24 hours). The excess acetonitrile was removed in vacuo. 10% aqueous potassium carbonate solution (10 mL) was added to the residue and the mixture was extracted with $CH_2Cl_2$ (3×20 mL). The combined organic extracts were washed with 10% aqueous sodium bisulfite solution and brine, dried over anhydrous sodium sulfate, filtered and concentrated giving crude acylated compound 6-I. To a solution of this crude product in THF (15 mL) was added 1M aqueous sodium hydroxide (10 mL). The mixture was stirred at room temperature until the reaction was complete (2.5 hours). The solvent was removed in vacuo and the residue was diluted with water (20 mL) and extracted with $CH_2Cl_2$ (40 mL). The organic extracts were washed with brine, dried over anhydrous sodium sulfate, filtered and concentrated in vacuo. The resulting crude compound 6-I was isolated in 42% yield and 77% purity by LCMS. This crude material was used without further purification. Mass (m/z): 295.01.

Example 3

An exemplary procedure for the preparation of intermediate compound 9a.

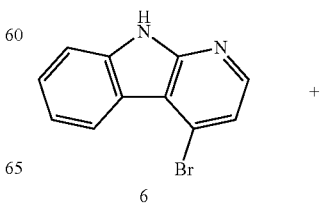

+

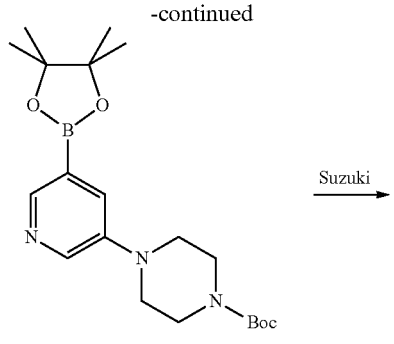

7a

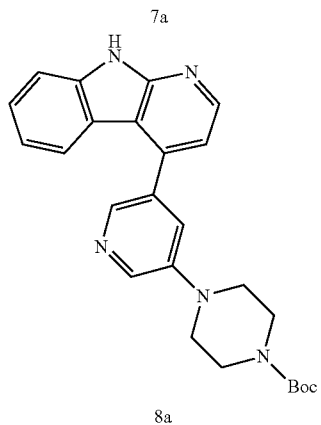

8a

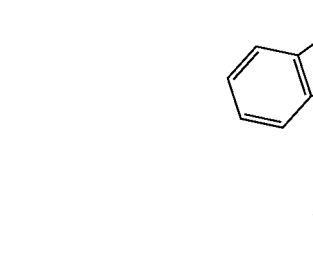

9a

Synthesis of Compound 8a

A solution of compound 6 (100 mg, 0.404 mmol), boronate ester 7a (250 mg, 0.60 mmol), aqueous sodium carbonate (2.0M, 1 mL, 2.0 mmol) and DME (4 mL) was purged with nitrogen and Pd(PPh₃)₄ (50 mg, 0.04 mmol) was added. The resulting mixture was stirred in a microwave reactor at 150° C. for 90 min. After cooling to room temperature, the mixture was poured into water (20 ml) and extracted with EtOAc (2×50 mL). The combined organic phases were dried over anhydrous sodium sulfate, filtered, and concentrated in vacuo. Purification on silica gel (EtOAc/Hexane 1/1) gave compound 8a (50% yield). Mass (m/z): 430.3 (M+H).

Synthesis of Compound 9a

To a suspension of compound 8a (87 mg, 0.202 mmol) in MeOH (3 mL) was added methanolic HCl (prepared by bubbling HCl gas into MeOH, 3 mL) dropwise and with stirring. After addition, stirring was continued at room temperature for 2 hours after which, the mixture was concentrated in vacuo giving 100 mg of compound 9a HCl salt. This material was treated with MP-carbonate (tetra alkyl ammonium carbonate-polymer bounded, 150 mg) for 2 hours, filtered and concentrated giving compound 9a (36 mg, 55% yield) as an off white solid. ¹HNMR (500 MHz, DMSO-d₆) δ ppm: 12.05 (b, 1H), 8.50 (m, 2H), 8.25 (s, 1H), 7.60-7.45 (m, 3H), 7.42 (t, 1H), 7.20 (d, 1H), 7.05 (t, 1H), 3.30 (t, 4H), 2.90 (t, 4H). Mass (m/z): 330.3 (M+H). Purity: 99.14% by HPLC.

Example 4

An exemplary procedure for the preparation of intermediate compound 9b.

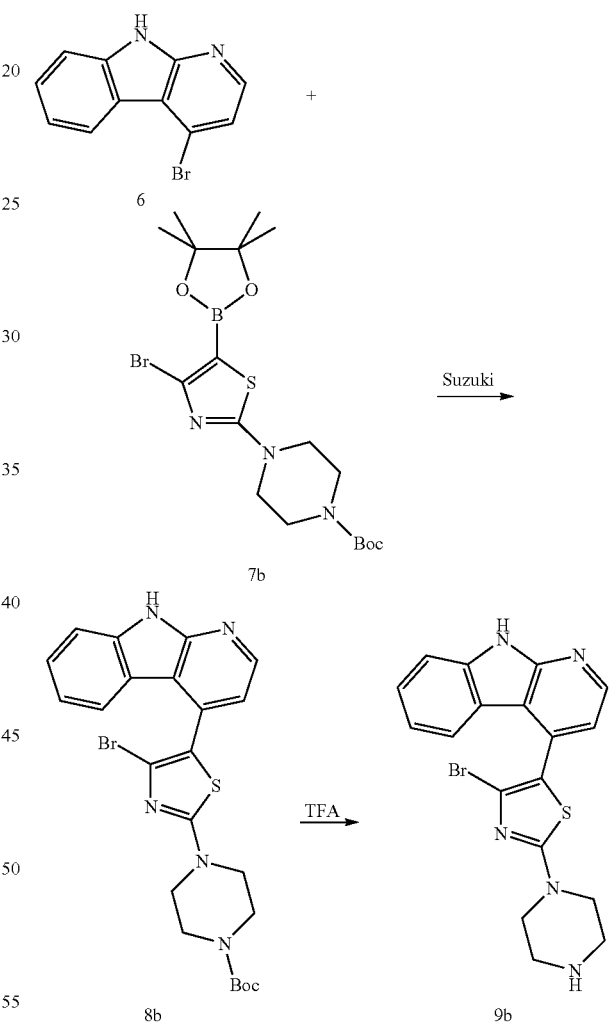

Synthesis of Compound 8b

A solution of compound 6 (1.01 mmol), boronate ester 7b (1.52 mmol), aqueous sodium carbonate (2.0M, 1 mL, 2.0 mmol) and dioxane (4 mL) is purged with nitrogen and Pd(PPh₃)₄ (0.05 mmol) is added. The resulting mixture is stirred in a microwave reactor at 140° C. for 45 min. After cooling to room temperature, the mixture is poured into water (30 mL) and washed with EtOAc (2×50 mL). The combined organic phases are dried over anhydrous Na₂SO₄, filtered, and concentrated in vacuo. The crude product is purified on silica gel (40% EtOAc in hexane) giving compound 8b.

Synthesis of Compound 9b

Trifluoroacetic acid (1.0 mmol) is added dropwise to a suspension of compound 8b (0.2 mmol) in anhydrous dichloromethane (3 mL). After stirring for 2 h at room temperature, the mixture is concentrated in vacuo giving compound 9b. This material is stirred with desalting resin (MP-carbonate) in MeOH (4 mL) for 2 h. The resin is removed by filtration and the filtrate is concentrated to dryness. The residue is purified by preparative HPLC.

Example 5

An exemplary procedure for the preparation of intermediate compound 9c.

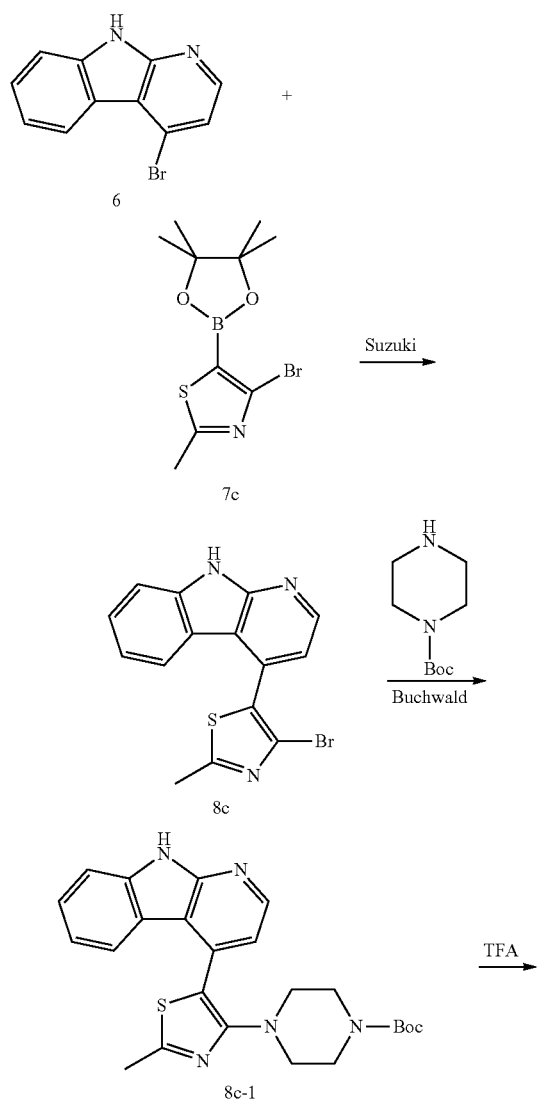

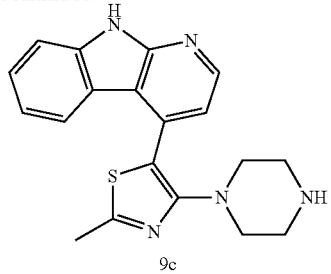

Synthesis of Compound 8c

A solution of compound 6 (1.01 mmol), boronate ester 7c (1.52 mmol), aqueous sodium carbonate (2.0M, 1 mL, 2.0 mmol) and dioxane (4 mL) is purged with nitrogen and Pd(PPh₃)₄ (0.05 mmol) is added. The resulting mixture is stirred in a microwave reactor at 140° C. for 45 min. After cooling to room temperature, the mixture is poured into water (30 mL) and washed with EtOAc (2×50 mL). The combined organic phases are dried over anhydrous Na₂SO₄, filtered, and concentrated in vacuo. The crude product is purified on silica gel (40% EtOAc in hexane) giving compound 8c.

Synthesis of Compound 8c-1

A mixture of compound 8c (2.5 mmol), N-Boc-piperazine (2.8 mmol), palladium(II)acetate (0.05 mmol), BINAP (0.1 mmol) and cesium carbonate (15.1 mmol) in anhydrous dioxane (10 mL) is stirred at 90° C. under N₂ for 14 h. After cooling to room temperature, the mixture is filtered through Celite and the Celite pad is washed with ethyl acetate (2×10 mL). The combined filtrate is concentrated to dryness and the crude product is purified on silica gel giving compound 8c-1.

Synthesis of Compound 9c

Trifluoroacetic acid (1.0 mmol) is added dropwise to a suspension of compound 8c-1 (0.2 mmol) in anhydrous dichloromethane (3 mL). After stirring for 2 h at room temperature, the mixture is concentrated in vacuo giving compound 9c. This material is stirred with desalting resin (MP-carbonate) in MeOH (4 mL) for 2 h. The resin is removed by filtration and the filtrate is concentrated to dryness. The residue is purified by preparative HPLC.

Example 6

An exemplary procedure for the preparation of intermediate compound 9d.

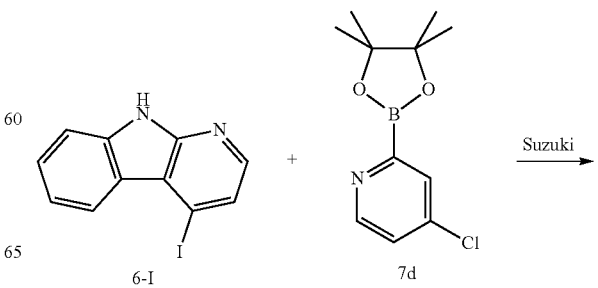

-continued

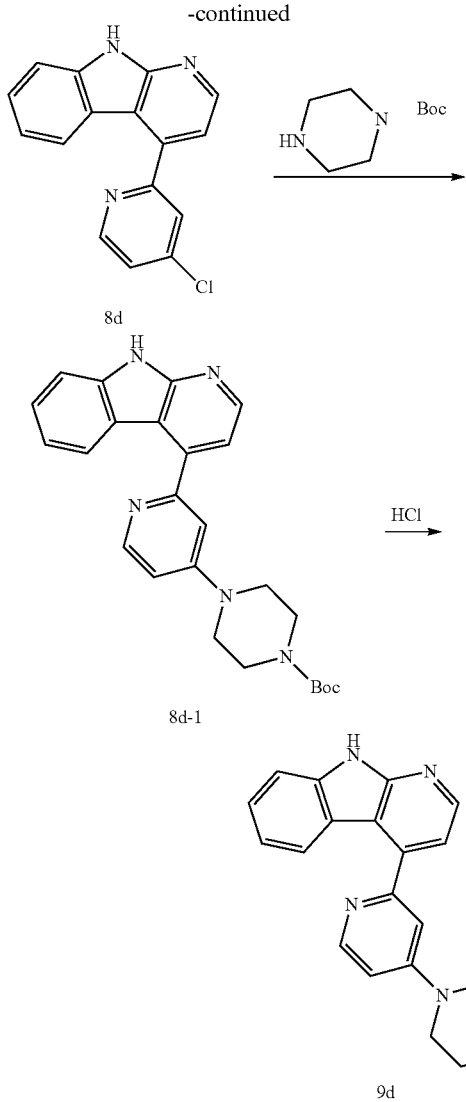

reaction mixture is cooled to room temperature, and the solvent are removed in vacuo. The residue is extracted from water with dichloromethane, the organic layer is dried over anhydrous magnesium sulfate, and the solvent is removed in vacuo. The crude mixture is purified on silica gel giving compound 8d-1.

Synthesis of Compound 9d

To a suspension of compound 8d-1 (0.202 mmol) in MeOH (3 mL) is added methanolic HCl (prepared by bubbling HCl gas into MeOH, 3 mL) dropwise and with stirring. After addition, stirring is continued at room temperature for an additional 2 hours after which, the mixture is concentrated in vacuo giving compound 8d HCl salt. This material is treated with MP-carbonate (tetra alkyl ammonium carbonate-polymer bounded) for 2 hours, filtered and concentrated giving compound 8d.

Example 7

An exemplary procedure for the preparation of intermediate compound 9e.

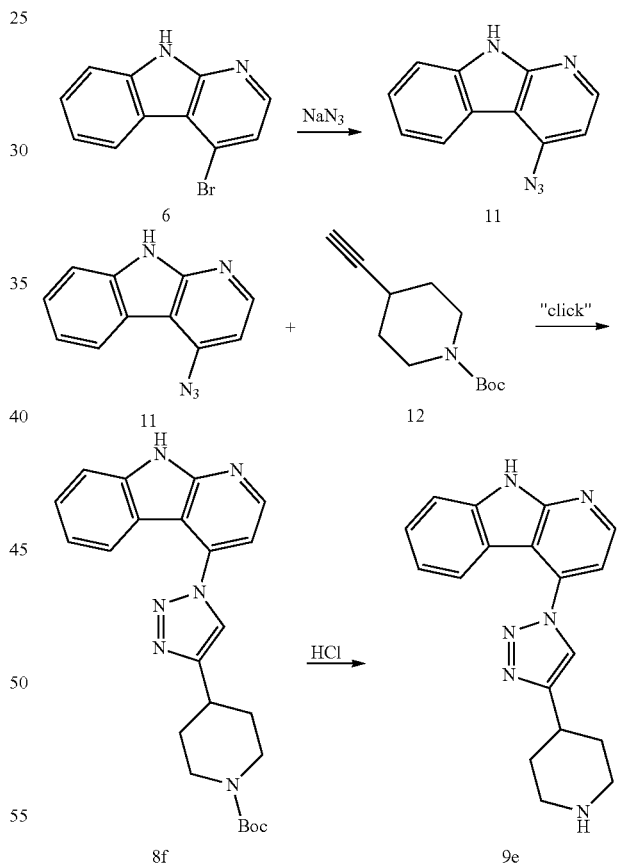

Synthesis of Compound 8d

A solution of compound 6-I (100 mg, 0.34 mmol), boronate ester 7d (160 mg, 0.68 mmol), potassium carbonate (100 mg, 0.68 mmol) and DMF (5 mL) was purged with nitrogen and PdCl$_2$(dppf) (15 mg, 0.017 mmol) was added. The resulting mixture was stirred in a microwave reactor at 150° C. for 45 min. After cooling to room temperature, the mixture was poured into water (20 ml) and extracted with EtOAc (2×40 mL). The combined organic phases were dried over anhydrous sodium sulfate, filtered, and concentrated in vacuo. Purification on silica gel (EtOAc/Hexane 1/1) gave compound 8d in 5.2% yield. Mass (m/z): 280.2. Purity: 94.68% by LC-MS.

Synthesis of Compound 8d-1

To a solution of compound 8d (0.05 mmol) in THF (0.5 mL) is added Boc-piperazine (0.5 mmol). A freshly prepared solution of LDA in THF (2.1 M, 55 mL, 0.11 mmol) is then added at room temperature via syringe. The mixture is heated to reflux until all starting material is consumed. The Synthesis of Compound 11

A mixture of compound-6 (500 mg, 2.02 mmol) and sodium azide (394 mg, 3.07 mmol) in dimethyl sulfoxide (10 was heated to 100° C. for 12 hours with stirring. The reaction was allowed to cool to room temperature after which, it was diluted with ethyl acetate (20 mL), washed with water (10 mL) and brine (10 mL). The organic layer was dried over anhydrous sodium sulfate, filtered and concentrated under reduced pressure giving the crude product. Purification on silica gel (EtOAC/Hexane 3/7) gave the desired pure compound 11 in 35% yield. Mass (m/z): 210.2 (M+H).

Synthesis of compound 8f

To a stirred solution of compound 11 (300 mg, 1.43 mmol) and compound 12 (300 mg, 1.43 mmol) in a mixture of of t-Butanol/water (20 mL, 1:1) was added copper sulfate pentahydrate (159 mg, 0.717 mmol) followed by sodium ascorbate (198 mg, 1.43 mmol). The resulting mixture was stirred overnight at 80° C. and monitored by TLC, On completion, the reaction mixture was diluted with a mixture of ethyl acetate/water (30 mL, 1:1). The layers were separated and the organic layer was washed with 5% ammonium hydroxide solution (10 mL) followed by brine (15 mL). The combined organic layers were dried over anhydrous sodium sulfate, filtered and concentrated under reduced pressure giving the crude residue. Purification on silica gel (EtOAC/Hexane 4/6) gave pure compound 8f in 10% yield. Mass (m/z): 419.3 (M+H).

Synthesis of Compound 9e

To a suspension of compound 8f (60 mg, 0.143 mmol) in MeOH (3 mL) was added methanolic HCl (prepared by bubbling HCl gas into MeOH, 3 mL) dropwise and with stirring. After addition, stirring was continued at room temperature for 2 hours after which, the mixture was concentrated in vacuo giving 70 mg of compound 9e HCl salt. This material was treated with MP-carbonate (tetra alkyl ammonium carbonate-polymer bounded, 100 mg) for 2 hours, filtered and concentrated giving compound 9e (15 mg, 33% yield) as an off white solid. $^1$HNMR (500 MHz, DMSO-D$_6$) δ ppm: 12.40 (b, 1H), 8.69 (s, 1H), 8.60 (d, 1H), 7.82 (d, 1H), 7.57 (d, 1H), 7.52 (t, 1H), 7.46 (d, 1H), 7.18 (t, 1H), 3.09 (m, 2H), 2.97 (m, 1H), 2.70 (t, 2H), 2.04 (m, 2H), 1.67 (m, 2H); Mass (m/z): 319.2 (M+H). Purity: 98.74% by HPLC.

Example 8

An exemplary procedure for the preparation of intermediate compound 9f.

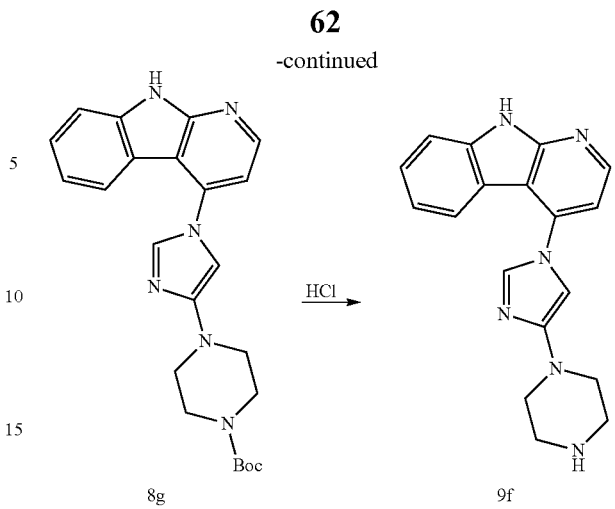

Synthesis of Compound 9f

CuI (5 mmol), DMEDA (10 mmol) and K$_2$CO$_3$ (20 mmol) are added to a solution of compound 6 (0.1 mol) and compound 13 (0.1 mol) in DMF (100 mL). The resulting mixture is stirred at reflux under an argon atmosphere for 12 hours, then cooled, filtered and concentrated to dryness giving intermediate compound 8g. The residue is dissolved in MeOH (200 mL) and 10 M aq HCl (20 mL) is added. The resulting mixture is concentrated to dryness and the residue is recrystallized to give compound 9f as its hydrochloride. This material is stirred with desalting resin (MP-carbonate) in MeOH (4 mL) for 2 h. The resin is removed by filtration and the filtrate is concentrated to dryness. The residue is purified by preparative HPLC.

Example 9

An exemplary procedure for the preparation of intermediate compound 9g.

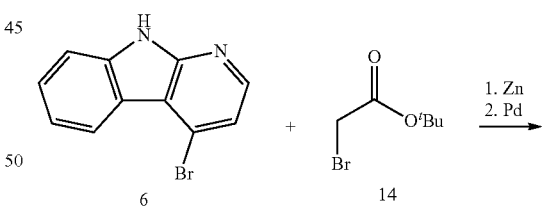

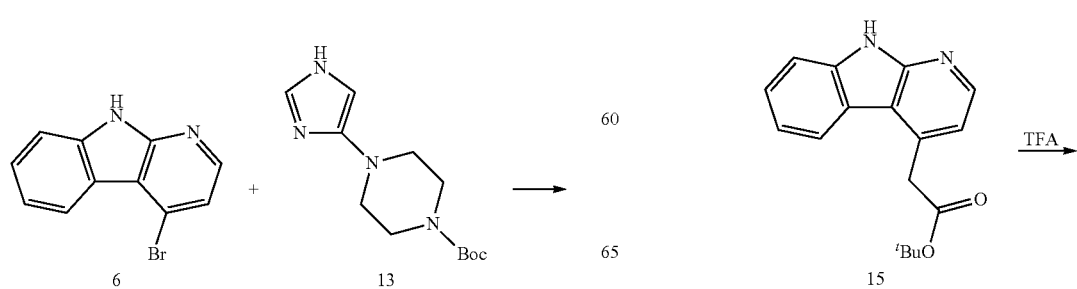

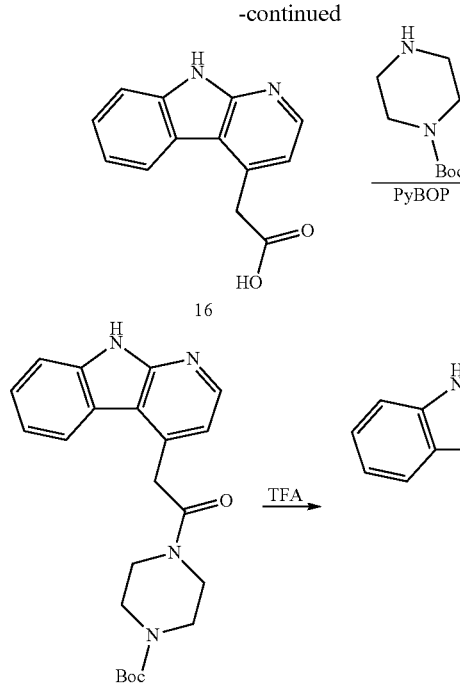

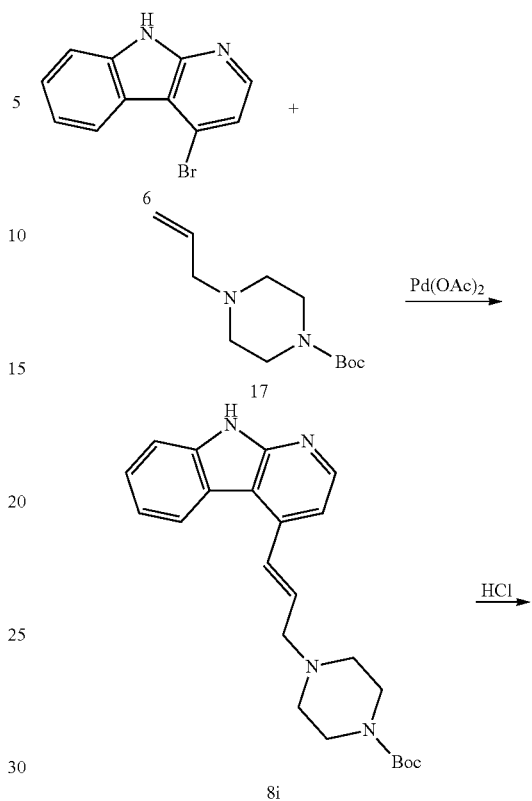

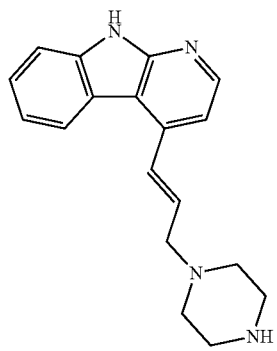

Synthesis of Compound 15

Compound 15 is prepared from the coupling of compound 6 with the organizinc derivative of compound 14 prepared as described by Hama, et al.

Synthesis of Compound 16

Trifluoroacetic acid (1.0 mmol) is added dropwise to a solution of compound 15 (0.2 mmol) in anhydrous dichloromethane (3 mL). After stirring for 2 h at room temperature, the mixture is concentrated in vacuo giving compound 16.

Synthesis of Compound 8h

Compound 16 (1 mmol) is combined with N-Boc-piperazine (1 mmol) in anhydrous dichloromethane (20 mL). The resulting solution is cooled to 0 deg C. and DIEA (3 mmol) is added. PyBOP (1 mmol) is added and the resulting mixture is stirred at room temperature until complete. The reaction is concentrated to dryness and the residue is purified on silica gel giving compound 8h.

Synthesis of Compound 9g

Trifluoroacetic acid (1.0 mmol) is added dropwise to a suspension of compound 8 h (0.2 mmol) in anhydrous dichloromethane (3 mL). After stirring for 2 h at room temperature, the mixture is concentrated in vacuo giving compound 9g. This material is stirred with desalting resin (MP-carbonate) in MeOH (4 mL) for 2 h. The resin is removed by filtration and the filtrate is concentrated to dryness. The residue is purified by preparative HPLC.

Example 10

An exemplary procedure for the preparation of intermediate compound 9h.

Synthesis of Compound 8i

Compound 6 (500 mg, 2.02 mmol), compound 17 (457 mg, 2.02 mmol) and triethylamine (1.7 mL, 12.12 mmol) were combined with mixture of DMSO/dioxane (10 mL, 1/4). Pd(PPh$_3$)$_4$ (116 mg, 0.101 mmol) was added with stirring. The resulting mixture was degassed with a stream of N$_2$ for 30 min and then stirred in a sealed tube at 140° C. overnight. The mixture was then poured into water (20 mL) and extracted with EtOAc (2×50 mL). The combined organic phases were dried over anhydrous Na$_2$SO$_4$, filtered, and concentrated in vacuo. Purification on silica gel (EtOAC/Hexane 4/6) gave compound 8i in 6.3% isolated yield. Mass (m/z): 393.3 (M+H).

Synthesis of Compound 9h

To a suspension of compound 8i (45 mg, 0.114 mmol) in MeOH (2 mL) was added methanolic HCl (prepared by bubbling HCl gas into MeOH, 2 mL) dropwise and with stirring. After addition, stirring was continued at room temperature for 2 hours after which, the mixture was concentrated in vacuo giving 35 mg of compound 9h HCl salt. This material was treated with MP-carbonate (tetra alkyl ammonium carbonate-polymer bounded, 50 mg) for 2 hours, filtered and concentrated giving compound 9h (10 mg, 30% yield) as an off white solid. $^1$HNMR (500 MHz, DMSO-D6) δ ppm: 11.98 (brs, 1H), 8.40-8.21 (m, 1H), 8.1-8.05 (m, 1H), 7.58-7.38 (m, 2H), 7.2-7.0 (m, 2H), 5.81-5.61 (m, 1H), 5.60-5.42 (m, 1H), 3.4 (m, 2H), 2.8 (m, 4H) & 2.4 (m, 4H). Mass (m/z): 293.3 (M+H). Purity: 90.75% by HPLC.

Example 11

An exemplary procedure for the preparation of intermediate compound 9j.

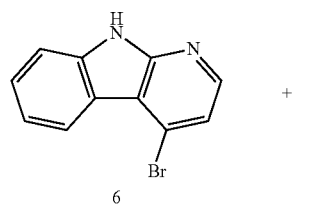

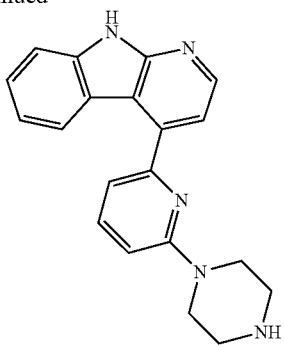

9j

Synthesis of Compound 8j

A Solution of compound 6 (100 mg, 0.405 mmol), boronate ester 7j (237 mg, 0.608 mmol), aqueous sodium carbonate (2.0M, 1 mL, 2.0 mmol) and DME (4 mL) was purged with nitrogen and Pd(PPh$_3$)$_4$ (50 mg, 0.04 mmol) was added. The resulting mixture was stirred in a microwave reactor at 150° C. for 90 min. After cooling to room temperature, the mixture was poured into water (20 ml) and extracted with EtOAc (2×50 mL). The combined organic phases were dried over anhydrous sodium sulfate, filtered, and concentrated in vacuo. Purification on silica gel (EtOAc/Hexane 3/2) gave compound 8j (30% yield). Mass (m/z): 430.3 (M+H).

Synthesis of Compound 9j

To a suspension of compound 8j (53 mg, 0.202 mmol) in MeOH (3 mL) was added methanolic HCl (prepared by bubbling HCl gas into MeOH, 3 mL) dropwise and with stirring. After addition, stirring was continued at room temperature for 2 hours after which, the mixture was concentrated in vacuo giving 55 mg of compound 9j HCl salt. This material was treated with MP-carbonate (tetra alkyl ammonium carbonate-polymer bounded, 150 mg) for 2 hours, filtered and concentrated giving compound 9j (12 mg, 30% yield) as an off white solid. $^1$HNMR (500 MHz, DMSO-d$_6$) δ ppm: 11.97 (b, 1H), 8.47 (d, 1H), 7.94 (d, 1H), 7.75 (t, 1H), 7.49 (m, 2H), 7.30 (d, 1H), 7.07-6.93 (m, 3H), 3.36 (m, 4H), 2.78 (m, 4H). Mass (m/z): 330.3 (M+H). Purity: 95.43% by HPLC.

Example 12

An exemplary procedure for the preparation of intermediate compound 9k.

67

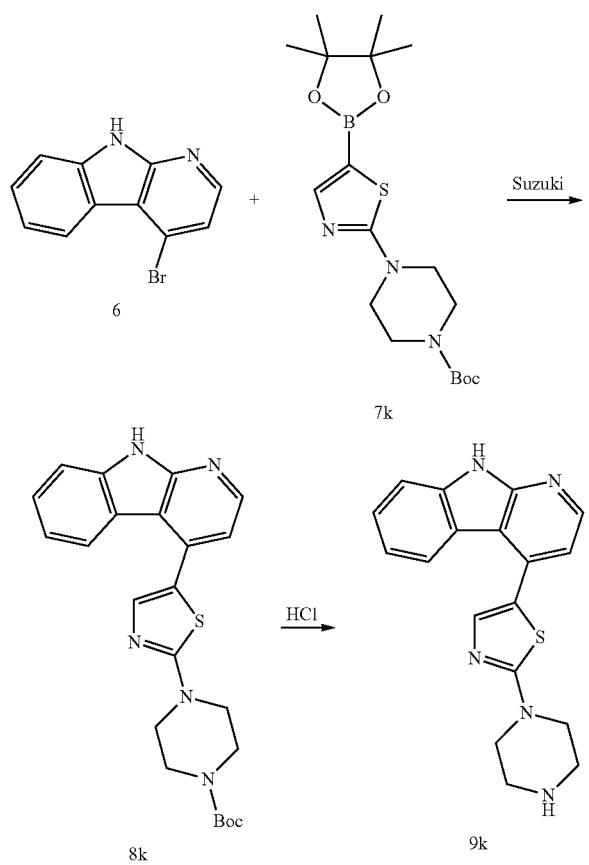

Synthesis of Compound 8k

A solution of compound 6 (100 mg, 0.405 mmol), boronate ester 7k (240 mg, 0.606 mmol), aqueous sodium carbonate (2.0M, 1 mL, 2.0 mmol) and DME (4 mL) was purged with nitrogen and Pd(PPh$_3$)$_4$ (50 mg, 0.04 mmol) was added. The resulting mixture was stirred in a microwave reactor at 150° C. for 90 min. After cooling to room temperature, the mixture was poured into water (20 ml) and extracted with EtOAc (2×50 mL). The combined organic phases were dried over anhydrous sodium sulfate, filtered, and concentrated in vacuo. Purification on silica gel (EtOAc/Hexane 3/2) gave compound 8k (40% yield). Mass (m/z): 436.3 (M+H).

Synthesis of Compound 9k

To a suspension of compound 8k (71 mg, 0.163 mmol) in MeOH (3 mL) was added methanolic HCl (prepared by bubbling HCl gas into MeOH, 3 mL) dropwise and with stirring. After addition, stirring was continued at room temperature for 2 hours after which, the mixture was concentrated in vacuo giving 80 mg of compound 9k HCl salt. This material was treated with MP-carbonate (tetra alkyl ammonium carbonate-polymer bounded, 110 mg) for 2 hours, filtered and concentrated giving compound 9k (16 mg, 55% yield) as an off white solid. $^1$HNMR (500 MHz, DMSO-d$_6$) δ ppm: 12.01 (b, 1H), 8.36 (d, 1H), 8.15 (d, 1H), 7.69 (s, 1H), 7.54-7.45 (m, 2H), 7.17 (t, 1H), 7.08 (d, 1H), 3.46 (t, 4H), 2.86 (t, 4H). Mass (m/z): 336.2 (M+H). Purity: 97.8% by HPLC.

68

Example 13

An exemplary procedure for the preparation of intermediate compound 9l.

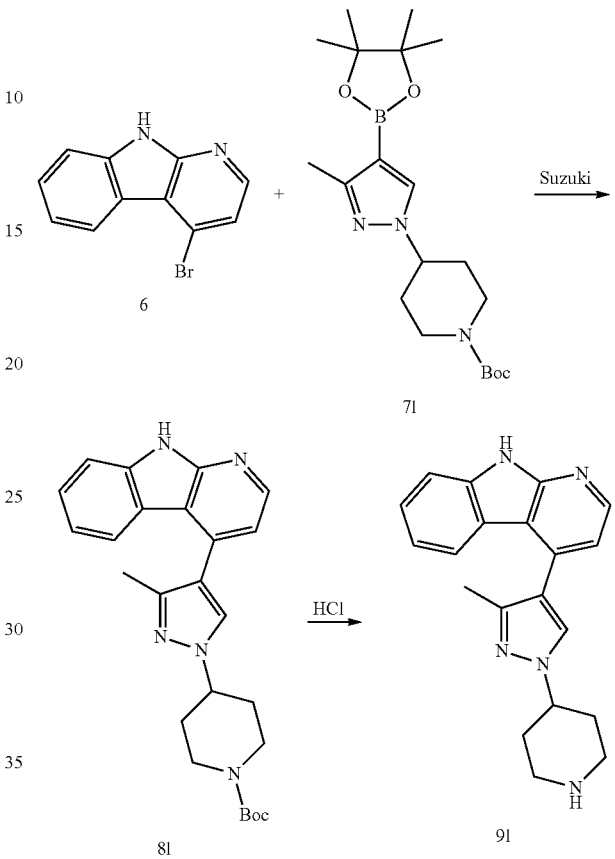

Synthesis of Compound 8l

A solution of compound 6 (100 mg, 0.405 mmol), boronate ester 7l (250 mg, 0.60 mmol), aqueous sodium carbonate (2.0M, 1 mL, 2.0 mmol) and DME (4 mL) was purged with nitrogen and Pd(PPh$_3$)$_4$ (50 mg, 0.04 mmol) was added. The resulting mixture was stirred in a microwave reactor at 150° C. for 90 min. After cooling to room temperature, the mixture was poured into water (20 ml) and extracted with EtOAc (2×50 mL). The combined organic phases were dried over anhydrous sodium sulfate, filtered, and concentrated in vacuo. Purification on silica gel (EtOAc/Hexane 1/1) gave compound 8l (30% yield). Mass (m/z): 432.4 (M+H).

Synthesis of Compound 9l

To a suspension of compound 8l (80 mg, 0.185 mmol) in MeOH (3 mL) was added methanolic HCl (prepared by bubbling HCl gas into MeOH, 3 mL) dropwise and with stirring. After addition, stirring was continued at room temperature for 2 hours after which, the mixture was concentrated in vacuo giving 90 mg of compound 9l HCl salt. This material was treated with MP-carbonate (tetra alkyl ammonium carbonate-polymer bounded, 110 mg) for 2 hours, filtered and concentrated giving compound 9l (18 mg, 20% yield) as an off white solid. $^1$HNMR (500 MHz, DMSO-d$_6$) δ ppm: 11.94 (b, 1H), 8.39 (d, 1H), 8.09 (s, 1H), 7.63-7.39 (m, 4H), 7.09 (t, 1H), 7.03 (d, 1H), 4.50 (m, 1H), 3.34 (t, 2H), 2.99 (t, 2H), 2.23 (m, 4H), 2.05 (s, 3H). Mass (m/z): 332.3 (M+H). Purity: 97.4% by HPLC.

Example 14

An exemplary procedure for the preparation of intermediate compound 9m.

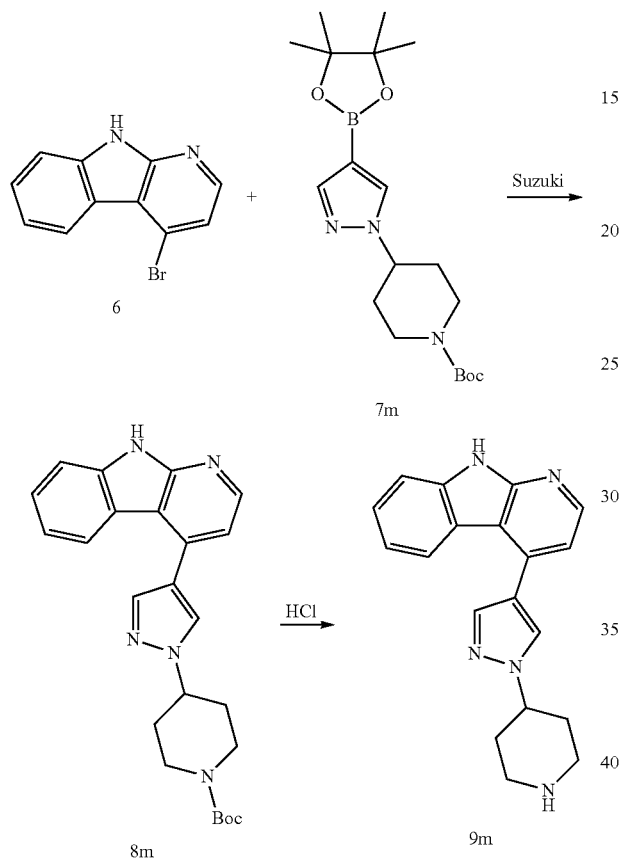

Synthesis of Compound 8m

A solution of compound 6 (100 mg, 0.404 mmol), boronate ester 71 (230 mg, 0.60 mmol), aqueous sodium carbonate (2.0M, 1 mL, 2.0 mmol) and DME (4 mL) was purged with nitrogen and Pd(PPh$_3$)$_4$ (50 mg, 0.04 mmol) was added. The resulting mixture was stirred in a microwave reactor at 150° C. for 90 min. After cooling to room temperature, the mixture was poured into water (20 ml) and extracted with EtOAc (2×50 mL). The combined organic phases were dried over anhydrous sodium sulfate, filtered, and concentrated in vacuo. Purification on silica gel (EtOAc/Hexane 2/3) gave compound 8m (20% yield). Mass (m/z): 418.3 (M+H).

Synthesis of compound 9m

To a suspension of compound 8m (38 mg, 0.091 mmol) in MeOH (3 mL) was added methanolic HCl (prepared by bubbling HCl gas into MeOH, 3 mL) dropwise and with stirring. After addition, stirring was continued at room temperature for 2 hours after which, the mixture was concentrated in vacuo giving 43 mg of compound 9 m HCl salt. This material was treated with MP-carbonate (tetra alkyl ammonium carbonate-polymer bounded, 100 mg) for 2 hours, filtered and concentrated giving compound 9 m (10 mg, 35% yield) as an off white solid. $^1$HNMR (500 MHz, DMSO-d$_6$) δ ppm: 11.93 (b, 1H), 8.35 (m, 2H), 8.02 (d, 1H), 7.94 (s, 1H), 7.58-7.42 (m, 2H), 7.25-7.09 (m, 2H), 4.35 (m, 1H), 3.10 (m, 2H), 2.62 (m, 2H), 2.08-1.86 (m, 4H). Mass (m/z): 318.3 (M+H). Purity: 95.1% by HPLC.

Example 15

An exemplary procedure for the preparation of intermediate compound 9n.

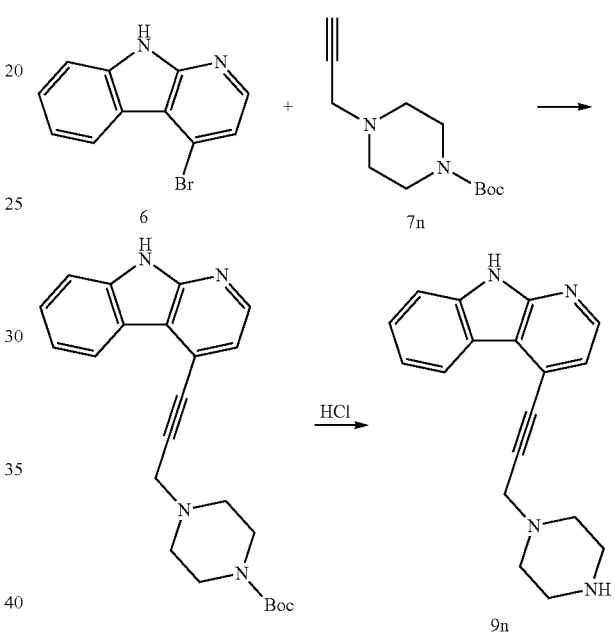

Synthesis of compound 8n

To a stirred solution of compound 6 (500 mg, 2.02 mmol), compound 7n (460 mg, 2.02 mmol) and triethylamine (1.7 mL, 12.12 mmol) in DMF (20 was added Pd(PPh$_3$)$_2$Cl$_2$ (140 mg, 0.202 mmol) and CuI (80 mg, 0.404 mmol). The mixture was degassed with a stream of N$_2$ for 30 min and then stirred at 140° C. overnight. The reaction mixture was then poured into water (20 mL) and extracted with EtOAc (2×50 mL). The combined organic phases were dried over anhydrous sodium sulfate, filtered, and concentrated in vacuo. Purification of the residue on silica gel (EtOAC/Hexane 4/6) gave compound 8n in 10% yield. Mass (m/z): 391.3 (M+H).

Synthesis of compound 9n

To a suspension of compound 8n (80 mg, 0.204 mmol) in MeOH (3 mL) was added methanolic HCl (prepared by bubbling HCl gas into MeOH, 3 mL) drop wise and with stirring. After addition, stirring was continued at room temperature for 2 hours after which, the mixture was concentrated in vacuo giving 85 mg of compound 9n HCl salt.

This material was treated with MP-carbonate (tetra alkyl ammonium carbonate-polymer bounded, 90 mg) for 2 hours, filtered and concentrated giving compound 9n (12 mg, 20% yield) as an off white solid. ¹HNMR (500 MHz, DMSO-d$_6$) δ ppm: 11.98 (brs, 1H), 8.50-8.20 (m, 2H), 7.55-7.32 (m, 2H), 7.23-7.00 (m, 2H), 3.67 (s, 2H), 2.95-2.50 (m, 8H). Mass (m/z): 291.2 (M+H). Purity: 98.5% by HPLC.

Example 16

An exemplary procedure for the preparation of intermediate compound 9o.

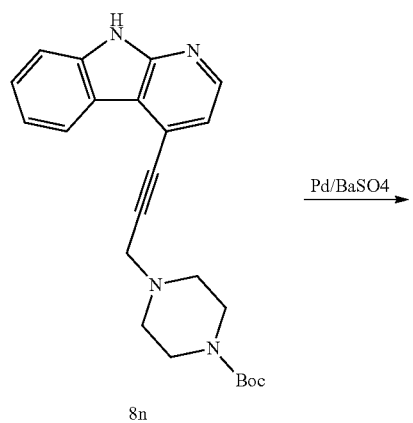

Synthesis of compound 8o

To a solution of compound 8n (100 mg, 0.256 mmol) in MeOH (10 mL) was added Lindlar catalyst (10% Pd/BaSO$_4$, 20 mg) at room temperature. The resulting was stirred under a hydrogen atmosphere (balloon pressure) for 4 h. After consumption of starting material, the reaction was diluted with MeOH (20 mL), filtered through Celite and concentrated in vacuo. The residue was purified on silica gel (EtOAC/Hexane 4/6) giving compound 8o in 40% isolated yield. Mass (m/z): 393.3 (M+H).

Synthesis of compound 9n

To a suspension of compound 8o (30 mg, 0.076 mmol) in MeOH (3 mL) was added methanolic HCl (prepared by bubbling HCl gas into MeOH, 3 mL) drop wise and with stirring. After addition, stirring was continued at room temperature for 2 hours after which, the mixture was concentrated in vacuo giving 45 mg of compound 9o HCl salt. This material was treated with MP-carbonate (tetra alkyl ammonium carbonate-polymer bounded, 90 mg) for 2 hours, filtered and concentrated giving compound 9o. Final purification by prep HPLC gave pure compound 9o (10 mg, 45% yield) as an off white solid. ¹HNMR (500 MHz, DMSO-d$_6$) δ ppm: 11.97 (brs, 1H), 8.40 (m, 1H), 8.10 (m, 1H), 7.60-7.40 (m, 2H), 7.30-7.10 (m, 2H), 7.0 (m, 1H), 6.2 (m, 1H), 3.20 (m, 2H), 2.62 (m, 4H), 2.40-2.10 (m, 4H). Mass (m/z): 293.3 (M+H). Purity: 96.1% by HPLC.

Example 17

An exemplary procedure for the preparation of intermediate compound 9p.

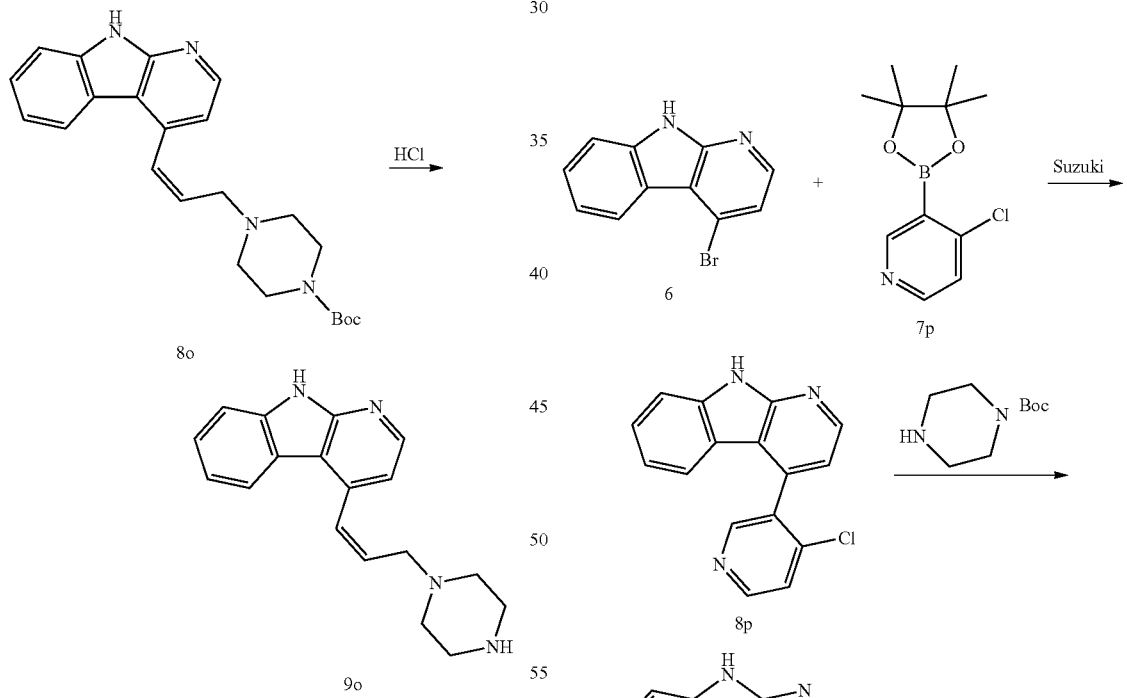

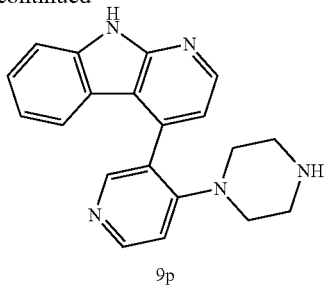

9p

Synthesis of compound 8p

A solution of compound 6 (100 mg, 0.404 mmol), boronate ester 7p (143 mg, 0.60 mmol), aqueous sodium carbonate solution (2.0M, 1 mL, 2.0 mmol) and DME (4 mL) was purged with nitrogen and Pd(PPh$_3$)$_4$ (50 mg, 0.04 mmol) was added. The resulting mixture was stirred in a microwave reactor at 150° C. for 90 min. After cooling to room temperature, the mixture was poured into water (20 mL) and extracted with EtOAc (2×50 mL). The combined organic phases were dried over anhydrous sodium sulfate, filtered, and concentrated in vacuo. The residue was purified on silica gel (EtOAc/Hexane 4/6) giving compound 8p in 35% isolated yield. $^1$HNMR (500 MHz, DMSO-D6) δ ppm: 12.16 (b, 1H), 8.79-8.75 (m, 2H), 8.57 (d, 1H), 7.89 (d, 1H), 7.56 (d, 1H), 7.44 (m, 2H), 7.20 (d, 1H), 7.08-6.95 (m, 2H). Mass (m/z): 280.1 (M+H). Purity: 97.7% by HPLC.

Synthesis of compound 8p-1

To a solution of compound 8p (0.05 mmol) in THF (0.5 mL) is added Boc-piperazine (0.5 mmol). A freshly prepared solution of LDA in THF (2.1 M, 55 mL, 0.11 mmol) is then added at room temperature via syringe. The mixture is heated to reflux until all starting material is consumed. The reaction mixture is cooled to room temperature, and the solvent are removed in vacuo. The residue is extracted from water with dichloromethane, the organic layer is dried over anhydrous magnesium sulfate, and the solvent is removed in vacuo. The crude mixture is purified on silica gel giving compound 8p-1.

Synthesis of compound 9p

To a solution of compound 8p-1 in MeOH (3 mL) is added methanolic HCl (prepared by bubbling HCl gas into MeOH, 3 mL) dropwise and with stirring. After addition, stirring is continued at room temperature for 2 hours after which, the mixture is concentrated in vacuo giving compound 9p HCl salt. This material is treated with MP-carbonate (tetra alkyl ammonium carbonate-polymer bounded, 90 mg) for 2 hours, filtered and concentrated giving compound 9p as its free base.

Example 18

An exemplary procedure for the preparation of intermediate compound 9q.

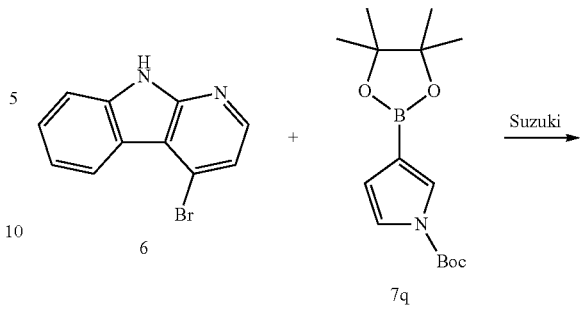

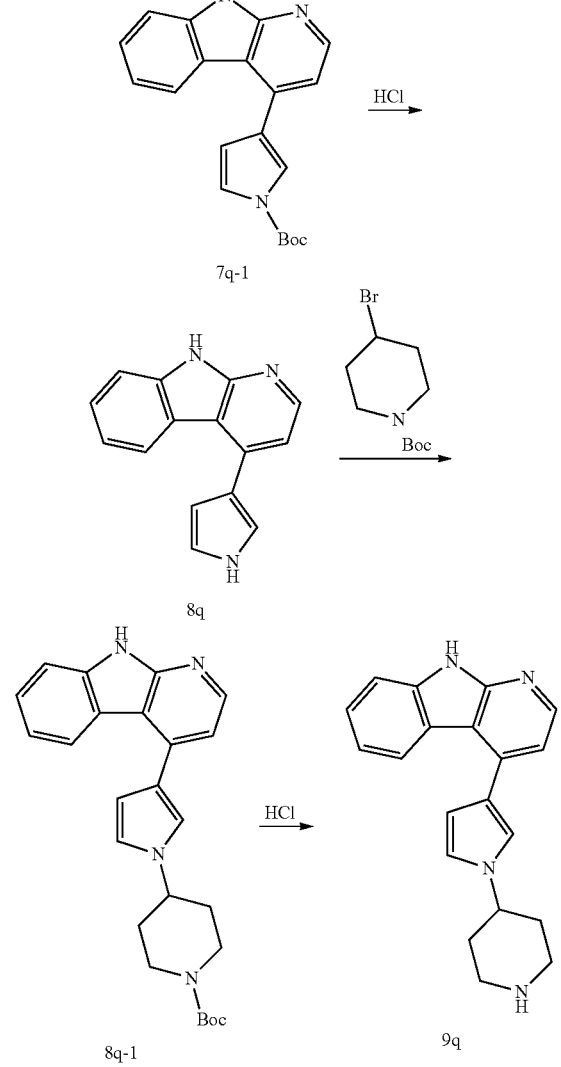

Synthesis of compound 7q-1

A solution of compound 6 (100 mg, 0.404 mmol), boronate ester 7q (175 mg, 0.60 mmol), aqueous sodium carbonate solution (2.0M, 1 mL, 2.0 mmol) and DME (4 mL) was purged with nitrogen and Pd(PPh$_3$)$_4$ (50 mg, 0.04 mmol) was added. The resulting mixture was stirred in a microwave reactor at 150° C. for 90 min. After cooling to room temperature, the mixture was poured into water (20 mL) and extracted with EtOAc (2×50 mL). The combined organic phases were dried over anhydrous sodium sulfate, filtered, and concentrated in vacuo. The residue was purified on silica gel (EtOAc/Hexane 1/1) giving compound 7q-1 in 45% isolated yield.

Synthesis of compound 8q

To a suspension of compound 7q-1 (60 mg, 0.18 mmol) in MeOH (3 mL) was added methanolic HCl (prepared by bubbling HCl gas into MeOH, 3 mL) drop wise and with stirring. After addition, stirring was continued at room temperature for 2 hours after which, the mixture was concentrated in vacuo giving 70 mg of compound 8q HCl salt. This material was treated with MP-carbonate (tetra alkyl ammonium carbonate-polymer bounded, 90 mg) for 2 hours, filtered and concentrated giving compound 8q as an off white solid in 33% isolated yield. $^1$HNMR (500 MHz, DMSO-$d_6$) δ ppm: 11.78 (b, 1H), 11.29 (b, 1H), 8.30 (d, 1H), 8.25 (d, 1H), 7.48 (d, 1H), 7.40 (t, 1H), 7.31 (s, 1H), 7.10-7.06 (m, 2H). 7.01 (d, 1H), 6.56 (d, 1H). Mass (m/z): 234.2 (M+H). Purity: 97.6% by HPLC.

Synthesis of compound 8q-1

Potassium t-butoxide (6.7 g, 60 mmol) is added to a stirred 0° C. solution of compound 8q (46 mmol) in DMF (150 mL). After stirring for 30 minutes, N-Boc-4-bromopiperidine (60 mmol) is added and the mixture is stirred at approximately 25° C. until complete. The mixture is diluted with ether and water. The layers are separated, and the aqueous portion is extracted two more times with ether. The organic portions are combined and washed with brine and then dried over anhydrous sodium sulfate. The mixture is filtered and the solvent is removed in vacuo. The crude product is purified on silica gel giving compound 8q-1.

Synthesis of compound 9q

To a solution of compound 8q-1 (0.076 mmol) in MeOH (3 mL) is added methanolic HCl (prepared by bubbling HCl gas into MeOH, 3 mL) dropwise and with stirring. After addition, stirring is continued at room temperature for 2 hours after which, the mixture is concentrated in vacuo giving compound 9q HCl salt. This material is treated with MP-carbonate (tetra alkyl ammonium carbonate-polymer bounded, 90 mg) for 2 hours, filtered and concentrated giving compound 9q as its free base.

Example 19

An exemplary procedure for the preparation of intermediate compound 9r.

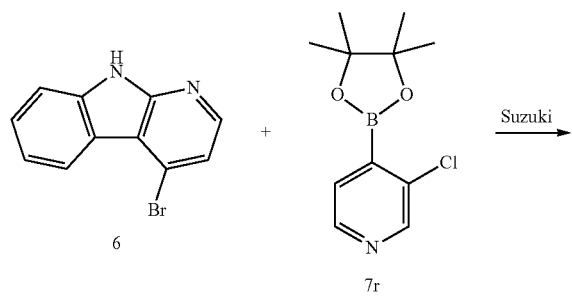

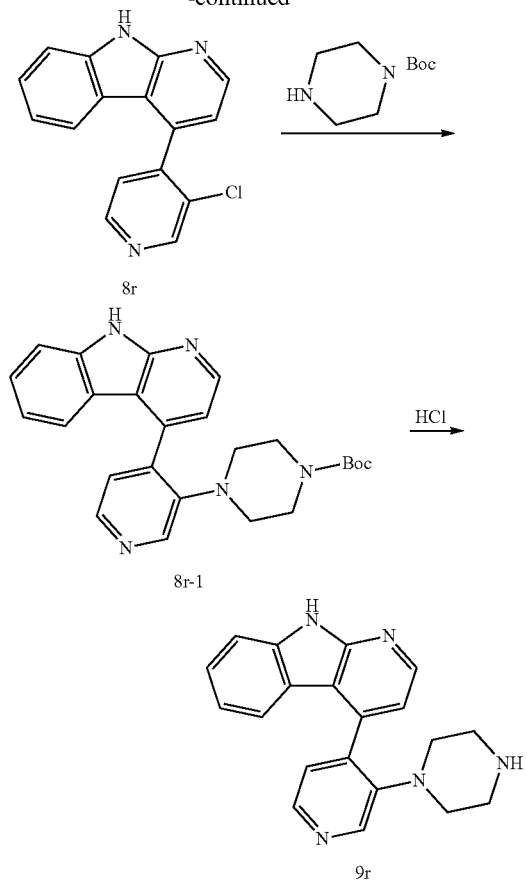

Synthesis of compound 8r

A solution of compound 6 (100 mg, 0.404 mmol), boronate ester 7r (143 mg, 0.60 mmol), aqueous sodium carbonate solution (2.0M, 1 mL, 2.0 mmol) and DME (4 mL) was purged with nitrogen and Pd(PPh$_3$)$_4$ (50 mg, 0.04 mmol) was added. The resulting mixture was stirred in a microwave reactor at 150° C. for 90 min. After cooling to room temperature, the mixture was poured into water (20 mL) and extracted with EtOAc (2×50 mL). The combined organic phases were dried over anhydrous sodium sulfate, filtered, and concentrated in vacuo. The residue was purified on silica gel (EtOAc/Hexane 4/6) giving compound 8r in 30% isolated yield. $^1$HNMR (500 MHz, DMSO-D6) δ ppm: 12.15 (b, 1H), 8.8 (s, 1H), 8.58 (d, 1H), 7.62 (d, 1H), 7.54 (d, 1H), 7.52 (m, 1H), 7.12 (d, 1H), 6.81-7.91 (m, 2H). Mass (m/z): 280.2. Purity: 90.84% by HPLC.

Synthesis of compound 8r-1

To a solution of compound 8r (0.05 mmol) in THF (0.5 mL) is added Boc-piperazine (0.5 mmol). A freshly prepared solution of LDA in THF (2.1 M, 55 mL, 0.11 mmol) is then added at room temperature via syringe. The mixture is heated to reflux until all starting material is consumed. The reaction mixture is cooled to room temperature, and the solvent are removed in vacuo. The residue is extracted from water with dichloromethane, the organic layer is dried over anhydrous magnesium sulfate, and the solvent is removed in vacuo. The crude mixture is purified on silica gel giving compound 8r-1.

Synthesis of compound 9r

To a solution of compound 8r-1 in MeOH (3 mL) is added methanolic HCl (prepared by bubbling HCl gas into MeOH, 3 mL) dropwise and with stirring. After addition, stirring is continued at room temperature for 2 hours after which, the mixture is concentrated in vacuo giving compound 9r HCl salt. This material is treated with MP-carbonate (tetra alkyl ammonium carbonate-polymer bounded, 90 mg) for 2 hours, filtered and concentrated giving compound 9r as its free base.

Example 20

An exemplary procedure for the preparation of intermediate compound 9s.

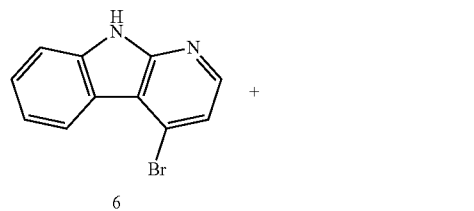

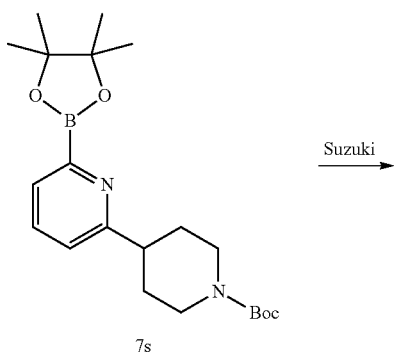

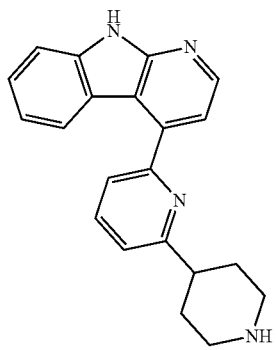

Synthesis of compound 8s

A solution of compound 6 (0.405 mmol), boronate ester 7s (0.608 mmol), aqueous sodium carbonate (2.0M, 1 mL, 2.0 mmol) and DME (4 mL) is purged with nitrogen and Pd(PPh$_3$)$_4$ (50 mg, 0.04 mmol) is added. The resulting mixture is stirred in a microwave reactor at 150° C. for 90 min. After cooling to room temperature, the mixture is poured into water (20 ml) and extracted with EtOAc (2×50 mL). The combined organic phases are dried over anhydrous sodium sulfate, filtered, and concentrated in vacuo. Purification on silica gel gives compound 8s.

Synthesis of compound 9s

To a suspension of compound 8s (0.202 mmol) in MeOH (3 mL) is added methanolic HCl (prepared by bubbling HCl gas into MeOH, 3 mL) dropwise and with stirring. After addition, stirring is continued at room temperature for 2 hours after which, the mixture is concentrated in vacuo giving compound 9s HCl salt. This material is treated with MP-carbonate (tetra alkyl ammonium carbonate-polymer bounded) for 2 hours, filtered and concentrated giving compound 9s.

Example 21

An exemplary procedure for the preparation of intermediate compound 9t.

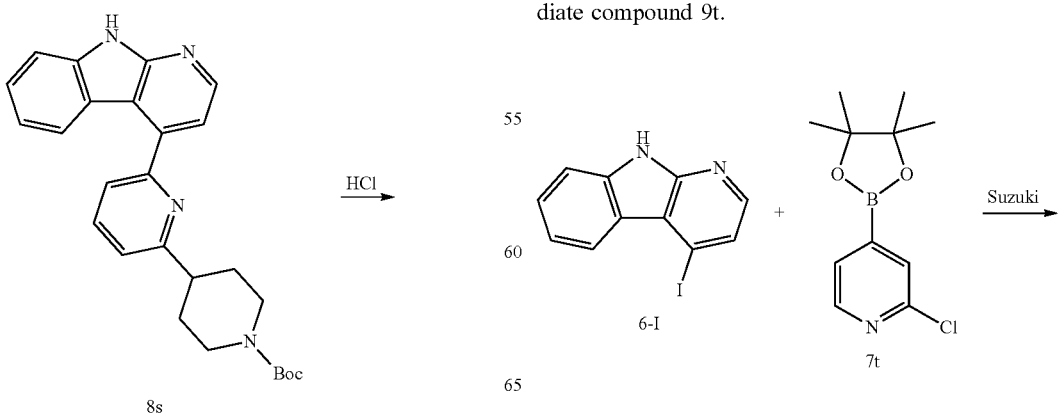

79

-continued

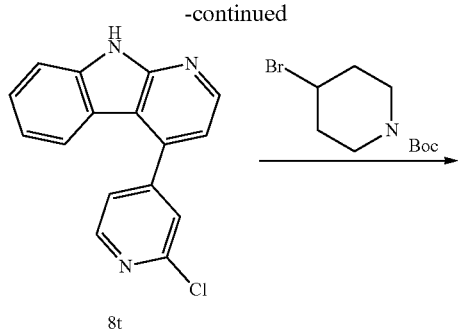

8t

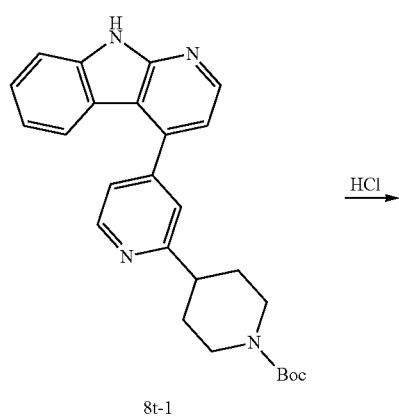

8t-1

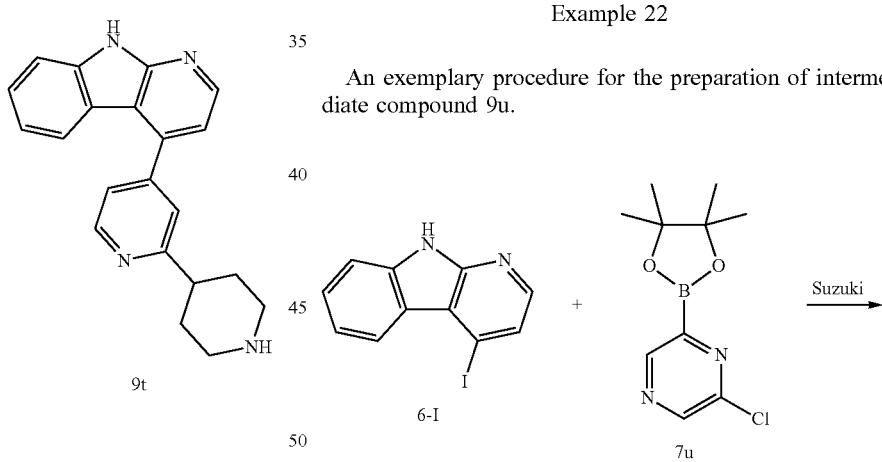

9t

Synthesis of compound 8t

A solution of compound 6-I (175 mg, 0.595 mmol), boronate ester 7t (171 mg, 0.714 mmol), aqueous sodium carbonate (2.0M, 0.6 mL, 1.2 mmol) and DME (5 mL) was purged with nitrogen and Pd(PPh$_3$)$_4$ (80 mg, 0.064 mmol) was added. The resulting mixture was heated to 100° C. for 4 h. After cooling to room temperature, the mixture was poured into water (20 ml) and extracted with EtOAc (2×60 mL). The combined organic phases were dried over anhydrous sodium sulfate, filtered, and concentrated in vacuo. Purification on silica gel (EtOAc/Hexane 45/55) gave compound 8t in 15% yield. $^1$HNMR (500 MHz, DMSO-D6) δ ppm: 12.18 (s, 1H), 8.7 (d, 1H), 8.52 (d, 1H), 7.92 (s, 1H), 7.78 (d, 1H), 7.58 (m, 1H), 7.45 (m, 2H), 7.2 (d, 1H), 7.1 (m, 1H). Mass (m/z): 280.2. Purity: 96.36% by LC-MS.

80

Synthesis of compound 8t-1

To a flame-dried Schlenk tube equipped with a magnetic stir bar is loaded N-Boc-4-bromopiperidine (0.15 mmol, 100 mol %), followed by addition of 4,4'-di-tert-butyl-2,2'-bipyridine (0.015 mmol, 10 mol %), compound 8t (0.15 mmol, 100 mol %), and zinc powder (0.3 mmol, 200 mol %). The tube is moved into a dry glove box, at which point NiI$_2$ (0.015 mmol, 10 mol %) and MgCl$_2$ (0.15 mmol, 100 mol %) are added. The tube is capped with a rubber septum, and is moved out of the glove box. Pyridine (0.15 mmol, 100 mol %) and DMA (1.0 mL) are then added via syringe. After stirring the reaction mixture for 12 h under a nitrogen atmosphere at 25° C., it is directly loaded onto a silica column without work-up. The residue in the reaction vessel is rinsed with small amount of DCM. Flash column chromatography on silica gel gives compound 8t-1.

Synthesis of compound 9t

To a suspension of compound 8t-1 (0.202 mmol) in MeOH (3 mL) is added methanolic HCl (prepared by bubbling HCl gas into MeOH, 3 mL) dropwise and with stirring. After addition, stirring is continued at room temperature for 2 hours after which, the mixture is concentrated in vacuo giving compound 9t HCl salt. This material is treated with MP-carbonate (tetra alkyl ammonium carbonate-polymer bounded) for 2 hours, filtered and concentrated giving compound 9t.

Example 22

An exemplary procedure for the preparation of intermediate compound 9u.

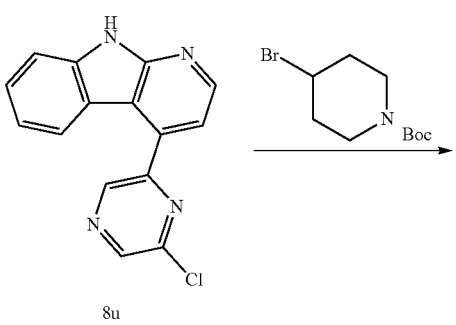

8u

-continued

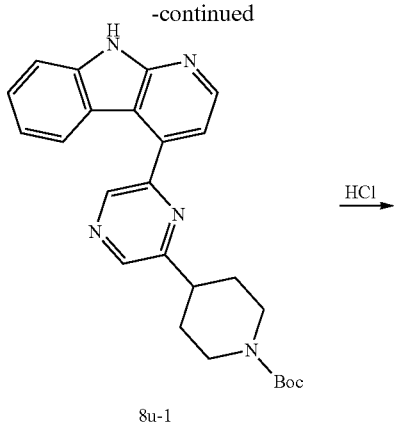

8u-1

↓ HCl

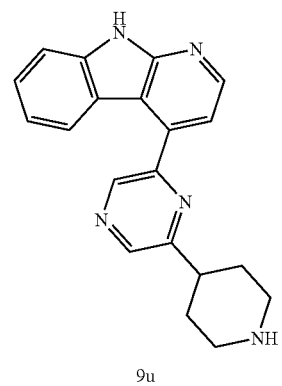

9u

Synthesis of compound 8u

A solution of compound 6-I (125 mg, 0.425 mmol), boronate ester 7u (200 mg, 0.831 mmol), aqueous sodium carbonate (2.0M, 0.7 mL, 1.4 mmol) and DME (5 mL) was purged with nitrogen and Pd(PPh$_3$)$_4$ (96 mg, 0.076 mmol) was added. The resulting mixture was heated to 100° C. for 4 h. After cooling to room temperature, the mixture was poured into water (25 ml) and extracted with EtOAc (2×55 mL). The combined organic phases were dried over anhydrous sodium sulfate, filtered, and concentrated in vacuo. Purification on silica gel (EtOAc/Hexane 4/6) gave compound 8u in 16.6% yield. $^1$HNMR (500 MHz, DMSO-D6) δ ppm: 12.19 (s, 1H), 9.21 (s, 1H), 9.0 (s, 1H), 8.58 (d, 1H), 7.9 (d, 1H), 7.58 (m, 1H), 7.45 (m, 2H), 7.15 (m, 1H). Mass (m/z): 281.2. Purity: 95% by LC-MS.

Synthesis of compound 8u-1

To a flame-dried Schlenk tube equipped with a magnetic stir bar is loaded N-Boc-4-bromopiperidine (0.15 mmol, 100 mol %), followed by addition of 4,4'-di-tert-butyl-2,2'-bipyridine (0.015 mmol, 10 mol %), compound 8u (0.15 mmol, 100 mol %), and zinc powder (0.3 mmol, 200 mol %). The tube is moved into a dry glove box, at which point NiI$_2$ (0.015 mmol, 10 mol %) and MgCl$_2$ (0.15 mmol, 100 mol %) are added. The tube is capped with a rubber septum, and is moved out of the glove box. Pyridine (0.15 mmol, 100 mol %) and DMA (1.0 mL) are then added via syringe. After stirring the reaction mixture for 12 h under a nitrogen atmosphere at 25° C., it is directly loaded onto a silica column without work-up. The residue in the reaction vessel is rinsed with small amount of DCM. Flash column chromatography on silica gel gives compound 8u-1.

Synthesis of compound 9u

To a suspension of compound 8u (0.202 mmol) in MeOH (3 mL) is added methanolic HCl (prepared by bubbling HCl gas into MeOH, 3 mL) dropwise and with stirring. After addition, stirring is continued at room temperature for 2 hours after which, the mixture is concentrated in vacuo giving compound 9u HCl salt. This material is treated with MP-carbonate (tetra alkyl ammonium carbonate-polymer bounded) for 2 hours, filtered and concentrated giving compound 9u.

Example 23

An exemplary procedure for the preparation of intermediate compound 9v.

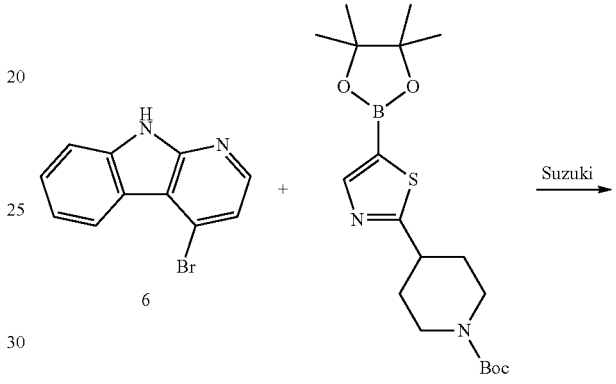

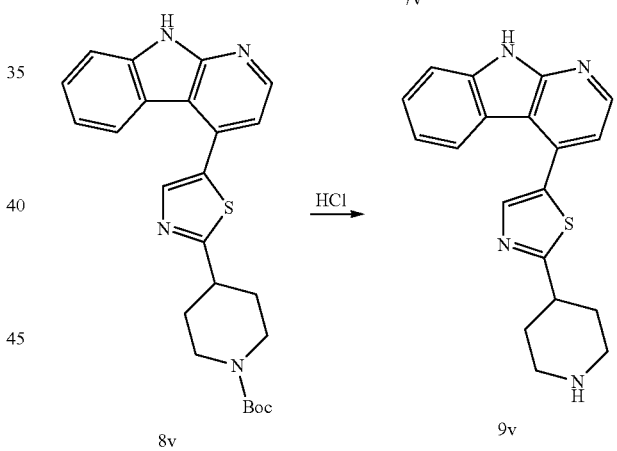

Synthesis of compound 8v

A solution of compound 6 (0.405 mmol), boronate ester 7v (0.60 mmol), aqueous sodium carbonate (2.0M, 1 mL, 2.0 mmol) and DME (4 mL) is purged with nitrogen and Pd(PPh$_3$)$_4$ (50 mg, 0.04 mmol) is added. The resulting mixture is stirred in a microwave reactor at 150° C. for 90 min. After cooling to room temperature, the mixture is poured into water (20 ml) and extracted with EtOAc (2×50 mL). The combined organic phases are dried over anhydrous sodium sulfate, filtered, and concentrated in vacuo. Purification on silica gel gives compound 8v.

Synthesis of compound 9v

To a suspension of compound 8v (0.185 mmol) in MeOH (3 mL) is added methanolic HCl (prepared by bubbling HCl gas into MeOH, 3 mL) dropwise and with stirring. After addition, stirring is continued at room temperature for 2 hours after which, the mixture is concentrated in vacuo giving 90 mg of compound 9v HCl salt. This material is treated with MP-carbonate (tetra alkyl ammonium carbonate-polymer bounded) for 2 hours, filtered and concentrated giving compound 9v.

Example 24

An exemplary procedure for the preparation of intermediate compound 9w.

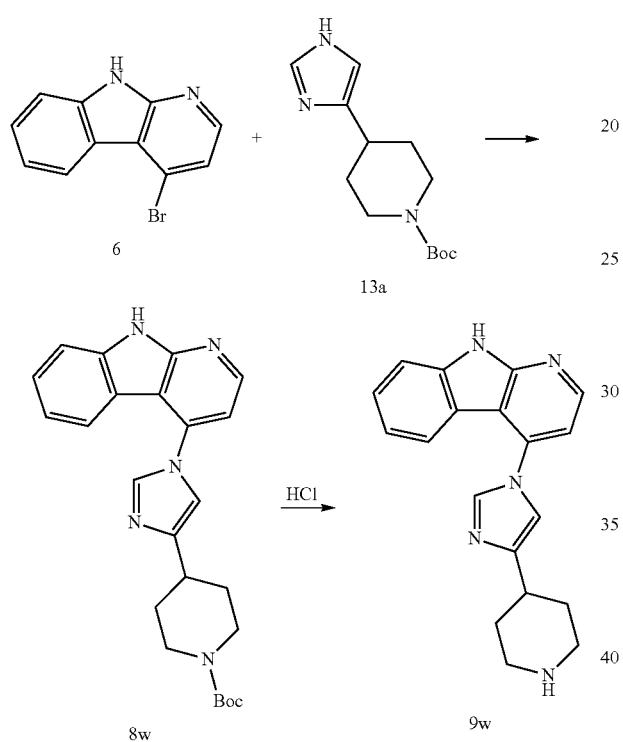

Synthesis of compound 9w

A mixture of 6-I (100 mg, 0.34 mmol), compound 7o (170 mg, 0.68 mmol), potassium carbonate (100 mg, 0.68 mmol) and imidazole (80 mg, 1.02 mmol) was stirred in a microwave reactor at 200° C. for 1 h. After cooling to room temperature, the mixture was poured into water (10 mL) and extracted with EtOAc (2×30 mL). The combined organic phases were dried over anhydrous sodium sulfate, filtered and concentrated in vacuo. Purification on silica gel (EtOAc/Hexane 6/4) gave compound 9w (13.9% yield) with the Boc protecting group having been cleaved during the coupling reaction thus bypassing isolation of intermediate compound 8w. Mass (m/z): 318.3 (M+H). Purity: 73.42% by LC-MS.

Example 25

An exemplary procedure for the preparation of intermediate compound 9x.

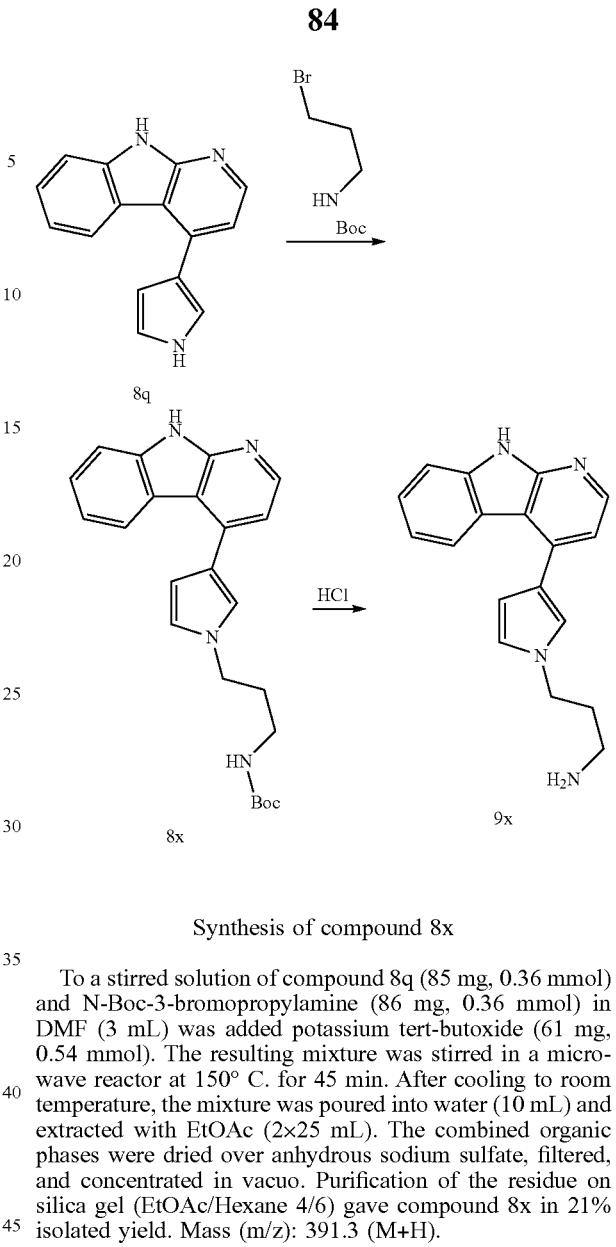

Synthesis of compound 8x

To a stirred solution of compound 8q (85 mg, 0.36 mmol) and N-Boc-3-bromopropylamine (86 mg, 0.36 mmol) in DMF (3 mL) was added potassium tert-butoxide (61 mg, 0.54 mmol). The resulting mixture was stirred in a microwave reactor at 150° C. for 45 min. After cooling to room temperature, the mixture was poured into water (10 mL) and extracted with EtOAc (2×25 mL). The combined organic phases were dried over anhydrous sodium sulfate, filtered, and concentrated in vacuo. Purification of the residue on silica gel (EtOAc/Hexane 4/6) gave compound 8x in 21% isolated yield. Mass (m/z): 391.3 (M+H).

Synthesis of compound 9x

To a solution of compound 8x (30 mg, 0.076 mmol) in MeOH (2 mL) was added methanolic HCl (prepared by bubbling HCl gas into MeOH, 2 mL) dropwise and with stirring. After addition, stirring was continued at room temperature for 2 hours after which, the mixture was concentrated in vacuo giving compound 9x HCl salt. This material was treated with MP-carbonate (tetra alkyl ammonium carbonate-polymer bounded, 40 mg) for 2 hours, filtered and concentrated giving compound 9x (10 mg, 45.4% yield) as a pale brown solid. $^1$HNMR (500 MHz, DMSO-D6) δ ppm: 11.32 (s, 1H), 8.40-8.22 (m, 2H), 7.71 (d, 1H), 7.5 (t, 1H), 7.31 (d, 1H), 7.20-7.05 (m, 2H), 7.02 (d, 1H), 6.58 (s, 1H), 4.6-4.52 (t, 2H), 2.51 (t, 2H), 1.90 (m, 2H). Mass (m/z): 291.2 (M+H). Purity: 92.87% by HPLC.

Example 26

An exemplary procedure for the preparation of intermediate compound 9y.

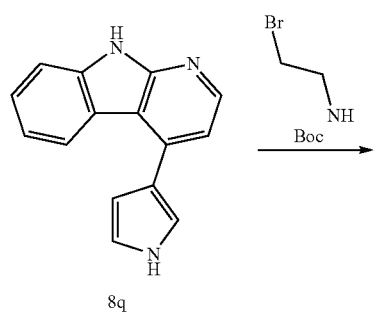

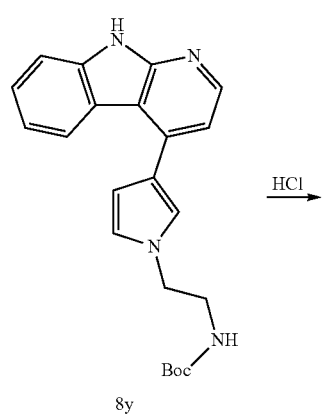

Synthesis of compound 8y

Potassium t-butoxide (6.7 g, 60 mmol) is added to a stirred 0° C. solution of compound 8q (Example 18, 46 mmol) in DMF (150 mL). After stirring for 30 minutes, N-Boc-2-bromoethylamine (60 mmol) is added and the mixture is stirred at approximately 25° C. until complete. The mixture is diluted with ether and water. The layers are separated, and the aqueous portion is extracted two more times with ether. The organic portions are combined and washed with brine and then dried over anhydrous sodium sulfate. The mixture is filtered and the solvent is removed in vacuo. The crude product is purified on silica gel giving compound 8y.

Synthesis of compound 9y

To a solution of compound 8y (0.076 mmol) in MeOH (3 mL) is added methanolic HCl (prepared by bubbling HCl gas into MeOH, 3 mL) dropwise and with stirring. After addition, stirring is continued at room temperature for 2 hours after which, the mixture is concentrated in vacuo giving compound 9y HCl salt. This material is treated with MP-carbonate (tetra alkyl ammonium carbonate-polymer bounded, 90 mg) for 2 hours, filtered and concentrated giving compound 9y as its free base.

Example 27

An exemplary procedure for the preparation of compound I-7.

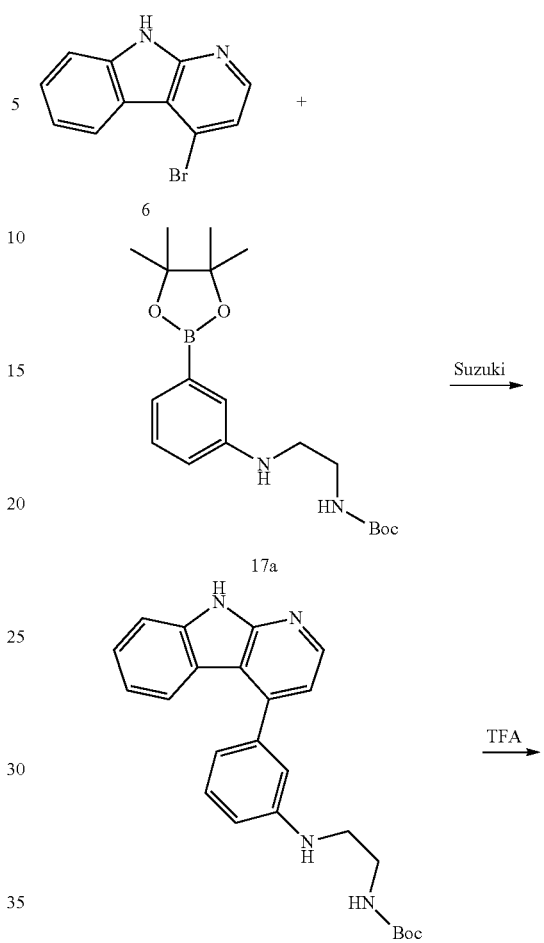

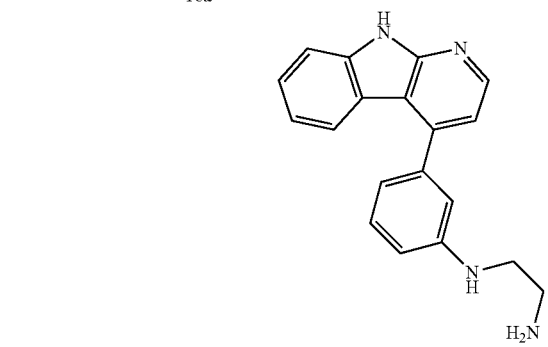

Synthesis of tert-butyl 2-(3-(9H-pyrido[2,3-b]indol-4-yl)phenylamino)ethylcarbamate (18a)

A solution of compound 6 (250 mg, 1.01 mmol), boronate ester 17a (550 mg, 1.52 mmol), aqueous sodium carbonate (2.0M, 1 mL, 2.0 mmol) and dioxane (4 mL) was purged with nitrogen and Pd(PPh$_3$)$_4$ (58 mg, 0.05 mmol) was added. The resulting mixture was stirred in a microwave reactor at 140° C. for 45 min. After cooling to room temperature, the mixture was poured into water (30 mL) and washed with EtOAc (2×50 mL). The combined organic phases were dried over anhydrous Na$_2$SO$_4$, filtered, and concentrated in vacuo.

The crude product was purified on silica gel (40% EtOAc in hexane) giving a 40% yield of compound 18a. Mass (m/z): 403.4 (M+H).

Synthesis of N1-(3-(9H-pyrido[2,3-b]indol-4-yl)phenyl)ethane-1,2-diamine (I-7)

Trifluoroacetic acid (114 mg, 1.0 mmol) was added dropwise to a suspension of compound 18a (100 mg, 0.2 mmol) in anhydrous dichloromethane (3 mL). After stirring for 2 h at room temperature, the mixture was concentrated in vacuo giving 110 mg of compound I-7. This material was stirred with desalting resin (MP-carbonate, 150 mg) in MeOH (4 mL) for 2 h. The resin was removed by filtration and the filtrate was concentrated to dryness. Purification of the residue by preparative HPLC gave 22 mg (30% yield) of pure compound I-7. $^1$H NMR (500 MHz, DMSO-$d_6$) δ ppm: 11.9 (br, 1H), 8.41 (d, 1H), 7.8 (br, 2H), 7.64 (d, 1H), 7.49 (d, 1H), 7.39 (t, 1H), 7.33 (m, 1H), 7.04 (m, 2H), 6.78-6.85 (m, 3H), 6.0 (br, 1H), 3.25 (t, 2H), 2.97 (t, 2H). Mass (m/z): 303.2 (M+H). Purity: 98.4% by HPLC.

Example 28

An exemplary procedure for the preparation of compound I-8:

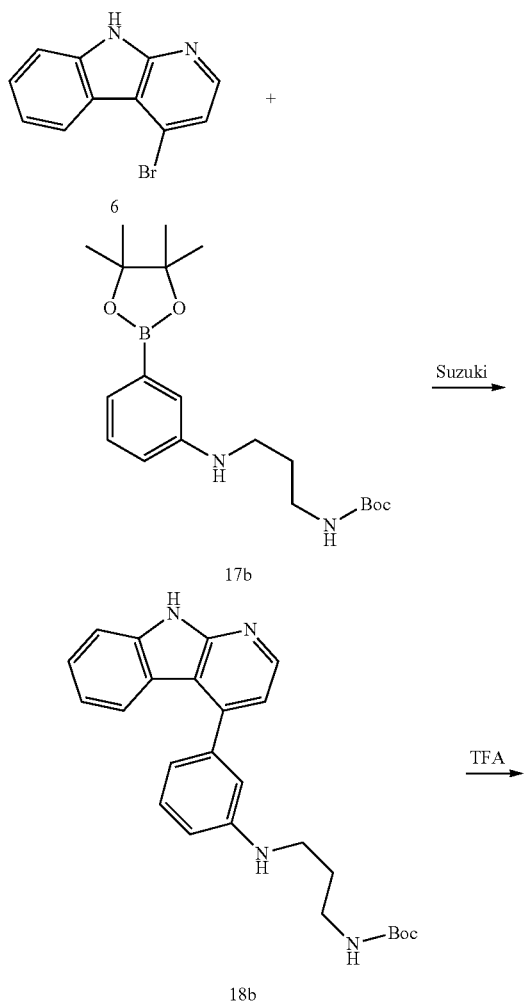

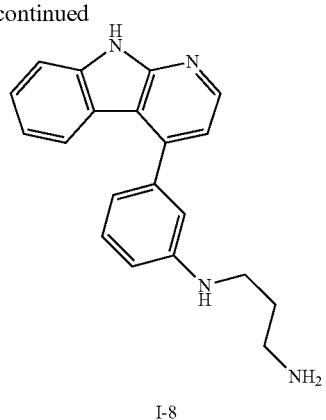

I-8

Synthesis of tert-butyl 2-(3-(9H-pyrido[2,3-b]indol-4-yl)phenylamino)propylcarbamate (18b)

Compound 18b was prepared according to the procedure for compound 18a (Example 27) using compound 6 (100 mg, 0.405 mmol), compound 17b (228 mg, 0.60 mmol), Pd(PPh$_3$)$_4$ (23 mg, 0.025 mmol) and proportionate molar equivalents of aqueous sodium carbonate and dioxane. 80 mg (47% yield) of compound 18b were isolated. Mass (m/z): 417.4 (M+H). Purity: 98.2% by HPLC.

Synthesis of N1-(3-(9H-pyrido[2,3-b]indol-4-yl)phenyl)propane-1,2-diamine (I-8)

Compound I-8 was prepared according the procedure for compound I-7 (Example 27) using compound 18b (80 mg, 0.19 mmol) and trifluoroacetic acid (109 mg, 0.95 mmol). 12 mg (20% yield) of compound I-8 were isolated. $^1$H NMR (500 MHz, DMSO-$d_6$) δ ppm: 11.91 (br, 1H), 8.41 (d, 1H), 7.7 (br, 2H), 7.64 (d, 1H), 7.49 (d, 1H), 7.41 (t, 1H), 7.31 (t, 1H), 7.04-7.06 (m, 2H), 6.83 (d, 1H), 6.78 (d, 1H), 5.94 (br, 1H), 3.31 (t, 2H), 2.90 (t, 2H), 1.83-1.85 (m, 2H). Mass (m/z): 317.3 (M+H).

Example 29

An exemplary procedure for the preparation of compound I-6:

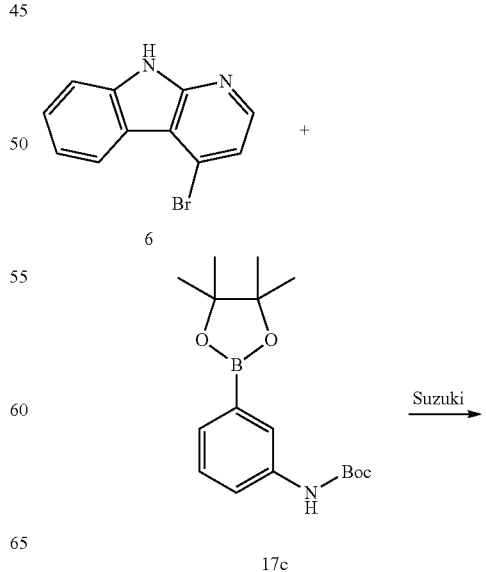

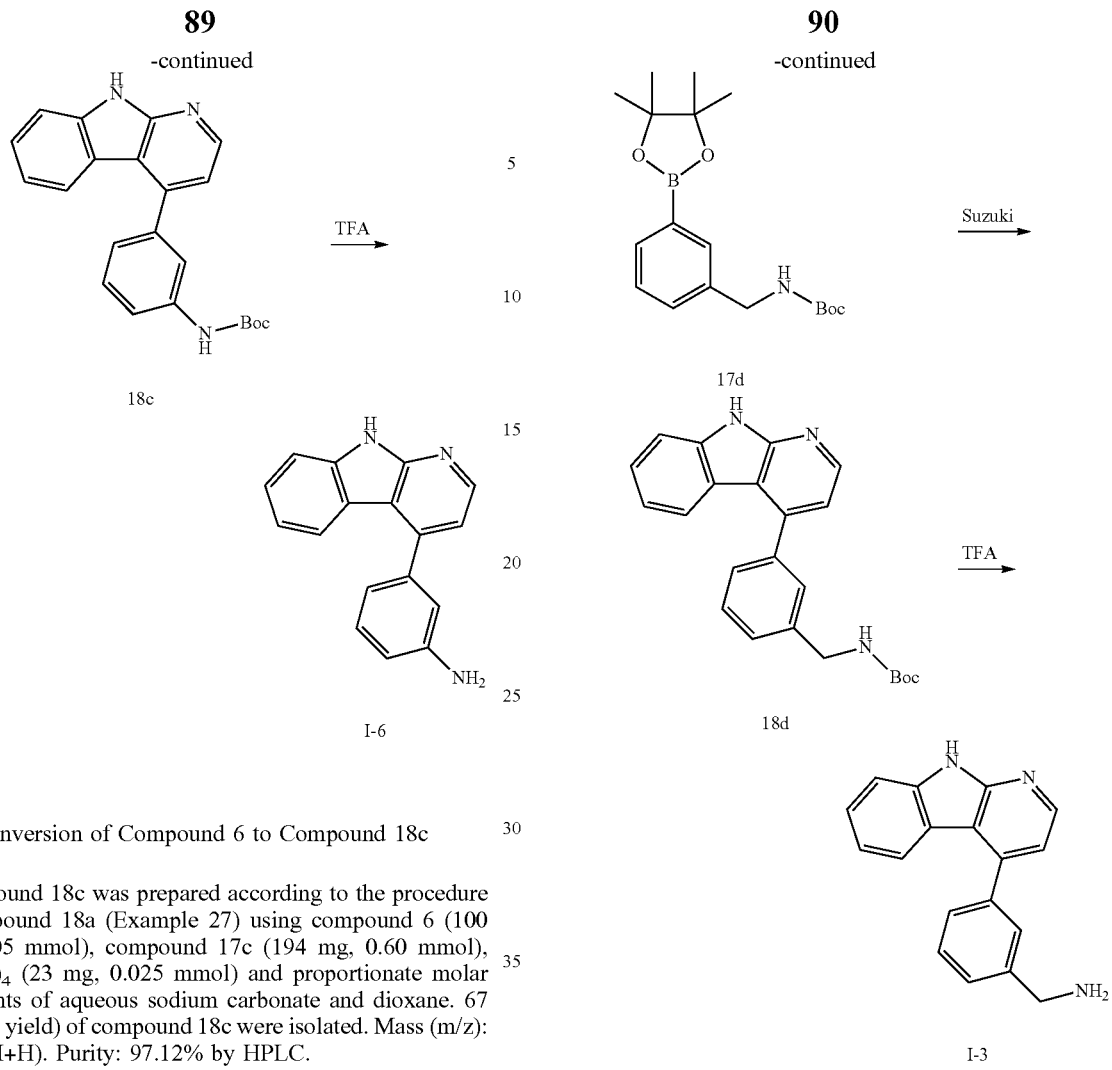

Conversion of Compound 6 to Compound 18c

Compound 18c was prepared according to the procedure for compound 18a (Example 27) using compound 6 (100 mg, 0.405 mmol), compound 17c (194 mg, 0.60 mmol), Pd(PPh$_3$)$_4$ (23 mg, 0.025 mmol) and proportionate molar equivalents of aqueous sodium carbonate and dioxane. 67 mg (46% yield) of compound 18c were isolated. Mass (m/z): 360.4 (M+H). Purity: 97.12% by HPLC.

Conversion of Compound 18c to Compound I-6

Compound I-6 was prepared according to the procedure for compound I-7 (Example 27) using compound 18c (67 mg, 0.18 mmol) and trifluoroacetic acid (106 mg, 0.90 mmol). 22 mg (45% yield) of compound I-6 were isolated. $^1$H NMR (500 MHz, DMSO-d$^6$) δ ppm: 11.89 (br, 1H), 8.41 (d, 1H), 7.66 (d, 2H), 7.50 (d, 1H), 7.48 (d, 1H), 7.39 (t, 1H), 7.22 (t, 1H), 7.03 (m, 2H), 6.83 (s, 1H), 6.75 (m, 2H), 5.30 (br, 2H). Mass (m/z): 260.3 (M+H).

Example 30

An exemplary procedure for the preparation of compound I-3:

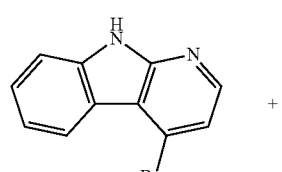

Conversion of Compound 6 to Compound 18d

Compound 18d was prepared according to the procedure for compound 18a (Example 27) using compound 6 (100 mg, 0.405 mmol), compound 17d (199 mg, 0.60 mmol), Pd(PPh$_3$)$_4$ (23 mg, 0.025 mmol) and proportionate molar equivalents of aqueous sodium carbonate and dioxane. 75 mg (50% yield) of compound 18d were isolated. Mass (m/z): 374.4 (M+H). Purity: 95.5% by HPLC.

Conversion of Compound 8c to Compound I-3

Compound I-3 was prepared according to the procedure for compound I-7 (Example 27) using compound 18d (75 mg, 0.2 mmol), and trifluoroacetic acid (118 mg, 0.90 mmol). 12 mg (20% yield) of compound I-3 were isolated. $^1$H NMR (500 MHz, DMSO-d$^6$) δ PPM: 11.89 (br, 1H), 8.48 (d, 1H), 7.77 (s, 1H), 7.65-7.68 (m, 3H), 7.53 (dd, 2H), 7.42 (t, 1H), 7.10 (d, 1H), 7.09 (t, 1H), 4.12 (s, 2H). Mass (m/z): 274.3 (M+H).

Example 31

An exemplary procedure for the preparation of compound I-4:

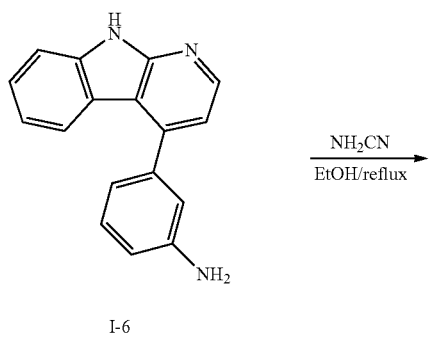

I-6

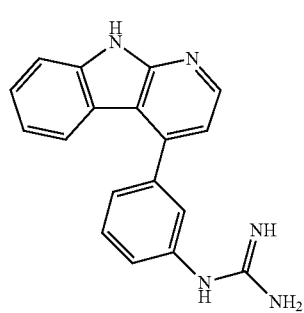

I-4

To a solution of I-6 (30 mg, 0.115 mmol) in ethanol (2 mL) was added NH$_2$CN (29 mg, 6 eq.). The mixture was refluxed for 2 days after which, the volatiles were removed under reduced pressure. The resulting crude residue was dissolved in water and the pH was adjusted to ~10 using aqueous 2N NaOH. The aqueous mixture was extracted with EtOAc (5 mL). The organic phase was dried over Na$_2$SO$_4$, concentrated and purified by preparative HPLC giving compound I-4 (4 mg, 12% yield) as a yellow solid. Mass (m/z): 302.3 (M+H). Purity: 90.05% by HPLC.

Example 32

An exemplary procedure for the preparation of compound I-5:

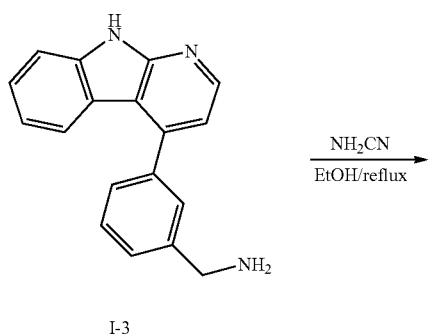

I-3

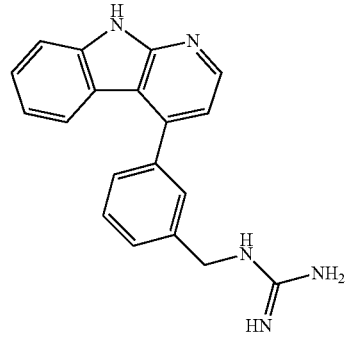

I-5

Compound I-5 was prepared according to the preparation of compound I-4 (Example 31) using compound I-3 (40 mg, 0.146 mmol) and NH$_2$CN (35 mg, 6 eq.). 4 mg (8.6% yield) of compound I-5 were isolated. Mass (m/z): 316.4 (M+H). Purity: 98.1% by HPLC.

Example 33

An exemplary procedure for the preparation of compound I-2:

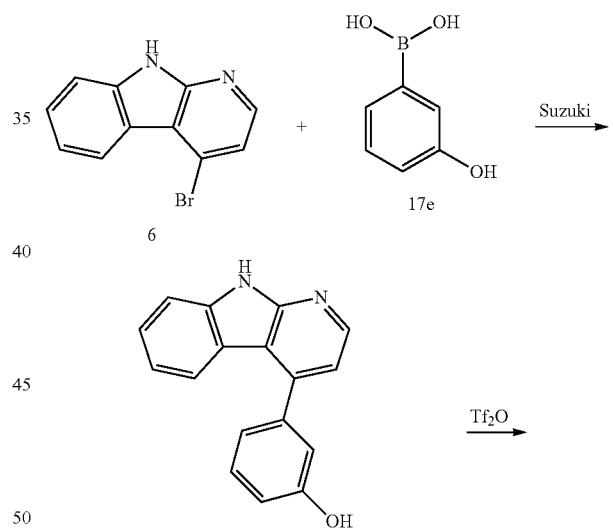

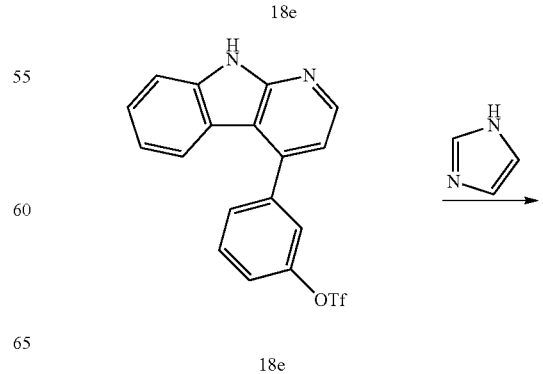

18e

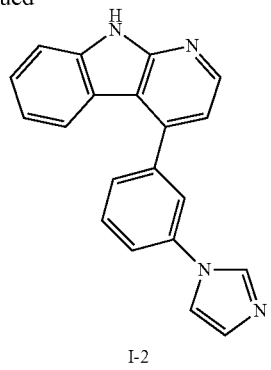

I-2

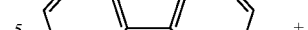

6

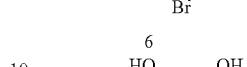

17f

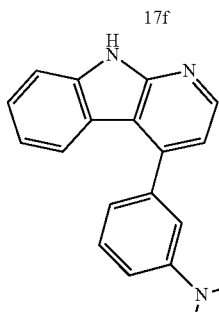

18f

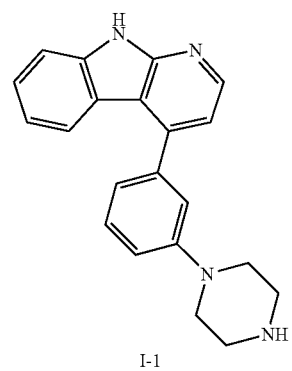

I-1

Preparation of Compound 18e

A solution of compound 6 (250 mg, 1.01 mmol), 3-hydroxyphenylboronic acid 17e (167 mg, 1.2 mmol) and aqueous sodium carbonate (2 M, 1 mL, 2.0 mmol) in dioxane (4 mL) was purged with nitrogen. Pd(PPh$_3$)$_4$ (58 mg, 0.05 mmol) was added and the resulting mixture was stirred at 90° C. for 5 h. After cooling to room temperature, the mixture was poured into water (30 mL) and extracted with EtOAc (2×50 mL). The combined organic phases were dried over Na$_2$SO$_4$, filtered, and concentrated to dryness. The residue was purified on silica gel (40% EtOAc/hexane) giving compound 18e (50% yield). $^1$H NMR (500 MHz, DMSO-d$_6$) δ ppm: 11.89 (br, 1H), 9.68 (br, 1H), 8.42 (d, 1H), 7.58 (d, 1H), 7.49 (d, 1H), 7.39 (m, 2H), 7.04 (m, 4H), 6.92 (d, 1H). Mass (m/z): 261.3 (M+H).

Synthesis of 3-(9H-pyrido[2,3-b]indol-4-yl)phenyl trifluoromethanesulfonate (19e)

To a solution of compound 18e (200 mg, 0.7 mmole) in dichloromethane (5 mL) at 0° C. was added triethylamine (0.26 mL, 1.9 mmole). After stirring for 5-10 min, triflic anhydride (0.2 mL, 1.5 mmole) was added dropwise. Stirring was continued at room temperature for 2 h after which the reaction was concentrated to dryness and the residue was purified on silica gel (20% EtOAc/hexane) giving compound 19e (150 mg, 33% Yield). Mass (m/z): 393.3 (M+H).

Synthesis of 4-(3-(1H-imidazol-1-yl)phenyl)-9H-pyrido[2,3-b]indole (I-2)

A mixture of compound 19e (150 mg, 0.38 mmol), imadazole (77 mg, 1.14 mmol), palladium(II)acetate (9 mg, 10 mol %), BINAP (24 mg, 10 mol %) and cesium carbonate (250 mg, 0.76 mmol) in THF (4 mL) was stirred in a microwave reactor at 150° C. for 45 min. The mixture was filtered through Celite and the Celite pad was washed with EtOAc. The combined filtrate was concentrated to dryness and the crude product was purified by preparative HPLC to give compound I-2 (7 mg, 5.8% yield) as an off white solid. Mass (m/z): 311.2 (M+H). Purity: 99.2% by HPLC.

Example 34

An exemplary procedure for the preparation of compound I-1:

Synthesis of tert-butyl 4-(3-(9H-pyrido[2,3-b]indol-4-yl)phenyl)piperazine-1-carboxylate (18f)

Compound 18f was prepared according to the procedure for compound 18e (Example 33) using compound 6 (100 mg, 0.405 mmol), compound 17f (148 mg, 0.48 mmol) and Pd(PPh$_3$)$_4$ (23 mg, 0.025 mmol). 90 mg (52% yield) of compound 18f were isolated. $^1$H NMR (500 MHz, DMSO-d$_6$) δ ppm: 11.94 (br, 1H), 8.45 (d, 1H), 7.50-7.58 (m, 3H), 7.42 (t, 1H), 7.25 (s, 1H), 7.19-7.21 (m, 3H), 7.03 (t, 1H), 3.20 (t, 4H), 3.47 (t, 4H), 1.41 (s, 9H). Mass (m/z): 429.3 (M+H).

95

Synthesis of 4-(3-(piperazin-1-yl)phenyl)-9H-pyrido[2,3-b]indole (I-1)

Compound I-1 was prepared according to the procedure for compound I-7 (Example 27) using compound 18f (75 mg, 0.2 mmol) and trifluoroacetic acid (118 mg, 0.90 mmol). 12 mg (20% yield) of compound I-1 were isolated. $^1$H NMR (500 MHz, DMSO-d$^6$) δ ppm: 11.97 (br, 1H), 8.87 (b, 1H), 8.45 (d, 1H), 7.54-7.58 (m, 3H), 7.42 (d, 1H), 7.25 (s, 1H), 7.19-7.21 (m, 3H), 7.03 (t, 1H), 3.26 (t, 4H), 3.37 (t, 4H).

Example 35

An exemplary procedure for the preparation of compound I-9:

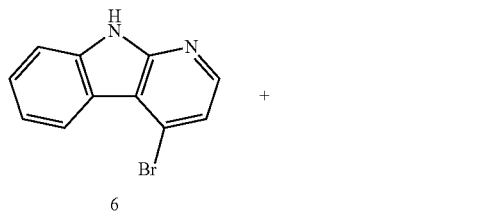

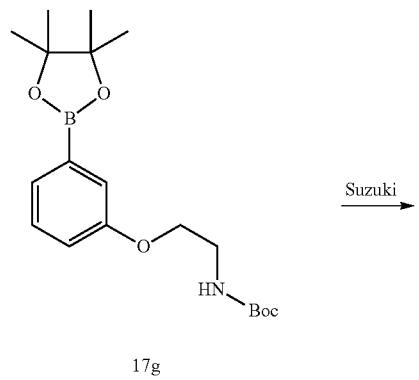

96

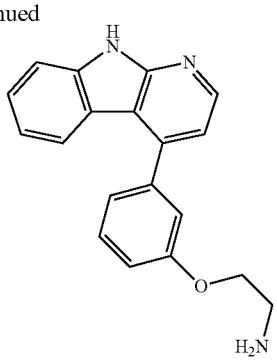

I-9

Synthesis of tert-butyl 2-(3-(9H-pyrido[2,3-b]indol-4-yl)phenoxy)ethyl carbamate (18g)

A mixture of compound 6 (100 mg, 0.40 mmol), compound 17g (220 mg, 0.60 mmol), aqueous sodium carbonate (2 M, 1 mL, 2.0 mmol) in dioxane (4 mL) was purged with nitrogen. Pd(PPh$_3$)$_4$ (23 mg, 0.02 mmol) was added and the resulting mixture was stirred in a microwave reactor at 140° C. for 45 min. After cooling to room temperature, the mixture was poured into water (10 mL) and extracted with EtOAc (2×25 mL). The combined organic layers were dried over Na$_2$SO$_4$, filtered, and concentrated to dryness. The residue was purified on silica gel (40% EtOAc/hexane) giving compound 18g (50% yield). Mass (m/z): 404.4 (M+H).

Synthesis of 2-(3-(9H-pyrido[2,3-b]indol-4-yl)phenoxy)ethanamine (I-9)

To a solution of compound 18g (100 mg, 0.24 mmol) in anhydrous dichloromethane (3 mL) was added trifluoroacetic acid (141 mg, 1.2 mmol) dropwise. After stirring at room temperature for 2 h, the reaction was concentrated to dryness. The residue was stirred with MP-carbonate resin (150 mg) in MeOH (5 mL) for 2 h. The resin was removed by filtration. The filtrate was concentrated to dryness and the residue was purified by preparative HPLC giving compound I-9 (14 mg, 18% yield) as a off white solid. $^1$H NMR (500 MHz, DMSO-d$_6$) δ PPM: 11.98 (br, 1H), 8.43 (d, 1H), 7.98 (br, 2H), 7.55 (m, 3H), 7.40 (t, 1H), 7.29 (d, 1H), 7.24 (s, 1H), 7.18 (d, 2H), 7.08 (d, 3H), 7.02 (t, 1H). Mass (m/z): 304.3 (M+H).

Example 36

An exemplary procedure for the preparation of compound I-10:

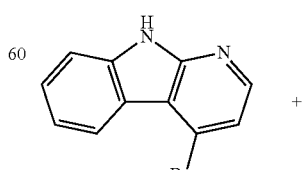

97

-continued

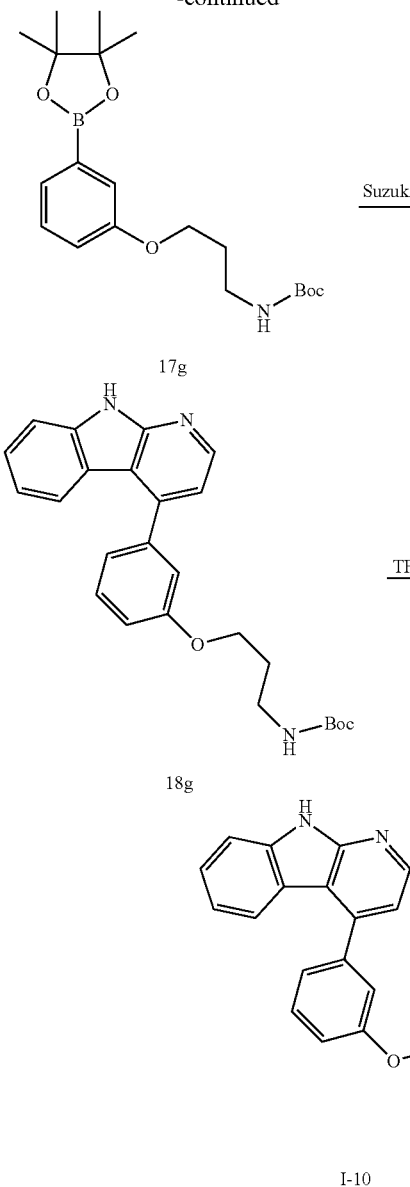

Synthesis of tert-butyl 3-(3-(9H-pyrido[2,3-b]indol-4-yl)phenoxy)propylcarbamate (18h)

Compound 18h was prepared according to the procedure for compound 11g (Example 35) using compound 6 (100 mg, 0.40 mmol), compound 17h (229 mg, 0.60 mmol), aqueous sodium carbonate (2 M, 1 mL, 2.0 mmol) and Pd(PPh$_3$)$_4$ (23 mg, 0.02 mmol) in dioxane (4 mL). Compound 18h was isolated in 54% yield. Mass (m/z): 418.4 (M+H).

Synthesis of 3-(3-(9H-pyrido[2,3-b]indol-4-yl)phenoxy)propan-1-amine (I-10)

Compound I-10 was prepared according to the procedure for compound I-9 (Example 9) using compound 18h (100 mg, 0.23 mmol) and trifluoroacetic acid (136 mg, 1.2 mmol) in anhydrous dichloromethane (3 mL). The crude product was purified by preparative HPLC giving compound I-10

98

(13 mg, 17% yield) as an off white solid. $^1$HNMR (500 MHz, DMSO-d$_6$) δ PPM: 11.97 (br, 1H), 8.44 (d, 1H), 7.80 (br, 2H), 7.51-7.54 (m, 2H), 7.39 (t, 1H), 7.25 (d, 1H), 7.19 (s, 1H), 7.08 (d, 2H), 7.07 (dd, 2H), 7.02 (t, 1H); 4.12 (t, 2H), 2.99 (m, 2H), 2.01 (t, 2H). Mass (m/z): 318.3 (M+H). Purity: 97.02% by HPLC.

Example 37

Scheme for the Preparation of compounds 6a, 6b, 6c and 6d:

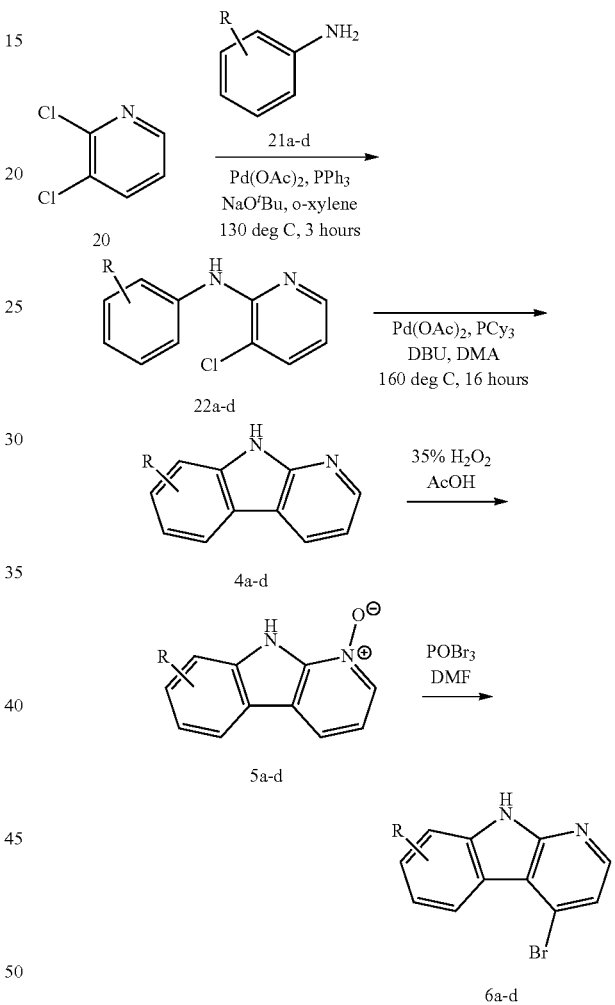

R = m-CH$_3$ (21a)
p-CH$_3$ (21b)
p-Cl (21c)
m-OCH$_3$ (21d)

General Procedure for the Synthesis of Compounds 4a-d

A mixture of 2,3-dichloro pyridine 20 (1 g, 6.76 mmol), an aniline 21 (7.43 mmol), Pd(OAc)$_2$ (98 mg, 0.065 mmol), PPh$_3$ (198 mg, 0.13 mmol) and NaO$^t$Bu (780 mg, 1.2 mmol) in o-xylene (16 mL) was sparged with nitrogen for 5 min, placed under a nitrogen atmosphere, and heated to 130° C. for 3 h in a sealed sample vial. The reaction mixture was cooled to room temperature giving compounds 22.

Pd(OAc)$_2$ (98 mg, 0.065 mmol), PCy$_3$ (200 mg, 0.1 mmol), DBU (2 g, 2 mmol) and dimethyl acetamide (16 mL) were added to the reaction vessel. The reaction mixture was sparged for 5 min, placed under a nitrogen atmosphere and heated to 160° C. for 16 h. The reaction mixture was concentrated to dryness. The residue was dissolved in ethyl acetate (2×200 mL). The mixture was washed with water (3×50 mL) and then brine (2×50 mL), dried over anhydrous Na$_2$SO$_4$, filtered and concentrated. The residue was purified on silica gel (70% EtOAc/hexane) giving compounds 4.

Example 38

An exemplary procedure for the preparation of compound 6a:

Synthesis of 7-methyl-9H-pyrido[2,3-b]indole (4a)

Compound 4a was prepared according to Example 37 using 3-methylaniline 21a (877 mg, 7.43 mmol) and proportionate molar equivalents of compound 20, Pd(OAc)$_2$, PPh$_3$, NaO$^t$Bu and o-xylene. Continuing according to Example 11, crude isolated compound 22a was converted to compound 4a using proportionate molar equivalents of Pd(OAc)$_2$, PCy$_3$, DBU and dimethyl acetamide. 480 mg (40% yield) of compound 4a were isolated. $^1$H NMR (500 MHz, DMSO-d$_6$) δ PPM: 11.61 (br, 1H), 8.41 (dd, 2H), 8.02 (d, 1H), 7.38 (s, 1H), 7.21 (d, 1H), 7.15 (d, 1H), 2.45 (s, 3H). Mass (m/z): 183.2 (M+H).

Synthesis of 7-methyl-9H-pyrido[2,3-b]indole 1-oxide (5a)

Compound 5a was prepared according to the procedure for compound 5 (Example 1) using compound 4a (370 mg, 2.02 mmol) and proportionate molar equivalents of aqueous H$_2$O$_2$ (35%) and CH$_3$COOH. 160 mg (40% yield) of compound 5a were isolated. Mass (m/z): 199.2 (M+H).

Synthesis of 4-bromo-7-methyl-9H-pyrido[2,3-b]indole (6a)

Compound 6a was prepared according to the procedure for compound 6 (Example 1) using compound 5a (155 mg, 0.782 mmol) and proportionate molar equivalents of anhydrous DMF and POBr$_3$. 61 mg (30% yield) of compound 6a were isolated. Mass (m/z): 261.1, 263.1.

Example 39

An exemplary procedure for the preparation of compound 6b:

Synthesis of 6-methyl-9H-pyrido[2,3-b]indole (4b)

Compound 4b was prepared according to Example 37 using 4-methylaniline 21b (877 mg, 7.43 mmol) and proportionate molar equivalents of compound 20, Pd(OAc)$_2$, PPh$_3$, NaO$^t$Bu and o-xylene. Continuing according to Example 11, crude isolated compound 22b was converted to compound 4b using proportionate molar equivalents of Pd(OAc)$_2$, PCy$_3$, DBU and dimethyl acetamide. 495 mg (41% yield) of compound 4b were isolated. $^1$H NMR (500 MHz, DMSO-d$_6$) δ ppm: 11.59 (br, 1H), 8.41 (d, 1H), 8.38 (d, 1H), 7.9 (s, 1H), 7.38 (d, 1H), 7.25 (d, 1H), 7.18 (t, 1H), 2.42 (s, 3H). Mass (m/z): 183.2 (M+H).

Synthesis of 6-methyl-9H-pyrido[2,3-b]indole 1-oxide (5b)

Compound 5b was prepared according to the procedure for compound 5 (Example 1) using compound 4b (420 mg, 2.29 mmol) and proportionate molar equivalents of aqueous H$_2$O$_2$ (35%) and CH$_3$COOH. 173 mg (38% yield) of compound 5b were isolated. Mass (m/z): 199.2 (M+H).

Synthesis of 4-bromo-6-methyl-9H-pyrido[2,3-b]indole (6b)

Compound 6b was prepared according to the procedure for compound 6 (Example 1) using compound 5b (170 mg, 0.857 mmol) and proportionate molar equivalents of anhydrous DMF and POBr$_3$. 69 mg (31% yield) of compound 6b were isolated. Mass (m/z): 261.1, 263.1.

Example 40

An exemplary procedure for the preparation of compound 6c:

Synthesis of 6 chloro-9H-pyrido[2,3-b]indole (4c)

Compound 4c was prepared according to Example 37 using 4-chloroaniline 21c (1.03 g, 7.43 mmol) and proportionate molar equivalents of compound 20, Pd(OAc)$_2$, PPh$_3$, NaO$^t$Bu and o-xylene. Continuing according to Example 11, crude isolated compound 22c was converted to compound 4c using proportionate molar equivalents of Pd(OAc)$_2$, PCy$_3$, DBU and dimethyl acetamide. 400 mg (30% yield) of compound 4c were isolated. $^1$H NMR (500 MHz, DMSO-d$_6$) δ PPM: 11.95 (br, 1H), 8.59 (d, 1H), 8.42 (d, 1H), 8.26 (s, 1H), 7.58 (d, 1H), 7.49 (d, 1H), 7.21 (t, 1H). Mass (m/z): 203.2, 205.2.

Synthesis of 6-chloro-9H-pyrido[2,3-b]indole 1-oxide (5c)

Compound 5c was prepared according to the procedure for compound 5 (Example 1) using compound 4c (380 mg, 1.88 mmol) and proportionate molar equivalents of aqueous H$_2$O$_2$ (35%) and CH$_3$COOH. 205 mg (50% yield) of compound 5c were isolated. Mass (m/z): 219.2, 221.2.

Synthesis of 4-bromo-6-chloro-9H-pyrido[2,3-b]indole (6c)

Compound 6c was prepared according to the procedure for compound 6 (Example 1) using compound 5c (200 mg, 0.917 mmol) and proportionate molar equivalents of anhydrous DMF and POBr$_3$. 90 mg (35% yield) of compound 6c were isolated. Mass (m/z): 283.0, 285.0.

Example 41

An exemplary procedure for the preparation of compound 6d:

Synthesis of 7-methoxy-9H-pyrido[2,3-b]indole (4d)

Compound 4d was prepared according to Example 11 using 3-methoxyaniline 21d (890 mg, 7.43 mmol) and proportionate molar equivalents of compound 20, Pd(OAc)$_2$, PPh$_3$, NaO$^t$Bu and o-xylene. Continuing according to Example 11, crude isolated compound 22d was converted to compound 4d using proportionate molar equivalents of Pd(OAc)$_2$, PCy$_3$, DBU and dimethyl acetamide. 355 mg (30% yield) of compound 4d were isolated. $^1$H NMR (500 MHz, DMSO-d$_6$) δ PPM: 11.61 (br, 1H), 8.38 (d, 1H), 8.34 (d, 1H), 7.18 (d, 1H), 6.90 (s, 1H), 6.81 (t, 1H), 3.82 (s, 3H), Mass (m/z): 199.2 (M+H).

Synthesis of 7-methoxy-9H-pyrido[2,3-b]indole 1-oxide (5d)

Compound 5d was prepared according to the procedure for compound 5 (Example 1) using compound 4d (330 mg, 1.67 mmol) and proportionate molar equivalents of aqueous H$_2$O$_2$ (35%) and CH$_3$COOH. 89 mg (25% yield) of compound 5d were isolated. Mass (m/z): 215.2 (M+H).

Synthesis of 4-bromo-7-methoxy-9H-pyrido[2,3-b]indole (6d)

Compound 6d was prepared according to the procedure for compound 6 (Example 1) using compound 5d (88 mg, 0.411 mmol) and proportionate molar equivalents of anhydrous DMF and POBr$_3$. 45 mg (40% yield) of compound 6d were isolated. Mass (m/z): 277.1, 279.1.

Example 42

An exemplary procedure for the preparation of compound I-11:

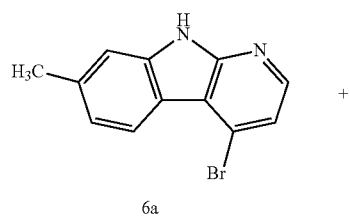

6a

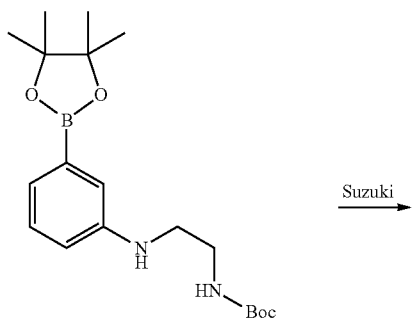

17a

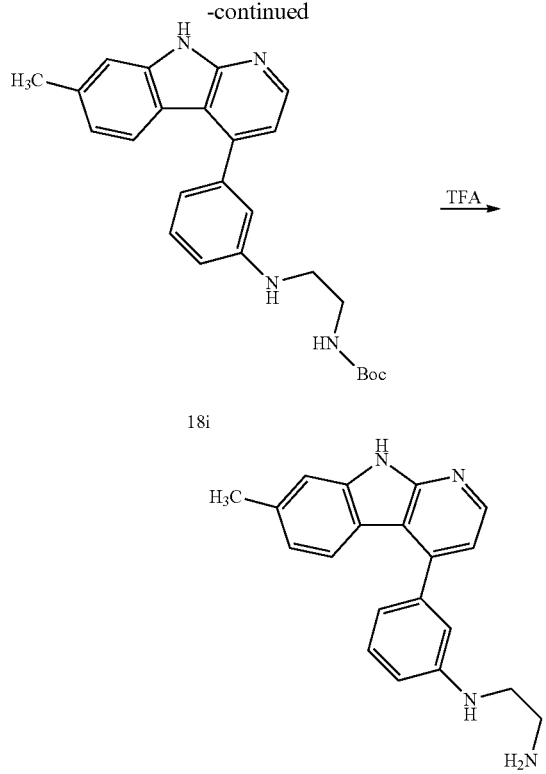

Synthesis of tert-butyl 3-(7-methyl-9H-pyrido[2,3-b]indol-4-yl)phenethyl carbamate (I-11)

Compound 18i was prepared according to the procedure for compound 18a (Example 27) using compound 6a (61 mg, 0.23 mmol) and proportionate molar equivalents of boronate ester 17a, aqueous sodium carbonate (2.0M), dioxane and Pd(PPh$_3$)$_4$. 49 mg (50% yield) of compound 18i were isolated. Mass (m/z): 417.3 (M+H).

Synthesis of 2-(3-(7-methyl-9H-pyrido[2,3-b]indol-4-yl)phenyl)ethanamine (I-11)

Compound I-11 was prepared according to the procedure for compound I-7 (Example 27) from compound 18i (49 mg, 0.117 mmol) and treating with proportionate molar equivalents of trifluoroacetic acid in anhydrous dichloromethane. Purification by preparative HPLC gave 14 mg (37% yield) of compound I-11. $^1$H NMR (500 MHz, DMSO-d$_6$) δ PPM: 11.89 (br, 1H), 8.39 (d, 1H), 7.58 (d, 1H), 7.35 (m, 2H), 7.05 (d, 1H), 6.86 (m, 3H), 6.80 (d, 1H), 6.02 (br, 1H), 2.98 (t, 2H), 2.40 (s, 3H). $^1$H NMR D$_2$O Exchange (500 MHz, DMSO-d$_6$) δ PPM: 8.32 (d, 1H), 7.50 (d, 1H), 7.35 (m, 2H), 7.05 (d, 1H), 6.86 (m, 3H), 6.80 (d, 1H), 3.35 (t, 2H), 2.98 (t, 2H), 2.38 (s, 3H). Mass (m/z): 317.3 (M+H).

Example 43

An exemplary procedure for the preparation of compound I-13:

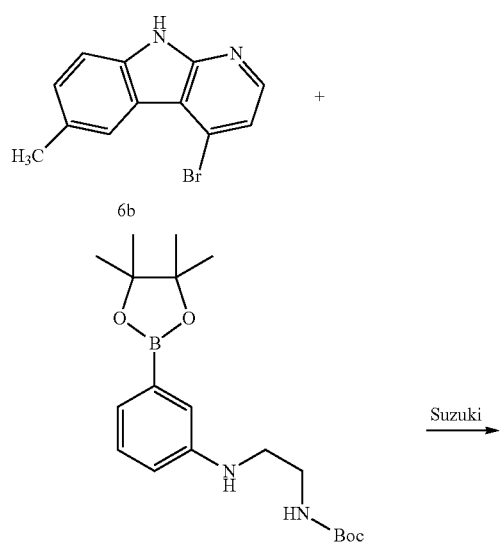

6b

17a

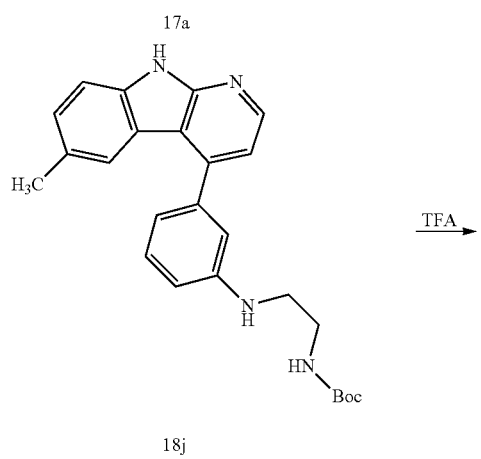

18j

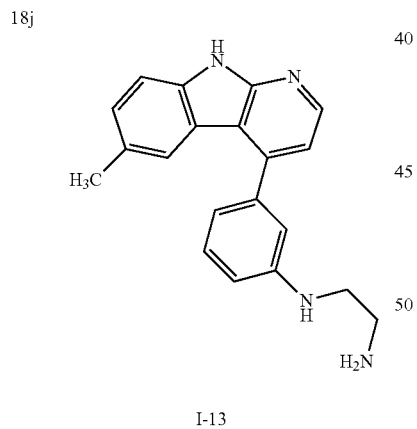

I-13

Synthesis of tert-butyl 3-(6-methyl-9H-pyrido[2,3-b]indol-4-yl)phenethylcarbamate (18j)

Compound 18j was prepared according to the procedure for compound 18a (Example 27) using compound 6b (68 mg, 0.256 mmol) and proportionate molar equivalents of boronate ester 17a, aqueous sodium carbonate (2.0M), dioxane and Pd(PPh$_3$)$_4$. 54 mg (49% yield) of compound 18j were isolated. Mass (m/z): 417.3 (M+H).

Synthesis of N1-(3-(6-methyl-9H-pyrido[2,3-b]indol-4-yl)phenyl)ethane-1,2-diamine (I-13)

Compound I-13 was prepared according to the procedure for compound I-7 (Example 27) using compound 18j (53 mg, 0.126 mmol) and proportionate molar equivalents of trifluoroacetic acid and anhydrous dichloromethane. Purification by preparative HPLC gave 16 mg (40% yield) of compound I-13. $^1$H NMR (500 MHz, DMSO-d$_6$) δ PPM: 11.95 (br, 1H), 8.62 (d, 1H), 7.70 (s, 1H), 7.65 (d, 2H), 7.58 (t, 1H), 7.45 (d, 1H), 7.24 (d, 1H), 7.10 (dd, 2H), 7.0 (d, 1H), 6.20 (br, 1H), 3.20 (t, 2H), 2.70 (s, 3H). $^1$H NMR D$_2$O Exchange (500 MHz, DMSO-d$_6$) δ PPM: 8.38 (d, 1H), 7.45 (m, 2H), 7.38 (t, 1H), 7.22 (d, 1H), 7.05 (d, 1H), 6.85 (m, 2H), 6.80 (d 1H), 3.35 (t, 2H), 2.98 (t, 2H), 2.22 (s, 3H). Mass (m/z): 317.3 (M+H).

Example 44

An exemplary procedure for the preparation of compound I-14:

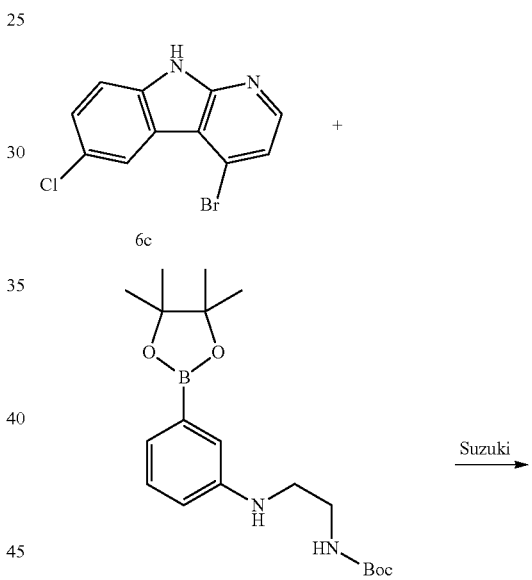

6c

17a

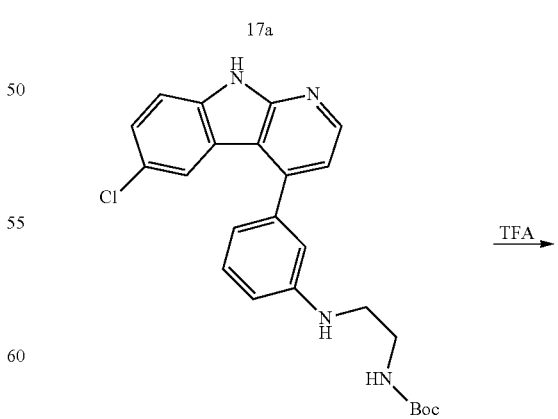

18k

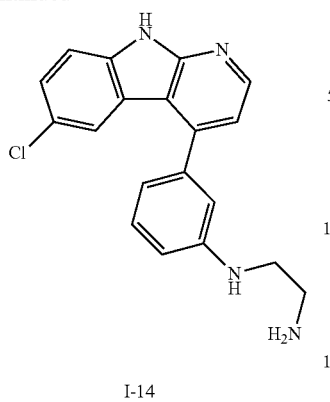

I-14

Synthesis of tert-butyl 3-(6-chloro-9H-pyrido[2,3-b]indol-4-yl) phenethyl carbamate (18k)

Compound 18k was prepared according to the procedure for compound 18a (Example 27) using compound 6c (85 mg, 0.302 mmol) and proportionate molar equivalents of boronate ester 17a, aqueous sodium carbonate (2.0M), dioxane and Pd(PPh₃)₄. 59 mg (45% yield) of compound 18k were isolated. Mass (m/z): 437.3, 439.3.

Synthesis of N1-(3-(6-chloro-9H-pyrido[2,3-b]indol-4-yl)phenyl)ethane-1,2-diamine (I-14)

Compound I-14 was prepared according to the procedure for compound I-7 (Example 1) using compound 18k (58 mg, 0.133 mmol) and proportionate molar equivalents of trifluoroacetic acid and anhydrous dichloromethane. Purification by preparative HPLC gave 15 mg (36% yield) of compound I-14. ¹HNMR (500 MHz, DMSO-d₆) δ PPM: 12.10 (br, 1H), 8.40 (d, 1H), 7.80 (br, 2H), 7.55 (s, 1H), 7.50 (d, 1H), 7.40 (d, 1H), 7.38 (t, 1H), 7.08 (d, 1H), 6.8 (m, 3H), 6.00 (br, 1H), 3.00 (t, 2H). ¹HNMR D₂O Exchange (500 MHz, DMSO-d₆) δ PPM: 8.38 (d, 1H), 7.59 (m, 2H), 7.39 (d, 1H), 7.35 (t, 1H), 7.15 (d, 1H), 6.89 (m, 3H), 3.38 (t, 2H), 2.98 (t, 2H). Mass (m/z): 337.2. 339.2.

Example 45

An exemplary procedure for the preparation of compound I-12:

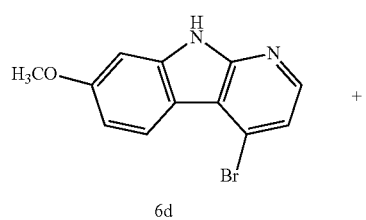

6d

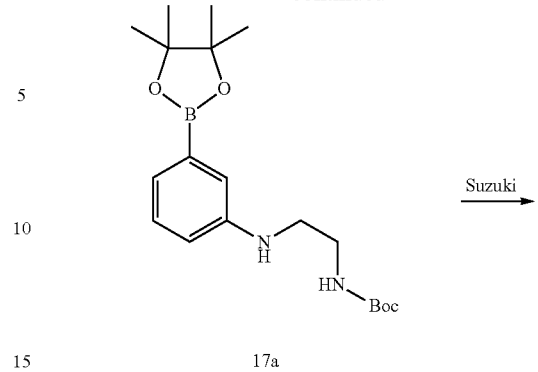

17a

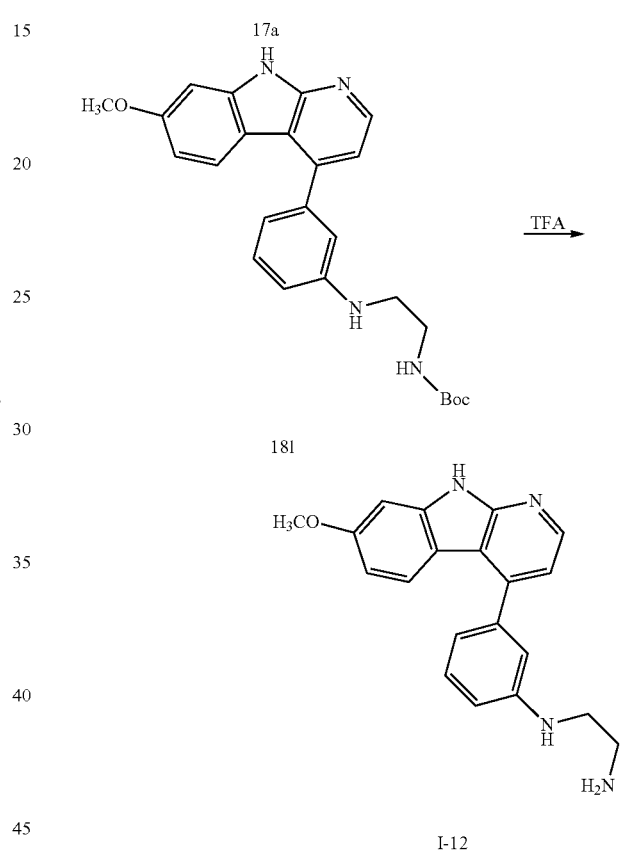

18l

I-12

Synthesis of tert-butyl 3-(6-methoxy-9H-pyrido[2,3-b]indol-4-yl)phenethyl carbamate (18l)

Compound 18l was prepared according to the procedure for compound 18a (Example 27) using compound 6d (44 mg, 0.158 mmol) and proportionate molar equivalents of boronate ester 17a, aqueous sodium carbonate (2.0M), dioxane and Pd(PPh₃)₄. 27 mg (40% yield) of compound 18l were isolated. Mass (m/z): 433.3 (M+H).

Synthesis N1-(3-(7-methoxy-9H-pyrido[2,3-b]indol-4-yl)phenyl)ethane-1,2-diamine (I-12)

Compound I-12 was prepared according to the procedure for compound 9 (Example 1) using compound 18l (27 mg, 0.062 mmol) and proportionate molar equivalents of trifluoroacetic acid and anhydrous dichloromethane. Purification by preparative HPLC gave 6.3 mg (30% yield) of compound I-12. Mass (m/z): 333.2 (M+H).

Example 46

In Vitro CaMKIIδ Activity Assay

An exemplary procedure for the in vitro CaMKIIδ inhibition assay, which can be used to determine the inhibitory action of compounds of the invention toward CaMKII, follows. The procedure is taken from Chao L H, et al., (2010) Nat Struct Mol Biol. 17(3): 264-272, which is incorporated herein by reference in its entirety.

The inhibition of CaMKII activity was evaluated using a coupled assay measuring ADP released following ATP hydrolysis and phosphor-transfer to the peptide substrate AC3 (KKALHRQETVDAL; SEQ ID NO: 1) (1). A full length, C-terminal His/Gln tagged CaMKIIδ construct was used (sequence in Table 3 below).

TABLE 3

Amino acid sequence of CaMKIIδ construct.

```
MASTTTCTRFTDEYQLFEELGKGAFSVVRRCMKI
PTGQEYAAKIINTKKLSARDHQKLEREARICRLL
KHPNIVRLHDSISEEGFHYLVFDLVTGGELFEDI
VAREYYSEADASHCIQQILESVNHCHLNGIVHRD
LKPENLLLASKSKGAAVKLADFGLAIEVQGDQQ
AWFGFAGTPGYLSPEVLRKDPYGKPVDMWACGV
ILYILLVGYPPFWDEDQHRLYQQIKAGAYDFPSP
EWDTVTPEAKDLINKMLTINPAKRITASEALKHP
WICQRSTVASMMHRQETVDCLKKFNARRKLKGA
ILTTMLATRNFSAAKSLLKKPDGVKESTESSNTT
IEDEDVKARKQEIIKVTEQLIEAINNGDFEAYTKI
CDPGLTAFEPEALGNLVEGMDFHRFYFENALSKS
NKPIHTIILNPHVHLVGDDAACIAYIRLTQYMDG
SGMPKTMQSEETRVWHRRDGKWQNVHFHRSGSP
TVPIKLGSFLDHSFGARAQVXGHNHNH (SEQ ID NO: 2)
```

Compounds were added in 5 uL volume to wells in UV transparent 96-well plates (½ area well size). The final compound concentrations tested ranged from 0.5 nM to 10 uM). Assays were performed in duplicate. CaMKIIδ is added to at a final concentration of 16 nM to a mixture containing 100 mM Tris (pH 7.5), 150 mM KCl, 0.27 mM EGTA, 1.3 mM PEP, 0.2 mg/ml AC3, 6.9% (v/v) PK/LDH mixture (Sigma P0294), 0.38 mM NADH and kept on ice. 72 uL of the enzyme mixture was added to the wells containing compounds and the plate was shaken briefly and kept on ice. The assay was initiated by adding 23 uL of a mixture containing 100 mM Tris (pH 7.5), 150 mM KCl, 1.7 mM CaCl2, 48 mM MgCl2, 0.35 mM ATP and 6.7 ug/mL calmodulin. The rate of ADP released was measured as the rate of absorbance decrease at 340 nM at 25° C. and plotted against the log of the compound concentration (FIG. 1). $IC_{50}$ data were fitted using GraphPad Prism software.

The results of the in vitro CaMKIIδ activity assays are set forth in Table 4. The compound numbers correspond to the compound numbers in Table 1, Table 2 and intermediates described in the Examples. Compounds having an activity designated as "A" provided an $IC_{50} \leq 50$ nM; compounds having an activity designated as "B" provided an $IC_{50}$ of 50-250 nM; compounds having an activity designated as "C" provided an $IC_{50}$ of 250-1000 nM; and compounds having an activity designated as "D" provided an $IC_{50} \geq 1$ μM. "NA" stands for "not assayed." The enzyme inhibition curve for compound I-7 against CaMKIIδ is shown in FIG. 1.

TABLE 4

Results of in vitro CaMKII activity inhibition assays.

| Compound ID | CaMKIIδ $IC_{50}$ | Compound ID | CaMKIIδ $IC_{50}$ |
| --- | --- | --- | --- |
| I-1 | B | 9a | C |
| I-2 | D | 9e | D |
| I-3 | D | 9h | D |
| I-4 | B | 9j | A |
| I-5 | C | 9k | D |
| I-6 | B | 9l | D |
| I-7 | A | 9m | D |
| I-8 | A | 9n | C |
| I-9 | A | 9o | D |
| I-10 | A | 8p | D |
| I-11 | A | 8q | C |
| I-12 | A | 8r | D |
| I-13 | A | | |
| I-14 | A | | |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound, wherein the compound is selected from:

| Compound ID | Compound Structure |
| --- | --- |
| 9a | 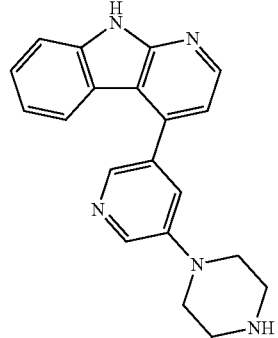 [SMILES: c1ccc2c(c1)[nH]c1nccc(-c3cncc(N4CCNCC4)c3)c12] |
| 9b | 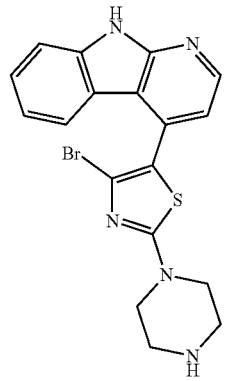 [SMILES: Brc1nc(N2CCNCC2)sc1-c1ccnc2[nH]c3ccccc3c12] |

-continued
| Compound ID | Compound Structure |
|---|---|
| 9c | 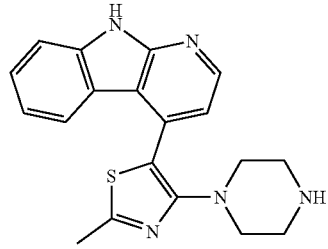 [SMILES: Cc1nc(N2CCNCC2)c(-c2ccnc3[nH]c4ccccc4c23)s1] |
| 9d | 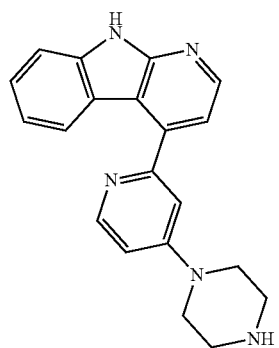 [SMILES: c1ccc2c(c1)[nH]c1nccc(-c3cc(N4CCNCC4)ccn3)c12] |
| 9e | 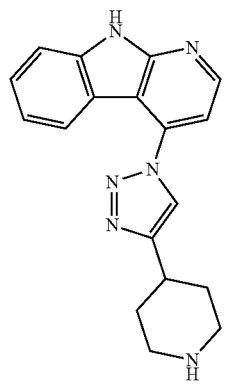 [SMILES: c1ccc2c(c1)[nH]c1nccc(-n3cc(C4CCNCC4)nn3)c12] |
| 9f | 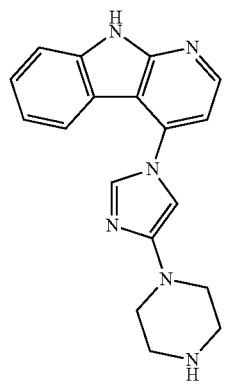 |
-continued
| Compound ID | Compound Structure |
|---|---|
| 9g | 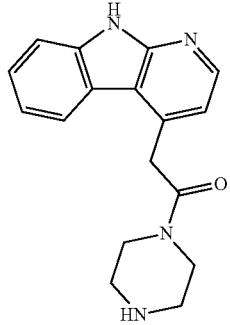 [SMILES: O=C(Cc1ccnc2[nH]c3ccccc3c12)N1CCNCC1] |
| 9h | 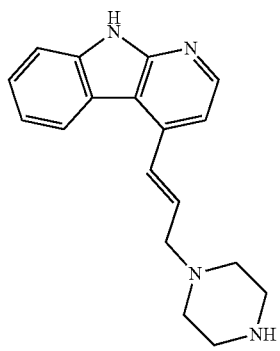 [SMILES: C(=C\c1ccnc2[nH]c3ccccc3c12)/CN1CCNCC1] |
| 9j | 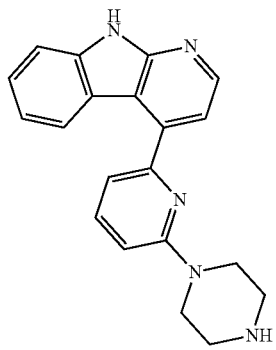 [SMILES: c1cc(-c2ccnc3[nH]c4ccccc4c23)nc(N2CCNCC2)c1] |
| 9k | 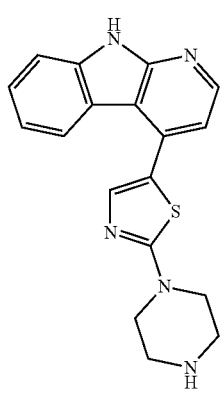 [SMILES: c1ccc2c(c1)[nH]c1nccc(-c3cnc(N4CCNCC4)s3)c12] |

-continued
| Compound ID | Compound Structure |
|---|---|
| 9l | 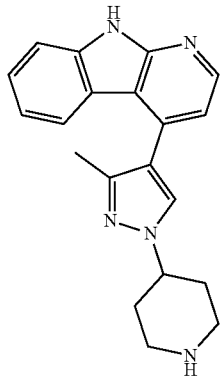 [SMILES: Cc1nn(C2CCNCC2)cc1-c1ccnc2[nH]c3ccccc3c12] |
| 9m | 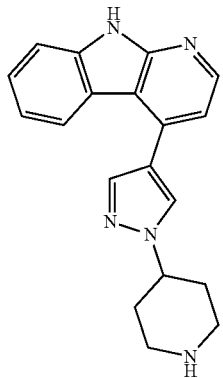 [SMILES: c1ccc2c(c1)[nH]c1nccc(-c3cnn(C4CCNCC4)c3)c12] |
| 9n | 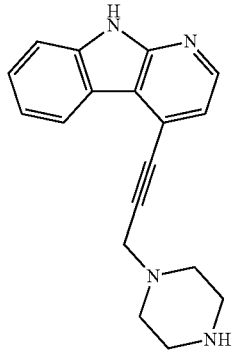 [SMILES: C(#Cc1ccnc2[nH]c3ccccc3c12)CN1CCNCC1] |
| 9o | 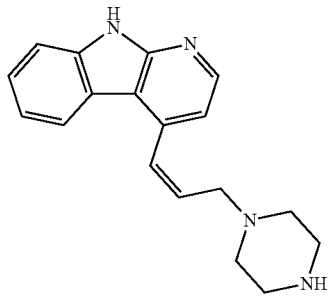 [SMILES: C(=C/c1ccnc2[nH]c3ccccc3c12)/CN1CCNCC1] |
-continued
| Compound ID | Compound Structure |
|---|---|
| 9p | 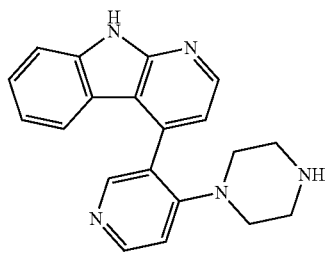 [SMILES: c1ccc2c(c1)[nH]c1nccc(-c3cnccc3N3CCNCC3)c12] |
| 9q | 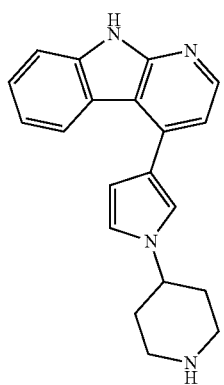 [SMILES: c1ccc2c(c1)[nH]c1nccc(-c3ccn(C4CCNCC4)c3)c12] |
| 9r | 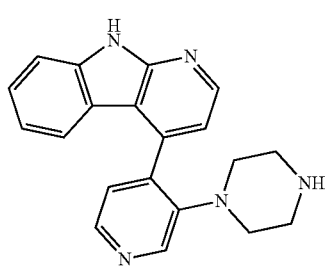 [SMILES: c1ccc2c(c1)[nH]c1nccc(-c3ccncc3N3CCNCC3)c12] |
| 9s | 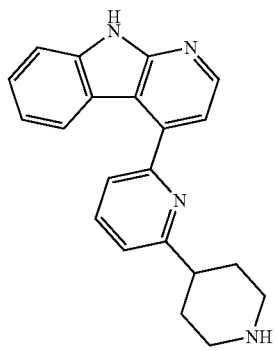 [SMILES: c1cc(-c2ccnc3[nH]c4ccccc4c23)nc(C2CCNCC2)c1] |
| 9t | 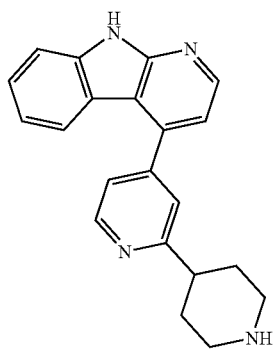 [SMILES: c1ccc2c(c1)[nH]c1nccc(-c3ccnc(C4CCNCC4)c3)c12] |

| Compound ID | Compound Structure |
|---|---|
| 9u | 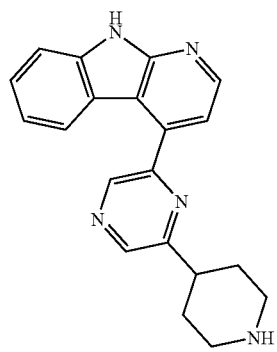 [SMILES: c1ccc2c(c1)[nH]c1nccc(-c3cncc(C4CCNCC4)n3)c12] |
| 9v | 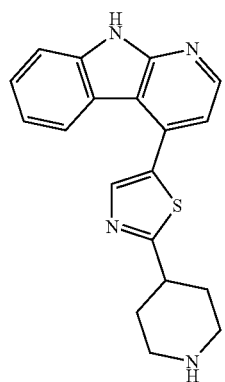 |
| 9w | 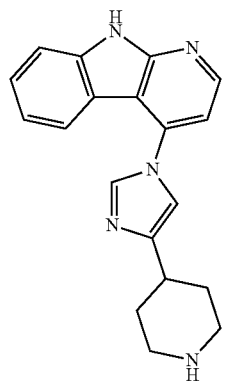 |
| 9x | 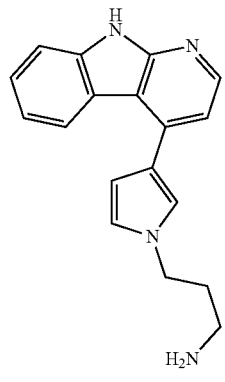 [SMILES: NCCCn1ccc(-c2ccnc3[nH]c4ccccc4c23)c1] |
| Compound ID | Compound Structure |
|---|---|
| 9y | 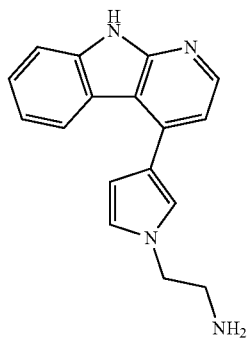 [SMILES: NCCn1ccc(-c2ccnc3[nH]c4ccccc4c23)c1] |
or a pharmaceutically acceptable salt thereof.
2. The compound of claim 1, wherein the compound is selected from:
| Compound ID | Compound Structure |
|---|---|
| 9a | 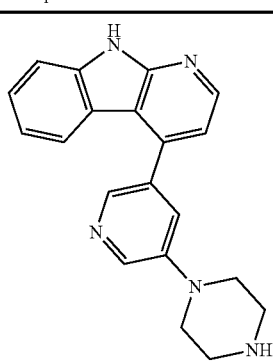 |
| 9d | 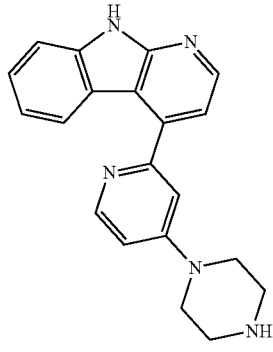 [SMILES: c1ccc2c(c1)[nH]c1nccc(-c3cc(N4CCNCC4)ccn3)c12] |
| 9j | 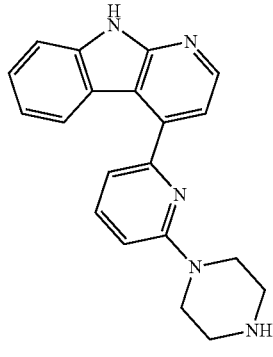 |

-continued
| Compound ID | Compound Structure |
|---|---|
| 9p | 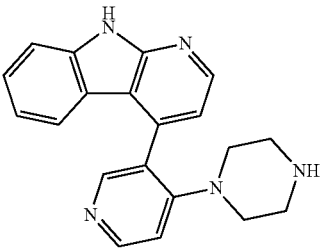 [SMILES: c1ccc2c(c1)[nH]c1nccc(-c3cnccc3N3CCNCC3)c12] |
| 9r | 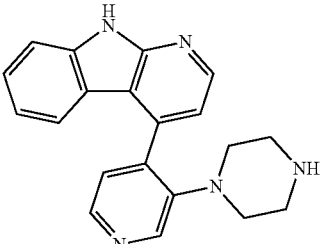 |
| 9s | 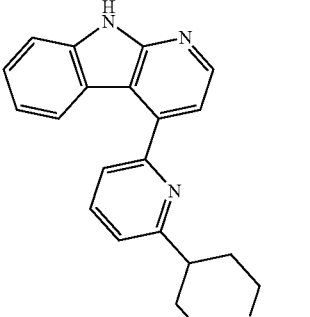 |
| 9t | 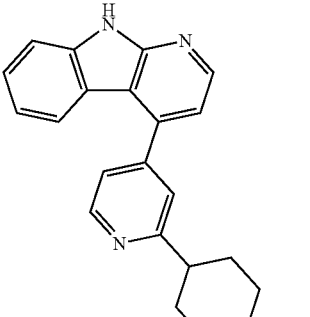 |
| 9u | 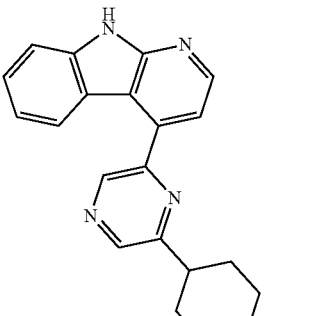 |
or a pharmaceutically acceptable salt thereof.
3. The compound of claim 1, wherein the compound is selected from:
| Compound ID | Compound Structure |
|---|---|
| 9b | 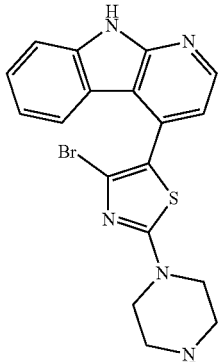 |
| 9c | 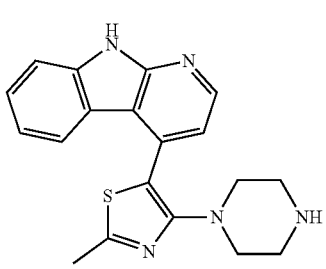 [SMILES: Cc1nc(N2CCNCC2)c(-c2ccnc3[nH]c4ccccc4c23)s1] |
| 9e | 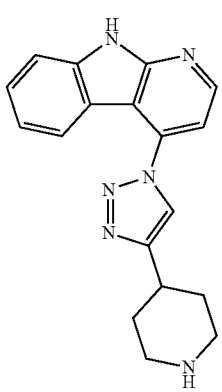 [SMILES: c1ccc2c(c1)[nH]c1nccc(-n3cc(C4CCNCC4)nn3)c12] |
| 9f | 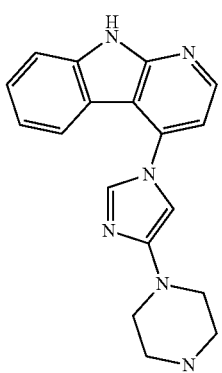 |

| Compound ID | Compound Structure |
|---|---|
| 9k | 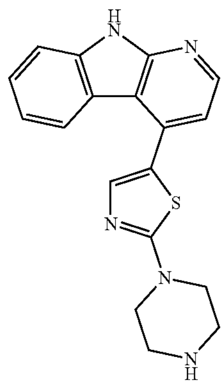 [SMILES: c1ccc2c(c1)[nH]c1nccc(-c3cnc(N4CCNCC4)s3)c12] |
| 9l | 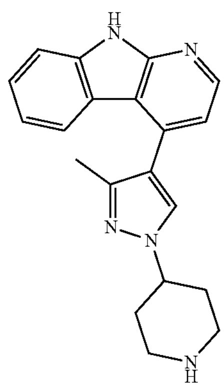 [SMILES: Cc1nn(C2CCNCC2)cc1-c1ccnc2[nH]c3ccccc3c12] |
| 9m | 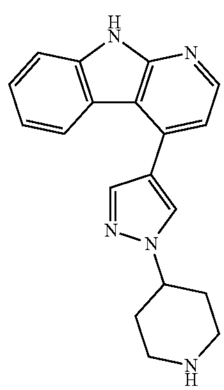 [SMILES: c1ccc2c(c1)[nH]c1nccc(-c3cnn(C4CCNCC4)c3)c12] |
| 9q | 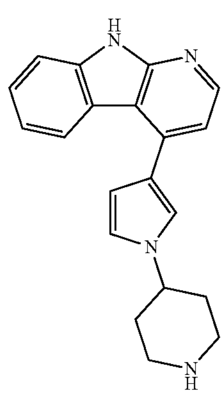 [SMILES: c1ccc2c(c1)[nH]c1nccc(-c3ccn(C4CCNCC4)c3)c12] |

| Compound ID | Compound Structure |
|---|---|
| 9v | |
| 9w | |
| 9x | |
| 9y | | or a pharmaceutically acceptable salt thereof.

4. The compound of claim 1, wherein the compound is selected from:

| Compound ID | Compound Structure |
|---|---|
| 9g | (structure: 9H-pyrido[2,3-b]indole with -CH2-C(=O)-N(piperazine) at position 4) |
| 9h | (structure: 9H-pyrido[2,3-b]indole with -CH=CH-CH2-piperazine at position 4) |
| 9n | (structure: 9H-pyrido[2,3-b]indole with -C≡C-CH2-piperazine at position 4) |

| Compound ID | Compound Structure |
|---|---|
| 9o | (structure: 9H-pyrido[2,3-b]indole with cis -CH=CH-CH2-piperazine at position 4) | or a pharmaceutically acceptable salt thereof.

5. The compound of claim 1, wherein the compound is:

| | |
|---|---|
| 9j | (structure: 9H-pyrido[2,3-b]indole with 6-(piperazin-1-yl)pyridin-2-yl at position 4) | or a pharmaceutically acceptable salt thereof.

\* \* \* \* \*